(12) United States Patent
Zohdy et al.

(10) Patent No.: US 11,549,868 B2
(45) Date of Patent: Jan. 10, 2023

(54) DIROFILARIA VOLATILE ORGANIC COMPOUND SIGNATURES AND USES THEREOF

(71) Applicant: AUBURN UNIVERSITY, Auburn, AL (US)

(72) Inventors: Sarah M. Zohdy, Opelika, AL (US); Lindsay Starkey, Auburn, AL (US); Byron L. Blagburn, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 0 days.

(21) Appl. No.: 17/488,966

(22) Filed: Sep. 29, 2021

(65) Prior Publication Data
US 2022/0205878 A1    Jun. 30, 2022

Related U.S. Application Data

(63) Continuation of application No. PCT/US2021/020007, filed on Feb. 26, 2021.

(60) Provisional application No. 63/049,371, filed on Jul. 8, 2020, provisional application No. 62/983,348, filed on Feb. 28, 2020.

(51) Int. Cl.
| | |
|---|---|
| A61K 31/555 | (2006.01) |
| A61K 45/06 | (2006.01) |
| G01N 1/22 | (2006.01) |
| A61B 10/00 | (2006.01) |
| A61K 31/65 | (2006.01) |
| G01N 30/02 | (2006.01) |
| G01N 33/497 | (2006.01) |

(52) U.S. Cl.
CPC ............. *G01N 1/22* (2013.01); *A61B 10/00* (2013.01); *A61K 31/555* (2013.01); *A61K 31/65* (2013.01); *A61K 45/06* (2013.01); *G01N 30/02* (2013.01); *G01N 33/497* (2013.01); *A61B 2010/0087* (2013.01); *A61B 2503/40* (2013.01); *G01N 2001/2244* (2013.01); *G01N 2030/025* (2013.01)

(58) Field of Classification Search
CPC .............................. A61K 31/555; A61K 45/06
See application file for complete search history.

(56) References Cited

U.S. PATENT DOCUMENTS

| | | |
|---|---|---|
| 10,000,811 B2 | 6/2018 | Prichard et al. |
| 2013/0137669 A1 | 5/2013 | Prichard et al. |
| 2017/0196854 A1 | 7/2017 | Chassaing et al. |

OTHER PUBLICATIONS

Knols, et al., "Differential attractiveness of isolated humans to mosquitoes in Tanzania," Transactions of the Royal Society of Tropical Medicine and Hygiene (1995), all enclosed pages cited.
"Heartworm Disease: The Science, The Practice, The Future," 2016 Triennial Symposium, American Heartworm Society, all enclosed pages cited.
Paredi, et al., "Elevation of Exhaled ethane concentration in asthma," Am J Respir Grit Care Med, vol. 162, (2000) all enclosed pages cited.
Courtney, et al., "Comparison of heartworm antigen test kit performance in dogs having low heartworm burdens," Veterinary Parasitology 96 (2001), all enclosed pages cited.
O'Shea, et al., "Enhanced sandfly attraction to Leishmania-infected hosts," Transactions of the Royal Society of Tropical Medicine and Hygiene, (2002) 96, all enclosed pages cited.
Atkins, C.E., "Comparison of results of three commercial heartworm antigen test kits in dogs with low heartworm burdens," JAVMA, vol. 222, No. 9, May 1, 2003, all enclosed pages cited.
Venco, et al., "Efficacy of long-term monthly administration of ivermectin on the progress of naturally acquired heartworm infections in dogs," Veterinary Parasitology 124 (2004), all enclosed pages cited.
Mukabana, et al., "Allomonal effect of breath contributes to differential attractiveness of humans to the African malaria vector Anopheles gambiae," Malaria Journal 2004, 3:1, all enclosed pages cited.
Barker, et al., "Volatile organic compounds in the exhaled breath of young patients with cystic fibrosis," Eur Respir J 2006, all enclosed pages cited.
Rock, et al., "Electronic Nose: Current Status and Future Trends," Chem. Rev. 2008, 108, all enclosed pages cited.
De Oliveira, et al., "Headspace solid phase microextraction/gas chromatography—mass spectrometry combined to chemometric analysis for volatile organic compounds determination in canine hair: A new tool to detect dog contamination by visceral leishmaniasis," Journal of Chromatography B, 875 (2008), all enclosed pages cited.
Kischkel, et al., "Breath biomarkers for lung cancer detection and assessment of smoking related effects—confounding variables, influence of normalization and statistical algorithms," Clinica Chimica Acta 411 (2010), all enclosed pages cited.
De Gennaro, et al., "Chemical characterization of exhaled breath to differentiate between patients with malignant plueral mesothelioma from subject with similar professional asbestos esposure," Anal Bioanal Chem (2010) 398, all enclosed pages cited.
Tang, et al., "A colormetric sensor for Qualitative discrimination and quantitative detection of volatile amines," Sensors 2010, 10, all enclosed pages cited.
Lee, et al., "Evaluation of a new in-clinic method for the detection of canine heartworm antigen," Veterinary Parasitology 177 (2011), all enclosed pages cited.
Van de Kant, et al., "Clinical use of exhaled volatile organic compounds in pulmonary diseases: a systematic review," Respiratory Research, 2012 13:117, all enclosed pages cited.
Montuschi, et al., "The Electronic nose in respiratory medicine," Respiration 2013; 85, all enclosed pages cited.
Broza, et al., "Nanomaterial-based sensors for detection of disease by volatile organic compounds," Nanomedicine (2013) 8(5), all enclosed pages cited.

(Continued)

*Primary Examiner* — Yong S. Chong
(74) *Attorney, Agent, or Firm* — Carin R. Miller, Esq.; Johnson, Marcou, Isaacs & Nix, LLC

(57) ABSTRACT

Described herein are Dirofilarial exhalant signatures and methods of detecting a Dirofilaria signature in a non-blood biological sample, such as exhalant, that can be used to detect Dirofilarial infection in a subject, such as a canine.

14 Claims, 27 Drawing Sheets

(56) References Cited

OTHER PUBLICATIONS

Alkhouri, et al., "Analysis of breath volatile organic compounds as a noninvasive tool to diagnose nonalcoholic fatty liver disease in children," European Journal of Gastroenterology & Hepatology, 2014, all enclosed pages cited.

Magalhaes-Junior, et al., "Identification of biomarkers in the hair of dogs: new diagnostic possibilities in the study and control of visceral leishmaniasis," Anal Bioanal Chem (2014), 406, all enclosed pages cited.

De Moraes, et al., "Malaria-induced changes in host odors enhance mosquito attraction," PNAS vol. 111, No. 30, (2014), all enclosed pages cited.

Bikov, et al., "Established methodological issues in electronic nose research: how far are we from using these instruments in clinical settings of breath analysis?," J Breath Res 9 034001 (2015), all enclosed pages cited.

Vishinkin, et al., "Nanoscale sensor technologies for disease detection via Volatomics," Small 2015, 11, No. 46, all enclosed pages cited.

Borges, et al., "Identification of non-host semiochemicals for the brown dog tick, Rhipicephalus sanguineus sensu lato (Acari: Ixodidae), from tick-resistant beagles, Canis lupus familiaris," Ticks and Tick-borne Diseases 6 (2015), all enclosed pages cited.

Berna, et al., "Analysis of breath specimens for biomarkers of Plasmodium falciparum Infection," JID 2015:212 (Oct. 1), all enclosed pages cited.

Holderman, et al., "Novel collection method for volatile organic compounds (VOCs) from dogs," Journal of Chromatography B, 1061-1062 (2017), all enclosed pages cited.

Spinelle, et al., "Review of portable and low-cost sensors for the ambient air monitoring of benzene and other volatile organic compounds," Sensors (2017), 17, all enclosed pages cited.

Bendas, et al., "Heat pretreatment of canine samples to evaluate efficacy of imidacloprid + moxidectin and doxycycline in heartworm treatment," Parasites & Vectors, (2017) 10:246, all enclosed pages cited.

Robinson, et al., "Plasmodium-associated changes in human odor attract mosquitos," PNAS vol. 115, No. 18 (2018), all enclosed pages cited.

Savadelis, et al., "Evaluation of heat-treating heartworm-positive canine serum samples during treatment with Advantage Multi for dogs and doxycycline," Parasites & Vectors (2018) 11:98, all enclosed pages cited.

Little, et al., "Prime detection of Dirofilaria immitis: understanding the influence of blocked antigen on heartworm test performance," Parasites & Vectors (2018) 11:186, all enclosed pages cited.

Kramer, et al., "Wolbachia, doxycycline and macrocyclic lactones: New prospects in the treatment of canine heartworm disease," Veterinary Parasitology 254 (2018), all enclosed pages cited.

Hashoul, et al., "Sensors for detecting pulmonary diseases from exhaled breath," Eur Respir Rev 2019; 28, all enclosed pages cited.

Genchi, et al., "Efficacy of imidacloprid 10%/moxidectin 2.5% spot on (Advocate, Advantage Multi) and doxycycline for the treatment of natural Dirofilaria immitis infections in dogs," Veterinary Parasitology 273 (2019), all enclosed pages cited.

Zohdy, et al., "Do Canids infected with Dirofilaria Immitis Release Unique Volatile Organic Compounds in their Breath?," 27th Conference of the World Association for the Advancement of Veterinary Parasitology, Jul. 11, 2019, all enclosed pages cited.

Savadelis, et al., "Clinical assessment of heartworm-infected Beagles treated with a combination of imidacloprid/moxidectin and doxycycline, or untreated," Journal of Veterinary Internal Medicine, 34 (2020), all enclosed pages cited.

Ames, et al., "Non-arsenical heartworm adulticial therapy using topical moxidectin-imidacloprid and doxycycline: A prospective case series," Veterinary Parasitology 282 (2020), all enclosed pages cited.

Carreton, et al., "Evaluation of serum biomarkers and proteinuria for the early detection of renal damage in dogs with heartworm (*Dirofilaria immitis*)," Veterinary Parasitology 283 (2020) 109144, all enclosed pages cited.

Paterson, et al., "Heartworm control in Grenada, West Indies: Results of a field study using imidacloprid 10% + moxidectin 2.5% and doxycycline for naturally-acquired Dirofilaria immitis infections," Veterinary Parasitology 284 (2020), all enclosed pages cited.

Alberigi, et al., "Use of Slow-release injectable moxidectin for treatment of Dirofilaria immitis infection during pregnancy," Frontiers in Veterinary Science, vol. 6, Article 440, Jan. 28, 2020, all enclosed pages cited.

Wang, et al., "Volatile organic compounds gas sensors based on molybendum oxides: a mini review," Frontiers in Chemistry, vol. 8, Article 339, (2020), all enclosed pages cited.

Li, et al., "Recent advances of SnO2-Based sensors for detecting volatile organic compounds," Frontiers in Chemistry, vol. 8, Article 321, (2020), all enclosed pages cited.

Invitation to Pay Additional Fees of Application No. PCT/US2021/020007 mailed May 5, 2021, all enclosed pages cited.

International Search Report and Written Opinion of Application No. PCT/US2021/020007 dated Jul. 15, 2021, all enclosed pages cited.

| All Highest Quartile (negative) | | | |
|---|---|---|---|
| 3.08 min | 3.54 min | 3.68 min | 3.94 min |
| 1 | 1 | A14 | 1 |
| 2 | 7 | AD14 | 6 |
| 4 | A14 | AD14 | 20 |
| 5 | A25 | AD2 | 25 |
| 6 | A8 | AD33 | A15 |
| 7 | AD14 | AD33 | A20 |
| 15 | AD14 | AD50 | A25 |
| 17 | AD20 | AD55 | A6 |
| 18 | AD3 | AD56 | AD2 |
| 21 | AD33 | B8 | AD24 |
| 24 | AD50 | C13 | AD33 |
| 26 | AD6 | C15 | AD5 |
| 27 | AD7 | C5 | AD55 |
| A31 | AD55 | C7 | D4 |
| AD55 | B8 | D24 | E10 |
|  | C13 | D4 | postLevy |
|  | C13 | E13 |  |
|  | C7 | L2 |  |
|  | D24 |  |  |
| All Lowest Quartile (positive) | | | |
| 3.08 min | 3.54 min | 3.68 min | 3.94 min |
| A18 | AD8 | 3 | 4 |
| A20 | 3 | 4 | 5 |
| A20 | 4 | 5 | 13 |
| A21 | 5 | 6 | 15 |
| A22 | 18 | 13 | 26 |
| A6 | 20 | 18 | A13 |
| AD1 | 24 | 20 | A14 |
| AD11 | 25 | 24 | A17 |
| AD15 | 27 | 25 | A2 |
| AD2 | A13 | 27 | A22 |
| AD44 | A15 | A13 | A4 |
| AD44 | A16 | A16 | A8 |
| AD48 | A21 | A23 | AD1 |
| AD49 | A22 | A6 | AD11 |
| AD5 | A6 | AD27 | AD15 |
| C11 | E10 | D12 | AD44 |
| D12 | PostLevy | PostLevy | AD49 |
| E10 | Valve22 | Valve22 | AD49 |
|  |  |  | AD6 |
|  |  |  | C11 |
|  |  |  | C15 |
|  |  |  | C5 |
|  |  |  | D12 |
|  |  |  | D15 |
|  |  |  | E15 |

FIG. 13

17.6% probability
Name: 5,6,7,8,9,10-Hexahydrobenzocyclooctene
Formula: C$_{12}$H$_{16}$
MW: 160 CAS#: 1076-69-3

10.7% probability
Name: Biphenylene, 1,2,3,6,7,8,8a,8b-octahydro-, trans-
Formula: C$_{12}$H$_{16}$
MW: 160 CAS#: 28229-15-4

DIROFILARIA VOLATILE ORGANIC COMPOUND SIGNATURES AND USES THEREOF

CROSS-REFERENCE TO RELATED APPLICATIONS

This application is a continuation under 35 U.S.C. § 111(a) of Patent Cooperation Treaty Application No.: PCT/US2021/020007, filed on Feb. 26, 2021, entitled DIROFILARIA VOLATILE ORGANIC COMPOUND SIGNATURES AND USES THEREOF," the contents of which is incorporated by reference herein in its entirety. Patent Cooperation Treaty Application No.: PCT/US2021/020007 claims the benefit of and priority to U.S. Provisional Patent Application No. 62/983,348, filed on Feb. 28, 2020, entitled "Detection of Canine Heartworm Infection Through Breath Odorant Volatiles," and U.S. Provisional Patent Application No. 63/049,371, filed on Jul. 8, 2020, entitled "Detection of Canine Heartworm Infection Through Breath Odorant Volatiles," the contents of which are incorporated by reference herein in their entireties.

TECHNICAL FIELD

The subject matter disclosed herein is generally directed to diagnosis, treatment, and/or prevention of dirofilarial infection.

BACKGROUND

Heartworm infection and disease is diagnosed in domestic and non-domestic canines in all 50 U.S. states and in areas outside of the United States. A 2019 study conducted by the American Heartworm Society (AHS) revealed that while no state is free of heartworm disease, dogs in the South, particularly dogs in the Southeast were most often affected. Indeed, the top five affected states according to this survey were Mississippi, Louisiana, South Carolina, Arkansas, and Alabama. These states have been in the top tier of affected states since the AHS began tracking incidence data in 2001. In 2019, almost 10 percent of dogs tested for heartworms in Mississippi were positive and just under 8 percent of dogs that were tested for heartworms in Louisiana were positive. Rounding out the top 10 states based on incidence data were Texas, Tennessee, Georgia, North Carolina, and Oklahoma.

Moreover, the number of veterinary practices surveyed that reported seeing heartworm cases has increased since the last AHS survey completed in 2016, which 26 percent of veterinarians observing and reporting an upward trend in cases and 57 percent of veterinarians reporting there has not been an observable change in the number of cases they see each year. Those that did report an observed decrease also reported an corresponding increase in the use of heartworm prevention. Those reporting an upward trend in cases also reported a corresponding influx of heartworm-positive patients into their practice area and poor prevention compliance (e.g., missing or skipping doses).

Heartworm disease in dogs (and in other hosts where they can be pathogenic such as cats and humans) is caused by Dirofilaria immitis (D. immitis). Detection of heartworms is typically done by detecting blood circulating D. immitis antigen, which has been in clinical practice for over three decades. This may also be coupled with a blood smear evaluating for the presence of circulating microfilariae. However, these methods are not failproof. Indeed, circulating D. immitis antigen may not be available for detection and can only be exposed with heat treatment of the sample, which was well documented in the 1980's (see e.g., Little et al. 2018. Parasites & Vectors. 11: Article No. 186); heat treatment of samples is not necessarily standard practice in clinics. Further, although the clinical antigen detection tests are very specific for circulating female D. immitis antigen, the sensitivity of these tests can vary widely (see e.g., Little et al., 2018 at e.g., Tables 2 and 3) due to variances in the platform for a given antigen test, test performance characteristics, and the age and number of female heartworms present (tests are only specific for female heartworm antigen) (see e.g., Atkins, C. E. J Am Vet Med Assoc. 2003. 222:1221-1223; Courtney et al. Vet Parasitol. 2001.96:317-322; Lee et al., Vet Parasitol. 2011. 177:381-391). Repeated evaluation of the same test(s) has also been observed to yield different performance characteristics due to differences in specimens included in the analysis, test kit version, procedures used, and method of heartworm infection verification (see e.g., Courtney, C. H., 2001. Comparing the performance of heartworm antigen tests in dogs. In: Soll M D, editor. Recent Advances in Heartworm Disease Symposium '01. Batavia, Illinois: American Heartworm Society; 2001. p. 105-10). Further, all current antigen and microfilariae tests require a blood sample. This increases the expertise required to screen for infection and inherently limits who can perform such a test. For example, although it may be desirable for non-veterinary personnel to at least obtain samples to be sent to a veterinarian for analysis, such as animal shelter personnel, animal rescue organization personnel, law-enforcement, and the like, because a blood draw is required for current testing methods, such an approach is impractical simply because of the skill required to obtain a blood sample. Further, many animals may display behaviors that make a blood draw impractical in settings outside of a vet clinic, particularly for those not skilled in animal-handling.

Although current diagnostic tests based on circulating blood antigen have helped make great progress in the identification, treatment, and awareness of heartworm disease, there are still limitations and drawbacks to these tests that provide barriers for wider, easier, and/or more frequent implementation. Thus, there exists an urgent and unmet need for alternative and/or improved diagnostics for heartworms in dogs and hosts.

Citation or identification of any document in this application is not an admission that such a document is available as prior art to the present invention.

SUMMARY

Described in certain example embodiments herein are Dirofilaria exhalant signatures comprising one or more volatile organic compounds (VOCs) selected from the group consisting of: an aromatic hydrocarbon, a monoterpene, a cyclopentanone, an aziridine, an alkane hydrocarbon, a phenol, a ketone, and combinations thereof.

In certain example embodiments, the number of VOCs in the Dirofilaria exhalant signature is 1, 2, 3, 4, 5, 6, 7, 8, 9, 10, 11, 12, 13, 15, or 15.

In certain example embodiments, the number of VOCs in the Dirofilaria exhalant signature is 9 and wherein the 9 VOCs are an aromatic hydrocarbon, a monoterpene, an alkyl alcohol, a cyclopentanone, an aziridine, two alkane hydrocarbons, a phenol, and a ketone.

In certain example embodiments, the one or more VOCs are ortho xylene, p-Methane-1,2,3-triol, 3,7,11-trimethyl-1-Dodecanol, 2-ethyl-Cyclohexanone, 2-mehtyl-2-(2,2,4,4,6, 6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

In certain example embodiments, the one or more VOCs are selected from the group consisting of: ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

In certain example embodiments, the Dirofilaria exhalant signature is a Dirofilaria *immitis*, Dirofilaria *repens*, Dirofilaria *tenuis*, Dirofilaria *ursi*, D. subdermata, *D. striata*, or a *D. hongkongensis* exhalant signature.

Described in certain example embodiments herein are non-invasive methods of diagnosing, prognosing, staging, and/or monitoring Dirofilaria infection in a subject, the method comprising detecting a Dirofilaria exhalant signature in an exhalant sample obtained from the subject, wherein the Dirofilaria exhalant signature is as in any one of any one of the preceding paragraphs and elsewhere herein, whereby detection of a decrease, increase, or both of one or more VOCs of the Dirofilaria exhalant signature as compared to a threshold value, a suitable control, or both indicates the presence or absence of Dirofilaria infection in the subject.

In certain example embodiments, the Dirofilaria infection is a Dirofilaria *immitis* infection.

In certain example embodiments, the subject is a human.

In certain example embodiments, the subject is a non-human animal.

In certain example embodiments, the subject is a canine.

Described in certain example embodiments herein are methods of treating and/or preventing Dirofilaria infection in a subject, the method comprising non-invasively diagnosing, prognosing, and/or staging Dirofilaria infection in the subject by detecting a Dirofilaria exhalant signature in an exhalant sample obtained from the subject, wherein the Dirofilaria exhalant signature is as in any one of the preceding paragraphs and elsewhere herein, whereby detection of a decrease, increase, or both of one or more VOCs of the Dirofilaria exhalant signature as compared to a threshold value, a suitable control, or both indicates the presence or absence of Dirofilaria infection in the subject; and administering to the subject an anthelmintic effective to prevent at least the adult stage of Dirofilaria in the subject one or more times, administering to the subject a treatment effective to kill the adult stage of Dirofilaria in the subject one or more times, or both.

In certain example embodiments, the subject is a non-human animal.

In certain example embodiments, the subject is a canine.

In certain example embodiments, the Dirofilaria is *D. immitis*.

In certain example embodiments, the anthelmintic effective to prevent at least the adult stage of Dirofilaria comprises ivermectin, moxidectin, milbemycin oxime, selamectin, eprinomectin, or a combination thereof.

In certain example embodiments, the method further comprises co-administering a composition effective to prevent, treat, or both an intestinal parasite, an external parasite, or both.

In certain example embodiments, the composition effective to prevent, treat, or both an intestinal parasite, an external parasite, or both is one or more compounds of one or more of the following classes benzimidazole, piperazine, depolarizing tetrahydropyrimidines, a macrocyclic lactone, neonicotinoid, phenylpyrazole, oxadiazine, pyrethrin, pyrethroid, isoxazoline, an insect growth regulator, or any combination thereof.

In certain example embodiments, the composition effective to prevent, treat, or both an intestinal parasite, external parasite, or both is selected from pyrantel, pyrantel pamoate, febantel, praziquantel, oxibendazole, piperazine, spinosad, fluralaner, afoxolaner, fipronil, sarolaner, lotilaner, lufenuron, imidacloprid, Methoprene, S-methoprene, pyriproxyfen, fenbendazole, flumethrin, selamectin, eprinomectin, indoxacarb, permethrin, nitenpyram, or any combination thereof.

In certain example embodiments, the treatment effective to kill the adult stage of Dirofilaria comprises administering melarsomine to the subject.

In certain example embodiments, the treatment effective to kill the adult stage of Dirofilaria comprises administering a macrocyclic lactone anthelmintic effective to kill adult Dirofilaria.

In certain example embodiments, the subject is administered treatment effective to kill the adult stage of Dirofilaria and the method further comprises administering an amount of doxycycline for two or more concurrent days to the subject.

In certain example embodiments, the amount of doxycycline is administered for about 30 days.

Described in certain example embodiments here are devices configured to collect an exhalant for analysis of volatile organic compounds (VOCs) present in the exhalant of a single non-human animal subject, comprising an exhalant collector configured to actively and non-invasively collect exhalant expelled from the non-human animal subject without being placed in an orifice of the subject; and one or more removable collection chambers, each removable collection chamber configured to hold an amount of exhalant collected and are suitable for containment of VOCs, wherein the one or more removable collection chambers are operatively coupled to the exhalant collector.

In certain example embodiments, the exhalant collector comprises or is coupled to one or more low pressure air pumps capable of moving exhalant external to the device into the exhalant collector and into the one or more removable collection chambers.

In certain example embodiments, the device comprises one or more one-way air valves configured to control the flow of exhalant in one direction through the device from the external environment through the exhalant collector and into and optionally through the one or more removable collection chambers.

In certain example embodiments, the exhalant collector is a tube that is configured to be placed in effective proximity to a mouth, nose, nostrils, or a combination thereof of the subject during collection and draw exhalant into the exhalant collector.

In certain example embodiments, the exhalant collector is a mask that is configured to cover the mouth and nose of the subject.

In certain example embodiments, the exhalant collector, the one or more removable collection chambers, or both comprise one or more filters.

In certain example embodiments, at least one of the one or more filters is effective to remove environmental VOCs from exhalant collected.

In certain example embodiments, the exhalant collector is operatively coupled to the one or more removable collection chambers via one or more tubes.

In certain example embodiments, the one or more removable collection chambers is configured to preserve VOCs for analysis.

In certain example embodiments, the one or more removable collection chambers comprises a material capable of capturing and retaining VOCs from collected exhalant.

In certain example embodiments, the one or more removable collection chambers is capable of concentrating and/or enriching VOCs from collected exhalant.

In certain example embodiments, the one or more removable collection chambers comprises a material capable of releasing VOCs that are captured by a material in the one or more removable collection chambers.

In certain example embodiments, the one or more collection chambers are tubes, bags, reservoirs, cartridges, or a combination thereof.

Described in certain example embodiments herein are kits comprising one or more removable collection chambers configured for the device of any one of the preceding paragraphs and elsewhere herein and instructions fixed in a tangible medium of expression wherein the instructions provide directions for using the one or more removable collection chambers to collect volatile organic compounds from an exhalant of a subject and detecting a Dirofilaria exhalant signature to diagnose, prognose, and/or stage a Dirofilaria infection in the subject.

In certain example embodiments, the one or more removable collection chambers is configured to preserve VOCs for analysis.

In certain example embodiments, the one or more removable collection chambers wherein the one or more removable collection chambers is capable of concentrating and/or enriching VOCs from collected exhalant.

In certain example embodiments, the one or more removable collection chambers comprises a material capable of releasing VOCs that are captured by a material in the one or more removable collection chambers.

Described in certain example embodiments herein are kits comprising a device as in any one of the preceding paragraphs and elsewhere herein and directions fixed in a tangible medium of expression for using the one or more removable collection chambers to collect volatile organic compounds from an exhalant of a subject and detecting a Dirofilaria exhalant signature to diagnose, prognose, and/or stage a Dirofilaria infection in the subject.

Described in certain example embodiments herein is the use of a Dirofilaria exhalant signature in an exhalant sample to diagnose, prognose, monitor, treat, or prevent Dirofilaria infection in a subject or any combination thereof.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 13 shows a table demonstrating samples found to be in the highest (negative for D. immitis) and lowest (positive for D. immitis) quartiles from Tables 5-8. Columns and rows are organized low to high. The medium gray shading with white lettering indicates that the sample can be found in both the highest and lowest quartiles (for different features). The black shading with white lettering indicates that the sample can be found only in the highest quartiles. The lightest gray shading with black lettering indicates that the sample can be found only in the lowest quartiles. The white with black lettering indicates a sample was only found a single time.

Figure 1:
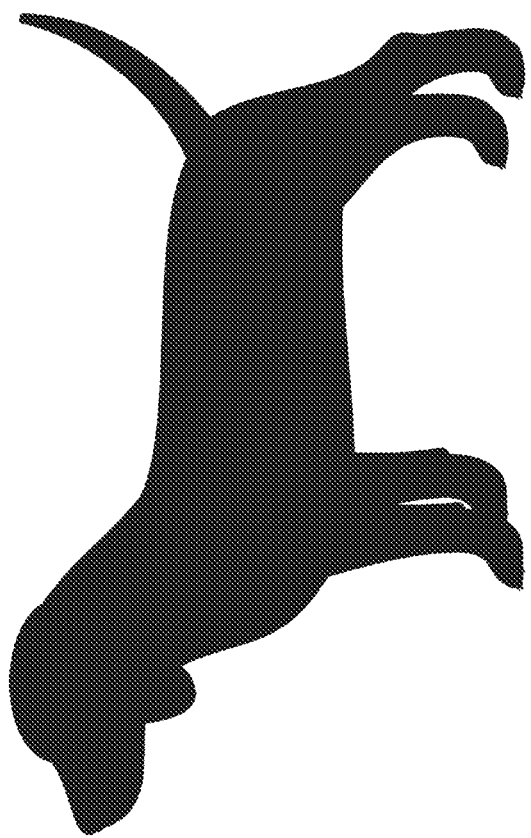
FIG. 1 shows an animal exhalant collection device and exhalant storage container suitable for volatile organic compounds (VOCs) collection and analysis that in some embodiments is used for collection of canine exhalant for VOC analysis.
Figure 1:
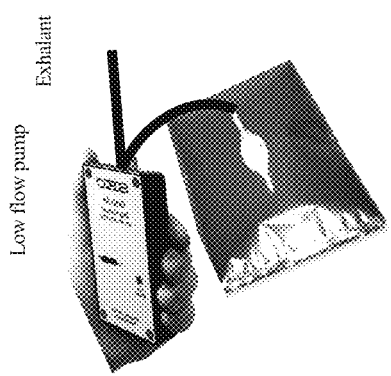

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'". The recitation of numerical ranges by endpoints includes all numbers and fractions subsumed within the respective ranges, as well as the recited endpoints.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4$^{th}$ edition (2012) (Green and Sambrook);

Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosed invention. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated, subject being treated, and/or agent(s) being administered.

As used herein, "anti-infective" refers to compounds or molecules that can either kill an infectious agent and/or modulate or inhibit its activity, infectivity, replication, and/or spreading such that its infectivity is reduced or eliminated and/or the disease or symptom thereof that it is associated is less severe or eliminated. Anti-infectives include, but are not limited to, antibiotics, antibacterials, antifungals, antivirals, anthelmintics, and antiprotozoals.

As used herein, "exhalant" refers to the liquid, vapor, and gasses that are emitted from an organism from the lungs and out an orifice, typically the mouth and nose/nostrils, of the organism. The term "exhalant" is used interchangeably herein with "breath".

The term "optional" or "optionally" means that the subsequent described event, circumstance or substituent may or may not occur, and that the description includes instances where the event or circumstance occurs and instances where it does not.

As used herein, a "biological sample" refers to a sample that is of biologic origin or contains biologic elements. A biologic sample can contain whole cells (live or dead), parts of cells, cell debris, cell products (either intracellular cell products or those that are secreted or excreted from a cell), compounds produced by a biologic entity or cell(s) thereof. The biological sample can be, contain, or be derived from a "bodily fluid" or "bodily gas". The term "bodily fluid" refers to any fluid produced by a biologic entity or subject and includes, amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit, exhalant (respiratory), and mixtures of one or more thereof. Biologic gasses include, but are not limited to exhalant (respiratory), flatulence, decomposition gasses, and the like. Biological samples include cell cultures, bodily fluids, cell cultures from bodily fluids. Bodily fluids, gasses, or other biological samples can be obtained by any suitable collection method and/or technique, including but not limited to, those described in greater detail elsewhere herein, biopsy, puncturing (e.g., venous puncture), swabbing, scraping, plucking, pinching, cutting, catching (e.g., free catching urine or saliva after spitting by a subject), scooping, squeezing, expressing, extracting, sucking, passive sampling, and combinations thereof. Biologic samples can also those obtained from the environment, but contain cells or cell products secreted, released, or excreted from a subject.

As used herein, "cell identity" is the outcome of the instantaneous intersection of all factors that affect it. Wagner et al., 2016. Nat Biotechnol. 34(111): 1145-1160. A cell's identity can be affected by temporal and/or spatial elements. A cell's identity is also affected by its spatial context that includes the cell's absolute location, defined as its position in the tissue (for example, the location of a cell along the dorsal ventral axis determines its exposure to a morphogen gradient), and the cell's neighborhood, which is the identity of neighboring cells. The cell's identity is manifested in its molecular contents. Genomic experiments measure these in molecular profiles, and computational methods infer information on the cell's identity from the measured molecular profiles (inevitably, the molecular profile also reflects allele-intrinsic and technical variation that must be handled properly by computational methods before any analysis is done). This is referred to herein as inferring facets of the cell's identity (or the factors that created it) to stress that none describes it fully, but each is an important, distinguishable aspect. The facets relate to vectors that span the space of cell identities Computational analysis methods can be used of finds such basis vectors directly (Wagner et al., 2016).

As used herein, "cell type" refers to the more permanent aspects (e.g., a hepatocyte typically can't on its own turn into a neuron) of a cell's identity. Cell type can be thought of as the permanent characteristic profile or phenotype of a cell. Cell types are often organized in a hierarchical taxonomy, types may be further divided into finer subtypes; such taxonomies are often related to a cell fate map, which reflect key steps in differentiation or other points along a development process. Wagner et al., 2016. Nat Biotechnol. 34(111): 1145-1160.

As used herein, "cell state" are used to describe transient elements of a cell's identity. Cell state can be thought of as the transient characteristic profile or phenotype of a cell. Cell states arise transiently during time-dependent processes, either in a temporal progression that is unidirectional (e.g., during differentiation, or following an environmental stimulus) or in a state vacillation that is not necessarily unidirectional and in which the cell may return to the origin state. Vacillating processes can be oscillatory (e.g., cell-cycle or circadian rhythm) or can transition between states with no predefined order (e.g., due to stochastic, or environmentally controlled, molecular events). These time-dependent processes may occur transiently within a stable cell type (as in a transient environmental response), or may lead to a new, distinct type (as in differentiation). Wagner et al., 2016. Nat Biotechnol. 34(111): 1145-1160.

As used herein, "cellular phenotype" refers to the configuration of observable traits in a single cell or a population of cells.

As used herein, "concentrated" and "enriched" when used in connection with refers to one or more compound(s) or molecule(s) or population thereof, including but not limited to a polynucleotide, peptide, polypeptide, protein, antibody, or fragments thereof, a metabolite, VOC, or other compound, that is distinguishable from its naturally occurring counterpart in that the concentration or number of molecules/compounds per volume is greater than that of its naturally occurring counterpart or as it would exist in its native or natural state.

As used herein, the terms "disease" or "disorder" are used interchangeably throughout this specification, and refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, indisposition, or affliction.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins. In some instances, "expression" can also be a reflection of the stability of a given RNA. For example, when one measures RNA, depending on the method of detection and/or quantification of the RNA as well as other techniques used in conjunction with RNA detection and/or quantification, it can be that increased/decreased RNA transcript levels are the result of increased/decreased transcription and/or increased/decreased stability and/or degradation of the RNA transcript. One of ordinary skill in the art will appreciate these techniques and the relation "expression" in these various contexts to the underlying biological mechanisms.

As used herein, "infection" as used herein refers to presence of an infective agent, such as a pathogen, e.g., a microorganism or a parasite in or on a subject, which, if its presence or growth were inhibited, would result in a benefit to the subject. Hence, the term refers to the state produced by the establishment, more particularly invasion and multiplication, of an infective agent, such as a pathogen, e.g., a microorganism, in or on a suitable host. An infection may produce tissue injury and progress to overt disease through a variety of cellular and toxic mechanisms.

The term "lipophilic", as used herein, refers to compounds having an affinity for lipids.

As used herein, "marker" is a term of art and commonly broadly denotes a biological molecule or compound, more particularly an endogenous or endogenously produced biological molecule compound, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype, genotype, condition, state, and/or status (e.g. a health, nutritional, physiologic, psychologic, disease state, status, and/or phenotype, The terms "marker" and "biomarker" are be used interchangeably throughout this specification. A marker can be a single molecule and/or compound or can be composed of two or more molecules and/or compounds and thus can also be portrayed herein as a signature.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight (Mw) as opposed to the number-average molecular weight (Ma). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "non-human mammal" or "non-human animal" refers to any mammal (or animal) that is not a human.

As used herein, "organism" refers to any animal, plant, or single-celled life form. An organism can be a subject.

As used herein, "pathogen antigen" refers to an antigen of a biological entity that is pathogenic to a subject, hence, capable of causing a pathological condition or disease in the subject. Pathogens encompass pathogenic microorganisms, such as any pathogenic type of bacterium (including archaebacteria and eubacteria), protozoum, fungus (including molds and yeasts), viroid and virus; as well as single-cell and multicellular parasites, e.g., helminths (e.g., cestodes, nematodes and trematodes). The term also encompasses biological entities, which display pathogenicity in immunocompromised hosts, but may not ordinarily be pathogenic in a non-immunocompromised host.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, a "population" of cells is any number of cells greater than 1, but is preferably at least $1 \times 10^3$ cells, at least $1 \times 10^4$ cells, at least at least $1 \times 10^5$ cells, at least $1 \times 10^6$ cells, at least $1 \times 10^7$ cells, at least $1 \times 10^8$ cells, at least $1 \times 10^9$ cells, or at least $1 \times 10^{10}$ cells.

As used herein, "positive control" refers to a "control" that is designed to produce the desired result, provided that all reagents are functioning properly and that the experiment is properly conducted.

As used herein, "preventive" and "prevent" refers to hindering or stopping a disease or condition before it occurs, even if undiagnosed, or while the disease or condition is still in the sub-clinical phase.

As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type and/or specific cell state.

The terms "subject," "individual," and "patient" are used interchangeably herein to refer to a vertebrate, preferably a mammal, more preferably a canine or human. Mammals include, but are not limited to, murines, simians, humans, canines, farm animals, sport animals, and/or pets. "Subject" includes animals of the genus *Canis, Felis, Lynx, Mustela, Procyon*, or *Vulpes* Tissues, cells and their progeny of a biological entity obtained in vivo or cultured in vitro are also encompassed within the term "subject".

As used herein, the term "signature" can encompass any gene or genes, protein or proteins, epigenetic element(s), metabolite(s), compound(s), and/or other cell products (e.g., exosomes, vesicles, phages, viruses, virus like particles, etc.) produced, excreted, secreted, or otherwise released by a subject, whose expression, production, secretion, excretion, and/or release profile or whose occurrence is associated with a specific cell type, subtype, or cell state of a specific cell type or subtype within a population of cells, and/or health, disease, infection, biological, nutritional, physiological, psychological, or any combination thereof, state and/or status of a subject. Levels and/or amounts of expression, production, excretion, secretion, release, and/or activity and/or prevalence of any of the gene(s), protein(s), metabolite(s), compound(s), and/or other cell product(s) can be compared between different cells or cell populations, subject states and/or status, or any combination thereof in order to characterize or identify, for instance, signatures specific for cell (sub)populations, (sub)types, (sub)states and/or subject (sub)states, (sub)status, and/or subject population stratification based thereon. Increased or decreased expression, production, excretion, secretion, release, and/or activity and/or prevalence of signature gene(s), protein(s), epigenetic element(s), metabolite(s), compound(s) and/or other cell product(s) can be compared between different cells, cell populations, and/or subjects in order to characterize or identify, for instance, specific cell (sub)populations, (sub)types, (sub) states and/or subject (sub)states, (sub)status, and/or subject population stratification. The detection of a signature in or of single cells can be used to identify qualitatively and/or quantitate, for instance, specific cell (sub)populations, (sub) types, and/or (sub)states. A signature can include a gene or genes, protein or proteins, epigenetic element(s), metabolite(s), compounds, and/or other cell products whose expression or occurrence is specific to a cell (sub)population, (sub)type, (sub)state, and/or health, disease, infection, biological, nutritional, physiological, psychological, or any combination thereof, state and/or status of a subject, such that expression or occurrence is exclusive to the cell (sub) population. The amount, level, expression, activity, or any combination of any one or more elements (e.g., gene, protein, compound, metabolite, etc.) signature can be increased or decreased in one state, type, status, patient population, etc. as compared to another state, type, status, patient population, control, and/or threshold value and thus can uniquely identify one state, type status, patient population from one or more other state, type, status, and/or patient population.

A metabolite signature or a compound signature (such as a volatile organic compound signature) as the terms are used herein thus refer to a signature that is composed completely of or in at least part by one or more metabolites or compounds (such as one or more VOCs, for example). The amount, level, expression, activity, or any combination of any one or more metabolites or compounds in a metabolite or compound signature can be increased or decreased in one state, type, status, patient population, etc. as compared to another state, type, status, patient population, control, and/or threshold value and thus can uniquely identify one state, type status, patient population from one or more other state, type, status, and/or patient population. A metabolite signature or compound signature is thus a signature composed of one or more metabolite(s)s or other compound(s) and can thus refer to any set of increased and decreased (e.g., in level, amount, activity, particular state, etc.) metabolite(s) or other compound(s) produced, released, excreted, and/or secreted by one or more cells, tissues, organs, or any combination thereof of a subject that are uniquely representative of a cell (sub)population, (sub)type, (sub)state, and/or health, disease, infection, biological, nutritional, physiological, psychological, or any combination thereof, state and/or status of a subject. Such a signature can be derived from a sampled profile of the amount, level, and/or activity level of metabolites or other compound(s) in a sample, such as a biologic sample, from the subject. A signature can be composed of any number of features (e.g., genes, proteins, epigenetic elements, metabolite(s), compound(s), and/or other cell products (e.g., exosomes, vesicles, phages, viruses, virus like particles, etc.) expressed, produced, excreted, secreted, and/or otherwise released by a subject (e.g., 1-100, 1,000, 10,000 or more). For example, a signature can include a list of features differentially expressed, produced, excreted, secreted, and/or otherwise released in a particular state or status (e.g., health or disease) of interest. The signature can be composed completely of or contain at least in part 1, 2, 3, 4, 5, 6, 7, 8, 9, 10, 11, 12, 13, 14, 15, 16, 17, 18, 19, or 20 or more features. In some embodiments, the signature can be composed completely of or contain at least in part 1-2 or more, 1-3 or more, 1-4 or more, 1-5 or more, 1-6 or more, 1-7 or more, 1-8 or more, 1-9 or more, 1-10 or more, 2-3 or more, 2-4 or more, 2-5 or more, 2-6 or more, 2-7 or more, 2-8 or more, 2-9 or more, 2-10 or more, 3-4 or more, 3-5 or more, 3-6 or more, 3-7 or more, 3-8 or more, 3-9 or more, 3-10 or more, 4-5 or more, 4-6 or more, 4-7 or more, 4-8 or more, 4-9 or more, 4-10 or more, 5-6 or more, 5-7 or more, 5-8 or more, 5-9 or more, 5-10 or more, 6-7 or more, 6-8 or more, 6-9 or more, 6-10 or more, 7-8 or more, 7-9 or more, 7-10 or more, 8-9 or more, 8-10 or more, 9-10 or more, 1-20 or more, 2-20 or more, 3-20 or more, 4-20 or more, 5-20 or more, 6-20 or more, 7-20 or more, 8-20 or more, 9-20 or more, 10-20 or more, 11-20 or more, 12-20 or more, 13-20 or more, 14-20 or more, 15-20 or more, 16-20 or more, 17-20 or more, 18-20 or more, 19-20 or more, or 20 or more features (e.g. metabolites or compounds, such as VOCs).

As used herein, "substantial" and "substantially," specify an amount of between 95% and 100%, inclusive, between 96% and 100%, inclusive, between 97% and 100%, inclusive, between 98% 100%, inclusive, or between 99% 100%, inclusive.

As used herein, "substantially free" can mean an object species is present at non-detectable or trace levels so as not to interfere with the properties of a composition or process.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g., mass, volume, dosage, concentration, and/or time period) needed to achieve one or more desired result(s). For example, a therapeutically effective amount refers to an amount needed to achieve one or more therapeutic effects.

A "suitable control" is a control that will be instantly appreciated by one of ordinary skill in the art as one that is included such that it can be determined if the variable being evaluated an effect, such as a desired effect or hypothesized effect. One of ordinary skill in the art will also instantly appreciate based on inter alia, the context, the variable(s), the desired or hypothesized effect, what is a suitable or an appropriate control needed.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g., a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, a "threshold value" refers to a defined value in suitable unit of measure that can be empirically determined and/or verified, statistically determined and/or verified, clinically determined and/or verified, and is a value that is used to discriminate statistics, experimental values, test values, candidate values, subject value, sample values, and the like that are above or below the threshold value. A threshold value, can in some embodiments, be a limit value, such that all values or statistics that are above, in the case of an upper threshold limit value, are rejected and/or are indicative of a condition, state, type, and/or all values or statistics that are below, in the case of the lower threshold limit value, are rejected and/or are indicative of a condition, state, type. An upper and lower threshold limit together can form a threshold range where value that lie within the upper and the lower threshold limits are accepted. It will be appreciated that, depending on context (e.g., assay, compound within an assay or signature, etc. subject age, etc.) (which will be appreciated by the description herein and by one of ordinary skill in the art), values corresponding to e.g., a diseased (e.g., a Dirofilarial infection) condition or state can fall above or below a threshold value. In a signature, such as the Dirofilarial infection signature described herein, different compounds can each have their own threshold values, some of which may be above and some of which may be below their respective values within the signature that is indicative of Dirofilarial infection and non-infection and/or can discriminate between Dirofilaria infected subjects and non-infected subjects. A threshold value in some embodiments is quantitative. In some embodiments, a threshold value is qualitative.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as infection with a dirofilarial organism (e.g., Dirofilaria spp., Dirofilaria sp.) (of any stage) (including, but not limited to, Dirofilaria *immitis*, Dirofilaria *repens*, Dirofilaria *tenuis*, Dirofilaria *ursi*, D. subdermata, *D. striata*, or a *D. hongkongensis*) or have the condition known as dirofilariasis. The effect can be therapeutic in terms of a partial or complete cure of a disease, condition, symptom or adverse effect attributed to the disease, disorder, or condition. The term "treatment" as used herein covers any treatment of dirofilarial infection or dirofilariasis, in a subject, particularly a human and/or canine (domesticated or not) and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "volatile organic compound (VOC)" refers to any compound that includes carbon that readily produce vapors at ambient temperatures, and have strong tendency to vaporize from solids and liquids into gasses. In the context of the present embodiments, VOC refers to those VOCs that are produced by a cell of a subject or an organism or microorganism living within a subject (e.g., a bacterium, parasite (e.g., a worm), yeast, and the like). Such VOCs are generally small (e.g., containing 15 or less carbon atoms) and have a low molecular mass (e.g., less than about 300 Da), a high vapor pressure, and low boiling point, and optionally a lipophilic moiety. Non-limiting, exemplary VOCs include alkenes, alcohols, ketones, benzenoids, pyrazines, sulfides, and terpenes. In some embodiments, VOCs can be metabolites.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt. % values the specified components in the disclosed composition or formulation are equal to 100.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Heartworm infection and the resulting disease caused by adult stage worms in dogs is a significant and serious, yet preventable, disease primarily affecting dogs. However, other hosts can be affected as well such as cats, ferrets, and other organisms including other mammals, such as wolves, coyotes, foxes, sea lions and—in rare instances—humans. In humans, Dirofilaria infection can be divided into pulmonary (adult worms primarily affect the lungs and hearts—similar to heartworm infection in dogs and caused by *D. immitis*) and subcutaneous (adult worms primarily affect the subcutaneous tissues—caused by Dirofilaria species of the subgenus Nochtiella). Heartworm disease is caused by adult *D. immitis* that live in the heart, lungs, and associated blood vessels, which can reach up to a foot long or more in length. This can result in severe lung disease, heart failure, and damage to other organs in the affected organism.

Dogs are a natural host for *D. immitis*. As such, heartworms that live inside of dogs mature into adults, mate, and produce offspring. If left untreated, their numbers increase and ultimately (no matter the number) can cause permanent damage to the heart, lungs, and associated arteries and negatively impact the dog's health and quality of life long after the parasites are gone. Prevention is the best way to control heartworm disease and identification and treatment of positive dogs complements this approach. As such, effective, and desirably, early identification of infected dogs, particularly those harboring adult stage worms, is an important piece of the strategy to treat and prevent heartworm disease in dogs. For other animals such as cats and ferrets, where there is no approved treatment, prevention is imperative. However, even in these animals testing and particularly early identification, of infection can allow for supportive care to be employed and potentially saving the animal's life.

Like most parasites, heartworms complete their life cycle in multiple hosts/vectors. The mosquito (from several genera, including *Aedes, Culex, Anopheles, Psorophora, Ochlerotatus*, and *Mansonia*) is a required vector in the heartworm life cycle. Adult female heartworms living in an infected dog, fox, coyote, or wolf produce microscopic baby worms called microfilariae that circulate in the blood stream. The first heartworm detection methods were blood smears that would allow for identification of any circulating microfilariae. Because of the high rate of false negatives using this method and/or as preventives are generally effective against this stage of the heartworms this method of heartworm detection is typically only used as a secondary validation to the circulating antigen tests previously discussed where such tests are available. When a mosquito bites and takes a blood meal from an infected animal, the mosquito picks up circulating microfilariae, which then develop and mature into "infective stage" larvae over a period of 10 to 14 days within the mosquito. Then, when the infected mosquito bites another dog, cat, or other susceptible organism, the infective larvae are deposited onto the surface of the organism's skin and enter the new host through the mosquito's bite wound. Once inside a new host, it takes approximately 6-7 months for the larvae to develop into sexually mature adult heart worms. Once mature, heartworms can live for five to seven years in dogs and up to two to three years in cats. Because of the longevity of these worms, each mosquito season can lead to an increasing number of worms in an infected pet. Indeed, there have been some non-treated dogs where the adult worm burden was observed to be in the hundreds. Severity of clinical signs is typically, but not always, positively correlated with the worm load. However, if there are other medical conditions (heart defects, cancers, other co-morbidities, advanced age, etc.) a low worm burden may lead to severe clinical signs.

Routine testing is part of a good heartworm prevention and treatment strategy, particularly for dogs. Since it takes 6-7 months for the larvae to reach maturity, vets will typically start testing dogs at 6-7 months of age then at yearly intervals after that, depending on e.g., prevention compliance, location, etc. Current clinical tests are based on detection of female heartworm antigen circulating in blood, and is sometimes validated with a microscopic blood analysis to visualize circulating microfilariae. As previously discussed, these tests are not without limitations including, but not limited to, the requirement for a blood sample, which can be challenging for subjects that are not compliant for a blood draw and for personnel that are not skilled in obtaining blood samples from animals.

With the limitations of current heartworm tests in mind, embodiments disclosed herein describe Dirofilaria exhalant signatures and methods of using said signatures to non-invasively discriminate Dirofilaria infected, animals from non-infected animals. The Dirofilaria exhalant signatures include one or more volatile organic compounds (VOCs). In some embodiments, the Dirofilaria exhalant signatures discriminate between animals infected with adult stage *D. immitis* and non-infected subjects. Also provided herein are devices for animal, such as a dog, exhalant sample collection for Dirofilaria exhalant signature analysis as described herein. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Dirofilaria Exhalent Signature

Described in the example embodiments herein are Dirofilaria exhalant signatures that include one or more volatile organic compound (VOC) and can, in some embodiments, be used to separate and/or identify Dirofilaria infected subjects and non-infected (or no antigen detected) subjects. In some embodiments, the Dirofilaria exhalant signature and is composed of one or more VOCs in the exhalant of a subject. In some embodiments, the Dirofilaria exhalant signature is a *D. immitis* exhalant signature, Dirofilaria *repens* exhalant signature, Dirofilaria *tenuis* exhalant signature, Dirofilaria *ursi* exhalant signature, D. subdermata exhalant signature, *D. striata* exhalant signature, or a *D. hongkongensis* exhalant signature. In some embodiments, the presence or absence of and/or a change (e.g., either increase or decrease) in the amount of one or more of the VOCs in the Dirofilaria exhalant signature indicates Dirofilarial infection or non-infection in the subject from which the exhalant was obtained. In some embodiments, the presence or absence of and/or a change (e.g., either increase or decrease) in the amount of one or more of the VOCs in the *D. immitis* exhalant signature, Dirofilaria *repens* exhalant signature, Dirofilaria *tenuis* exhalant signature, Dirofilaria *ursi* exhalant signature, D. subdermata exhalant signature, *D. striata* exhalant signature, or a *D. hongkongensis* exhalant signature indicates *D. immitis, D. repens, D. tenuis, D. ursi*, D. subdermata, *D. striata*, or a *D. hongkongensis* infection or non-infection in the subject from which the exhalant was obtained.

In some embodiments, the Dirofilaria exhalant signature is or includes one or more one or more volatile organic compounds (VOCs) selected from the group of an aromatic hydrocarbon, a monoterpene, an alkyl alcohol, a cyclopentanone, an aziridine, an alkane hydrocarbon, a phenol, a ketone, and combinations thereof. In some embodiments, the number of VOCs in the Dirofilaria exhalant signature is 1, 2, 3, 4, 5, 6, 7, 8, 9, 10, 11, 12, 13, 15, or 15.

In some embodiments, the Dirofilaria exhalant signature is or includes one or more one or more volatile organic compounds (VOCs) selected from the group of an aromatic hydrocarbon, a monoterpene, an alkyl alcohol, a cyclopentanone, an aziridine, an alkane hydrocarbon, a phenol, a ketone, and combinations thereof. In some embodiments, the number of VOCs in the Dirofilaria exhalant signature is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, or more.

In some embodiments, the Dirofilaria exhalant signature is composed of nine VOCs, wherein the nine VOCs are an aromatic hydrocarbon, a monoterpene, an alkyl alcohol, a cyclopentanone, an aziridine, two alkane hydrocarbons, a phenol, and a ketone. In some embodiments, the aromatic hydrocarbon is ortho xylene. In some embodiments, the monoterpene is p-Menthane-1,2,3-triol. In some embodiments, the alkyl alcohol is 3,7,11-trimethyl-1-Dodecanol. In some embodiments, the cyclopentanone is 2-ethyl-Cyclohexanone. In some embodiments, the aziridine is 2-mehtyl-2-(2,2,4,4,6,6,-hexamethylheptyl)-Aziridine. In some embodiments, the alkane hydrocarbon is 1,2,3,6,7,8,8a,8b-octahydro-, trans-Biphenylene, 2,6,10-trimethyl-Tetradecane, or both, In some embodiments, the phenol is 5,6,6-Trimethyl-5-(3-oxobut-1-enyl)-1-oxaspiro[2.5]octan-4-one. In some embodiments, the ketone is 5,5-Dibutylnonane. In some embodiments, the Dirofilaria exhalant signature is composed entirely of ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3, 6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-One, and 5,5-Dibutylnonane. In some embodiments, the Dirofilaria exhalant signature is composed of at least ortho xylene, p-Methane-1,2,3-triol, 3,7,11-trimethyl-1-Dodecanol, 2-ethyl-Cyclohexanone, 2-mehtyl-2-(2, 2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-One, and 5,5-Dibutylnonane.

In some embodiments, the Dirofilaria exhalant signature is composed of four or more VOCs selected from a monoterpene, a cyclopentanone, an aziridine, and an alkane hydrocarbon. In some embodiments the signature is composed of a monoterpene, a cyclopentanone, an aziridine, and an alkane hydrocarbon. In some embodiments, the Dirofilaria exhalant signature is composed of at least a monoterpene, a cyclopentanone, an aziridine, and an alkane hydrocarbon. In some embodiments, the monoterpene is p-Methane-1,2,3-triol. In some embodiments, the cyclopentanone is 2-ethyl-Cyclohexanone. In some embodiments, the aziridine is 2-mehtyl-2-(2,2,4,4,6,6-hexamethylheptyl)-Aziridine. In some embodiments, the alkane hydrocarbon is 1,2,3,6,7,8, 8a,8b-octahydro, trans-Biphenylene. In some embodiments, the Dirofilaria exhalant signature is composed of at least p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene. In some embodiments, the Dirofilaria exhalant signature is p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene.

In some embodiments, the Dirofilaria exhalant signature is composed of one or more VOCs selected from: p-Methane-1,2,3-triol, 2-ethyl-Cyclohexanone, 2-mehtyl-2-(2,2,4, 4,6,6-hexamethylheptyl)-Aziridine, 1,2,3,6,7,8,8a,8b-octahydro, and trans-Biphenylene.

In some embodiments, the Dirofilaria exhalant signature is composed of one or more VOCs selected from: ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1, 1,3-trimethyl-Cylcohexane, Tricyclo[4.3.1.1<2,5>]undec-3 en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; and 7-propyl-Tridecane. In some embodiments, the Dirofilaria exhalant signature is composed of ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a, 8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane; 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3 en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; and 7-propyl-Tridecane.

In some embodiments, the *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature is composed of one or more VOCs selected from: ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a, 8b-octahydro, trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

In some embodiments, the *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature is composed of ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; and 7-propyl-Tridecane.

In some embodiments, the *D. immitis* exhalant signature, Dirofilaria *repens* exhalant signature, Dirofilaria *tenuis* exhalant signature, Dirofilaria *ursi* exhalant signature, D. subdermata exhalant signature, *D. striata* exhalant signature, or the *D. hongkongensis* exhalant signature is composed of ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

In some embodiments, the Dirofilaria signature is a *D. immitis* signature and is composed of ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

In some embodiments, the *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature is composed of four or more VOCs selected from a monoterpene, a cyclopentanone, an aziridine, and an alkane hydrocarbon. In some embodiments the signature is composed of a monoterpene, a cyclopentanone, an aziridine, and an alkane hydrocarbon. In some embodiments, the *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature is composed of at least a monoterpene, a cyclopentanone, an aziridine, and an alkane hydrocarbon. In some embodiments, the monoterpene is p-Methane-1,2,3-triol. In some embodiments, the cyclopentanone is 2-ethyl-Cyclohexanone. In some embodiments, the aziridine is 2-mehtyl-2-(2,2,4,4,6,6-hexamethylheptyl)-Aziridine. In some embodiments, the alkane hydrocarbon is 1,2,3,6,7,8,8a,8b-octahydro, trans-Biphenylene. In some embodiments, the *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature is composed of at least p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene. In some embodiments, the *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature is p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene.

In some embodiments, the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) includes one or more VOCs identified and shown in Table 9. In some embodiments, one or more VOCs identified and shown in Table 9 are increased and/or decreased in the exhalant of a subject infected with Dirofilaria sp. or spp. (e.g., *D. immitis, D. repens, D. tenuis, D. ursi*, D. subdermata, *D. striata*, or a *D. hongkongensis*).

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are present in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are present in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2, 5>]undec-3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are absent in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are absent in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a, 8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2, 5>]undec-3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are present in the exhalant of a subject with a Dirofilaria infection (e.g., a *D. immitis, D.*

*repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are present in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4, 6,6-hexamethylheptyl)-Aziridine, 1,2,3,6,7,8,8a,8b-octahydro, trans-Biphenylene, 2,6,10-trimethyl-tetradecane, 5,6, 6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3 en-10-ol, 10-methyl-, stereoisomer; 5,6,7,8,9, 10-Hexahydrobenzocyclooctene; 1,2,3,6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are absent in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are absent in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4, 6,6-hexamethylheptyl)-Aziridine, 1,2,3,6,7,8,8a, 8b-octahydro, trans-Biphenylene, 2,6,10-trimethyl-tetradecane, 5,6, 6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2, 5>]undec-3en-10-ol, 10-methyl-, stereoisomer; 5,6,7,8,9, 10-Hexahydrobenzocyclooctene; 1,2,3,6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are decreased and/or are present below a threshold value in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are decreased and/or are present below a threshold value in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a, 8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are increased and/or are present above a threshold value in the exhalant of a subject without a Dirofilaria infection (e.g., a *D. immitis, D. repens, D. tenuis, D. ursi*, D. subdermata, *D. striata*, or a *D. hongkongensis* infection) as compared to exhalant of a subject having a Dirofilaria infection, infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are increased and/or are present above a threshold value in the exhalant of a subject without a Dirofilaria infection as compared to exhalant of a subject not having a Dirofilaria infection, infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3, 6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3en-10-ol, 10-methyl-, stereoisomer; 5,6,7,8,9,10-Hexahydrobenzocyclooctene; 1,2,3, 6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are increased and/or are present above a threshold value in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are increased and/or are present above a threshold value in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are decreased and/or are present below a threshold value in the exhalant of a subject without a Dirofilaria infection (e.g., a *D. immitis, D. repens, D. tenuis, D. ursi*, D. subdermata, *D. striata*, or a *D. hongkongensis* infection) as compared to exhalant of a subject having a Dirofilaria infection, infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are decreased and/or are present below a threshold value in the exhalant of a subject without a Dirofilaria infection as compared to exhalant of a subject not having a Dirofilaria infection, infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; 7-propyl-Tridecane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are present in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are present in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are absent in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are absent in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are present in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are present in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are absent in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are absent in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are decreased and/or are present below a threshold value in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are decreased and/or are present below a threshold value in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-One, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are increased and/or are present above a threshold value in the exhalant of a subject without a Dirofilaria infection (e.g., a *D. immitis, D. repens, D. tenuis, D. ursi*, D. subdermata, *D. striata*, or a *D. hongkongensis* infection) as compared to exhalant of a subject having a Dirofilaria infection, infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are increased and/or are present above a threshold value in the exhalant of a subject without a Dirofilaria infection as compared to exhalant of a subject not having a Dirofilaria infection, infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-One, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are increased and/or are present above a threshold value in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are increased and/or are present above a threshold value in the exhalant of a subject with a Dirofilaria infection as compared to exhalant of a subject not having a Dirofilaria infection, non-infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-One, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are decreased and/or are present below a threshold value in the exhalant of a subject without a Dirofilaria infection (e.g., a *D. immitis, D. repens, D. tenuis, D. ursi*, D. subdermata, *D. striata*, or a *D. hongkongensis* infection) as compared to exhalant of a subject having a Dirofilaria infection, infected control, or other suitable control, are an aromatic hydrocarbon, a monoterpene, an alkyl alcohol, a cyclopentene, an aziridine, an alkane hydrocarbon, a phenol, a ketone, or any combination thereof. In some embodiments, the VOC(s) in the Dirofilaria exhalant signature that is/are decreased and/or are present below a threshold value in the exhalant of a subject without a Dirofilaria infection as compared to exhalant of a subject not having a Dirofilaria infection, infected control, or other suitable control is/are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-One, 5,5-Dibutylnonane, and any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are present in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are a monoterpene, a cyclopentene, an aziridine, an alkane hydrocarbon, or any combination thereof. In some embodiments, the VOC(s) in the Dirofilaria exhalant signature that is/are present in the exhalant of a subject with a Dirofilaria infection as compared to exhalant of a subject not having a Dirofilaria infection, non-infected control, or other suitable control is/are p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, or any combination thereof.

In some embodiments, the VOC(s) in the Dirofilaria exhalant signature (e.g., *D. immitis* exhalant signature, *D. repens* exhalant signature, *D. tenuis* exhalant signature, *D.*

*ursi* exhalant signature, D. subdermata exhalant signature, *D. striata* exhalant signature, or the *D. hongkongensis* exhalant signature) that is/are absent in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are a monoterpene, a cyclopentene, an aziridine, an alkane hydrocarbon, or any combination thereof. In some embodiments, the VOC(s) in the Dirofilaria exhalant signature that is/are absent in the exhalant of a subject with a Dirofilaria infection as compared to exhalant of a subject not having a Dirofilaria infection, non-infected control, or other suitable control is/are p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, or any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are present in the exhalant of a subject without a Dirofilaria infection (e.g., a *D. immitis, D. repens, D. tenuis, D. ursi*, D. subdermata, *D. striata*, or a *D. hongkongensis* infection) as compared to exhalant of a subject having a Dirofilaria infection, infected control, or other suitable control, are a monoterpene, a cyclopentene, an aziridine, an alkane hydrocarbon, or any combination thereof. In some embodiments, the VOC(s) in the Dirofilaria exhalant signature that is/are absent in the exhalant of a subject without a Dirofilaria infection as compared to exhalant of a subject having a Dirofilaria infection, infected control, or other suitable control is/are p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, or any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are absent in the exhalant of a subject without a Dirofilaria infection (e.g., a *D. immitis, D. repens, D. tenuis, D. ursi*, D. subdermata, *D. striata*, or a *D. hongkongensis* infection) as compared to exhalant of a subject having a Dirofilaria infection, infected control, or other suitable control, are a monoterpene, a cyclopentene, an aziridine, an alkane hydrocarbon, or any combination thereof. In some embodiments, the VOC(s) in the Dirofilaria exhalant signature that is/are absent in the exhalant of a subject without a Dirofilaria infection as compared to exhalant of a subject having a Dirofilaria infection, infected control, or other suitable control is/are p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, or any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are decreased and/or are present below a threshold value in the exhalant of a subject with a Dirofilaria infection (e.g., a *D. immitis, D. repens, D. tenuis, D. ursi*, D. subdermata, *D. striata*, or a *D. hongkongensis* infection) as compared to exhalant of a subject not having a Dirofilaria infection, non-infected control, or other suitable control, are a monoterpene, a cyclopentene, an aziridine, an alkane hydrocarbon, or any combination thereof. In some embodiments, the VOC(s) in the Dirofilaria exhalant signature that is/are decreased and/or are present below a threshold value in the exhalant of a subject with a Dirofilaria infection as compared to exhalant of a subject not having a Dirofilaria infection, non-infected control, or other suitable control is/are p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, or any combination thereof.

In some embodiments, the VOC(s) in the Dirofilaria exhalant signature (e.g., *D. immitis* exhalant signature, *D. repens* exhalant signature, *D. tenuis* exhalant signature, *D. ursi* exhalant signature, D. subdermata exhalant signature, *D. striata* exhalant signature, or the *D. hongkongensis* exhalant signature) that is/are increased and/or are present above a threshold value in the exhalant of a subject without a Dirofilaria infection (e.g., a *D. immitis, D. repens, D. tenuis, D. ursi*, D. subdermata, *D. striata*, or a *D. hongkongensis* infection) as compared to exhalant of a subject having a Dirofilaria infection, infected control, or other suitable control, are a monoterpene, a cyclopentene, an aziridine, an alkane hydrocarbon, or any combination thereof. In some embodiments, the VOC(s) in the Dirofilaria exhalant signature that is/are increased and/or are present above a threshold value in the exhalant of a subject without a Dirofilaria infection as compared to exhalant of a subject having a Dirofilaria infection, infected control, or other suitable control is/are p-Methane-1,2,3-triol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, or any combination thereof.

Methods and techniques of detecting a Dirofilaria exhalant and using it to diagnose prognose, and/or stage a Dirofilaria infection in a subject are described in greater detail elsewhere herein.

Methods of Detecting Dirofilaria Infection

Described herein are methods of identifying subjects infected with one or more life stages of a species of Dirofilaria, such as *D. immitis, D. repens, D. tenuis, D. ursi*, D. subdermata, *D. striata*, or *D. hongkongensis*. In some embodiments, the subject is a host or a vector of one or more Dirofilaria species. The subject can be a host of *D. immitis, D. repens, D. tenuis, D. ursi*, D. subdermata, *D. striata*, and/or *D. hongkongensis*. In some embodiments, the host is a human or non-human animal. In some embodiments, the non-human animal is an animal in the genus *Canis, Felis, Lynx, Mustela, Procyon*, or *Vulpes*. In some embodiments, the subject is a domestic dog, wolf, fox, bobcat, domestic cat, ferret, raccoon, jackal, coyote, or a domestic cat. In some embodiments, the adult stage of the Dirofilaria is detected.

Generally, the methods of identifying subjects infected with one or more life stages of a species of Dirofilaria includes detecting a Dirofilaria exhalant signature in an exhalant sample from a subject, whereby the Dirofilaria exhalant signature detected indicates Dirofilaria infection and/or stage thereof. Dirofilaria exhalant signatures are described in greater detail elsewhere herein. Generally, exhalant samples can be obtained non-invasively from a subject and VOCs in the sample can be analyzed for the presence of a Dirofilaria exhalant signature of an infected or non-infected individual. The VOCs in an exhalant sample collected from a subject can be analyzed by any suitable method for VOC analysis. Sample analysis can occur at point of collection (e.g., at a vet, animal shelter, zoo, or doctor's office) or can be conducted at a location different than the point of collection (e.g., USDA, CDC, state, or other government testing laboratory, commercial testing laboratory, etc.). In some embodiments, the method qualitatively identifies the presence (or absence) of a Dirofilaria signature specific to infected individuals. In some embodiments, the method qualitatively identifies the presence (or absence) of a Dirofilaria signature specific to non-infected individuals. In some embodiments, the method quantitatively identifies the amount of one or more of the VOCs present in the signature. In some embodiments, quantitative analysis can allow for determination of the load of adult Dirofilaria present in the organism.

The methods described herein can diagnose, prognose, stage, and/or infection with a Dirofilaria. Also described herein are methods of treating and/or preventing Dirofilaria infection in a subject that include a method diagnosing, prognosing, and/or staging Dirofilaria infection based at least in part on a Dirofiliara exhalant signature and treating and/or preventing Dirofilaria infection, particularly the adult stage, in the subject.

The volume of exhalant collected can range from 0.001 mL to 1000 mL. In some embodiments, the volume of exhalant collected is about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or about 1000 mL.

In some embodiments, the volume of exhalant collected ranges from about 0.001 to about 0.01 mL, from about 0.01 to about 0.1 mL, from about 0.1 to about 1 mL, from about 1 to about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or about 1000 mL.

The volume of exhalant collected can be 0.001, 0.002, 0.003, 0.004, 0.005, 0.006, 0.006, 0.007, 0.008, 0.009, 0.1, 0.2, 0.3, 0.4, 0.5, 0.6, 0.7, 0.8, 0.9, 1, 2, 3, or 4 times the average tidal volume for the subject. It will be appreciated that average tidal volume will vary with subject species, age, size, disease state, etc. Devices capable of sample collection (e.g., exhalant from an animal) are described in greater detail elsewhere herein.

Described in some embodiments herein are non-invasive method of diagnosing, prognosing, staging, and/or monitoring Dirofilaria infection in a subject that include the step of detecting a Dirofilaria exhalant signature in an exhalant sample obtained from the subject, wherein the Dirofilaria exhalant signature is as previously described whereby the presence absence of a Dirofilaria exhalant signature is indicative of presence (or absence as the case may be) of infection by one or more stages of a species of Dirofilaria (such as *D. immitis*, *D. repens*, *D. tenuis*, *D. ursi*, *D. subdermata*, *D. striata*, or *D. hongkongensis*).

In some embodiments, the method includes detection of a decrease, increase, or both of one or more of the VOCs of the Dirofilaria exhalant signature as compared to a threshold value, a suitable control, or both, which indicates the presence or absence of Dirofilaria infection in the subject. In some embodiments, the amount of an aromatic hydrocarbon, a monoterpene, a cyclopentanone, an aziridine, an alkane hydrocarbon, a phenol, a ketone, or any combination thereof present in the Dirofilaria exhalant signature is a relative amount. In some embodiments, the amount of the ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane, 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec-3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; and/or 7-propyl-Tridecane in the Dirofilaria exhalant signature is a relative amount. The relative amount of one or more of the VOCs in the Dirofilaria exhalant signature can be determined relative to a suitable control, threshold value(s), and/or total amount of VOCs present in the sample relative to one or more other VOCs in the sample and/or within the Dirofilaria exhalant signature.

In some embodiments, the amount of an aromatic hydrocarbon, a monoterpene, a cyclopentanone, an aziridine, an alkane hydrocarbon, a phenol, a ketone, or any combination thereof present in the Dirofilaria exhalant signature is an absolute amount. In some embodiments, the amount of the ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, 5,5-Dibutylnonane; 1,3-dimethyl-Benzene, 2H-Pyran-2-carboxylic acid, 6-butoxy-3,6-dihydro-, ethyl ester; 2-butyl-1,1,3-trimethyl-Cylcohexane, Tricyclo[4.3.1.1<2,5>]undec- 3en-10-ol, 10-methyl-, stereoisomer; 5,6,7,8,9,10-Hexahydrobenzocyclooctene; 1,2,3,6,7,8,8a,8b-octahydro-, trans-Biphenylene; 2-methyl-Tridecane; and/or 7-propyl-Tridecane in the Dirofilaria exhalant signature is an absolute amount.

In some embodiments, the amount (whether a relative amount or an absolute amount) of one or more of the VOCs in the Dirofilaria exhalant signature in the sample is increased, as compared to a suitable control, threshold value, standard, or a combination thereof, in a Dirofilaria exhalant signature that indicates the subject from which the sample was obtained is infected with one or more stages of Dirofilaria, such as the adult stage. In some embodiments, the amount of one or more of the VOCs in the Dirofilaria exhalant signature is increased 1-5000 percent or more in a Dirofilaria exhalant signature that indicates the subject from which the sample was obtained is infected with one or more stages of Dirofilaria, such as the adult stage. In some embodiments, the amount of one or more of the VOCs in the Dirofilaria exhalant signature is increased 5, 10, 15, 20, 25, 30, 35, 40, 45, 50, 55, 60, 65, 70, 75, 80, 85, 90, 95, 100, 25, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000, 2025, 2050, 2075, 2100, 2125, 2150, 2175, 2200, 2225, 2250, 2275, 2300, 2325, 2350, 2375, 2400, 2425, 2450, 2475, 2500, 2525, 2550, 2575, 2600, 2625, 2650, 2675, 2700, 2725, 2750, 2775, 2800, 2825, 2850, 2875, 2900, 2925, 2950, 2975, 3000, 3025, 3050, 3075, 3100, 3125, 3150, 3175, 3200, 3225, 3250, 3275, 3300, 3325, 3350, 3375, 3400, 3425, 3450, 3475, 3500, 3525, 3550, 3575, 3600, 3625, 3650, 3675, 3700, 3725, 3750, 3775, 3800, 3825, 3850, 3875, 3900, 3925, 3950, 3975, 4000, 4025, 4050, 4075, 4100, 4125, 4150, 4175, 4200, 4225, 4250, 4275, 4300, 4325, 4350, 4375, 4400, 4425, 4450, 4475, 4500, 4525, 4550, 4575, 4600, 4625, 4650, 4675, 4700, 4725, 4750, 4775, 4800, 4825, 4850, 4875, 4900, 4925, 4950, 4975, 5000 percent or more in a Dirofilaria exhalant signature that indicates infection with one or more stages of Dirofilaria, such as the adult stage. In some embodiments, one or more VOCs present in a Dirofilaria exhalant signature in an exhalant from an infected subject is not present or is present at below detectable limits in the exhalant of a non-Dirofilaria infected subject, such that those VOC(s) can be said to be increased in a Dirofilaria exhalant signature of an infected individual.

In some embodiments, the amount (whether a relative amount or an absolute amount) of one or more of the VOCs in the Dirofilaria exhalant signature in the sample is decreased, as compared to a suitable control, threshold value, standard, or a combination thereof, in a Dirofilaria exhalant signature that indicates the subject from which the sample was obtained is infected with one or more stages of Dirofilaria, such as the adult stage. In some embodiments, the amount of one or more of the VOCs in the Dirofilaria exhalant signature in the sample is decreased 1-100 percent (i.e., is absent or is not detectable) in a Dirofilaria exhalant signature that indicates the subject from which the sample was obtained is infected with one or more stages of Dirofilaria, such as the adult stage. In some embodiments, the amount of one or more of the VOCs in the Dirofilaria exhalant signature is decreased 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent, in a Dirofilaria exhalant signature that indicates that the sample was obtained one from a subject infected with one or more stages of Dirofilaria, such as the adult stage. In some embodiments, one or more VOCs that is/are present in a signature that is indicative of a non-infected subject is/are not present or is undetectable in a signature that is indicative of an infected subject.

Also described herein are methods of treating and/or preventing Dirofilaria infection in a subject that includes non-invasively diagnosing, prognosing and/or staging Dirofilaria infection in the subject by a method previously described herein and administering to the subject an anthelmintic effective to prevent at least the adult stage of Dirofilaria in the subject one or more times, administering to the subject a treatment effective to kill the adult stage of Dirofilaria in the subject one or more times, or both. Subjects that are determined to not be infected with an adult stage of Dirofilaria are not necessarily treated with a treatment effective to kill the adult stage of Dirofilaria. It will be appreciated that some preventives can also be effective to kill the adult Dirofilaria. For example, moxidectin and ivermectin, have been observed to not only prevent the development of adult *D. immitis* in a host, such as a canine, but also kill adult *D. immitis* with continued exposure for at least 5-12 or more months.

In some embodiments, the anthelmintic effective to prevent at least the adult stage of Dirofilaria comprises: ivermectin, moxidectin, milbemycin oxime, selamectin, eprinomectin, or a combination thereof. The prevention can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366 or more times per year.

In some embodiments, the method further includes co-administering a composition effective to prevent, treat, or both an intestinal or other internal parasite, fleas, ticks, and other external parasite, or any combination thereof. External parasites include, but are not limited to, fleas, ticks, mites and worms (e.g., roundworm larvae). In some embodiments, the composition effective to prevent, treat, or both an intestinal or other interrnal parasite, fleas, ticks, or other external parasite, or any combination thereof is one or more compounds of one or more of the following classes: benzimidazole, depolarizing tetrahydropyrimidines, a macrocyclic lactone, neonicotinoid, phenylpyrazole, piperazine, oxadiazine, pyrethrin, pyrethroid, isoxazoline, and an insect growth regulator. In some embodiments, the composition effective to prevent, treat, or both an intestinal parasite, fleas, ticks, or other external parasite, or any combination thereof is selected from pyrantel, pyrantel pamoate, febantel, praziquantel, oxibendazole, piperazine, spinosad, fluralaner, afoxolaner, fipronil, sarolaner, lotilaner, lufenuron, imidacloprid, Methoprene, S-methoprene, pyriproxyfen, fenbendazole, flumethrin, selamectin, eprinomectin, indoxacarb, permethrin, nitenpyram, and combinations thereof. The term "co-administration", as used herein, refers to the administration of two or more active ingredients that can be delivered together or apart (e.g. spatially, temporally, or both). Co-administration includes administration of two or more different active ingredients within the same composition, simultaneous administration of two or more different compositions and/or active ingredients, at the same time but not within the same formulation or composition. Co-administration includes administration where one composition is an extended release formulation and one is not. Co-administration includes administration at different times but such that the effect of the active ingredient(s) overlap in time. For example, a monthly heartworm prevention formulation can be administered monthly on top of a flea prevention that is effective for 3 months (e.g., administration of a monthly ivermectin heartworm prevention (e.g., Heartgard prevention) and three-month Bravecto flea prevention). The prevention can be administered 1, 2, 3, 4, 5, 6, 7, 8, 9, 10, 11, 12, 13, 14, 15, 16, 17, 18, 19, 20, 21, 22, 23, 24 or more times per year.

In some embodiments, the treatment effective to kill the adult stage of Dirofilaria in the subject one or more times, or both is a treatment effective to kill adult *D. immitis* in canines. The treatment effective to kill adult *D. immitis* in canines can be melarsomine, which can be delivered in a series of injections. Treatment can also include one or more courses of doxycycline at suitable amounts (see e.g., Carreton et al. 2020. Vet Parasitol. 283:109141). Doxycycline is used to kill *Wolbachia* bacteria that inhabit the adult and other stages of *D. immitis*. By killing the *Wolbachia* bacteria, the adult worms are more susceptible to treatment with melarsomine. In some embodiments, *D. immitis* treatment in dogs includes a 14-30 day course of doxycycline followed by a single injection of melarsomine or two injections of melarsomine given 24 hours apart. In treatments where only a single injection of melarsomine is administered after completion of a course of doxycycline, two injections of melarsomine given 24 hours apart are given about 30 days after the first single melarsomine injection. This is what is referred to in the art the AHS approved method of treating adult *D. immitis* infection in dogs.

It will be appreciated that in some cases, the dogs are too ill or it is otherwise impractical to complete the AHS approved method of treating adult *D. immitis* infection in dogs. Other approaches based on long term and/or more frequent use of macrocyclic lactones (more frequent than on-label use for heartworm prevention) have been used to more slowly kill the heartworms (see e.g., Venco et al., 2004. Vet Parasitol. 124:259-268; Kramer et al., 2018. Vet Parasitol. 30:254:95-97; Genchi et al., 2019. Vet Parasitol. 273: 11-16; Bendas et al., 2017. Parasit Vectors. 10(1):246; Ames et al. 2020. Vet Parasitol: 282:109099; Alberigi et al., 2020. Front Vet Sci. 6:440; Savadelis et al., 2020. J Vet Intern Med. 34(5):1734-1745; Paterson et al. 2020. Vet Parasitol. 284: 109194; Savadelis et al. 2018; Parasit Vectors. 11(1):98). Because the adult *D. immitis* are killed off at a slower rate, this method can be better tolerated in certain patient populations (e.g., those with co-morbidities) than the melarsomine treatment protocol which results in rapid die off of adult worms. This method is also less expensive than treatment with melarsomine, which can make treatment more widely available and more practical for shelters and rescue organizations. Such approaches are generally referred to as the "slow-kill" treatment for heartworm disease in dogs. It has been demonstrated that some macrocyclic lactones such as ivermectin or moxidectin when administered at levels used to prevent adult stage *D. immitis* concurrently for at least 5-12 months or more along with one or more 30 day courses of doxycycline during macrocyclic lactone (e.g., ivermectin or moxidectin) administration can be effective to kill adult *D. immitis* in dogs (see e.g., Venco et al., 2004. Vet Parasitol. 124:259-268; Kramer et al., 2018. Vet Parasitol. 30:254:95-97; Genchi et al., 2019. Vet Parasitol. 273:11-16; Bendas et al., 2017. Parasit Vectors. 10(1):246; Ames et al. 2020. Vet Parasitol: 282:109099; Alberigi et al., 2020. Front Vet Sci. 6:440; Savadelis et al., 2020. J Vet Intern Med. 34(5):1734-1745; Paterson et al. 2020. Vet Parasitol. 284:109194; Savadelis et al. 2018; Parasit Vectors. 11(1):98). When moxidectin is used the slow-kill method is also referred to in the art as the "moxy-doxy" treatment. In some embodiments, the treatment effective to kill adult Dirofilaria can include a slow-kill method that can include administration of a macrocyclic lactone (such as ivermectin or moxidectin) and one or more 10, 14, or 30 day course of doxycycline during the time the macrocyclic lactone is being administered. In some embodiments, the marcocyclic lactone is administered for a period of 5, 6, 7, 8, 9, 10, 11, 12, 13, 14, 15, 16, 17, 18, 19, 20, 21, 22, 23, 24, or more consecutive months or more. In some embodiments, the macrocyclic lactone is delivered as a bolus dose weekly, bi-weekly, monthly, bi-yearly, or yearly. The macrocyclic lactone can be co-administered with one or more other compositions, such as those effective to treat or prevent fleas, ticks, and/or other parasites, such as intestinal parasites.

In some embodiments, the methods of diagnosing, prognosing, staging, treating and/or preventing Dirofilaria infection in a subject can include non-invasively and actively collecting an exhalant sample from the subject. In other words, the method can include exhalant sampling. As described in greater detail elsewhere herein, exhalant sampling can be performed using a device described herein.

In some embodiments, after exhalant collection VOCs present in the exhalant can be concentrated and/or enriched. VOC concentrated and/or enriched can occur within the collection device or outside of the device, but prior to VOC analysis. For example, in some embodiments, VOCs can be concentrated and/or enriched on a sorbent material prior to analysis. As is described in greater detail elsewhere herein, the sorbent material can be contained in the collection device (e.g., in the one or more removable collection chamber). In other embodiments, the sorbent material is not contained within the device, but the collected exhalant in the collection device or component thereof is passed through a sorbent material outside of the device prior to VOC analysis.

VOCs can be extracted from a collected sample and/or sorbent or other exhalant collection and/or VOC concentration material for analysis by a suitable extraction method or technique. Such techniques are generally known in the art and include desorption techniques (e.g., thermal desorption and chemical desorption) and extraction techniques (e.g., solvent extraction, solid-phase micro-extraction, and membrane extraction).

The VOCs present in the sample can be analyzed using any suitable analytic technique. In some embodiments, the VOCs are analyzed using a gas chromatography (GC) based technique. The GC can include various detectors for analysis including flame ionization, thermal conductivity, electron capture, nitrogen phosphorous, flame photometric, photo-ionization, Hall electrolyte conductivity, and mass detectors (such as mass spectrometers). In some embodiments, the VOCs present in the exhalant sample are analyzed using GC-MS (gas chromatography-mass spectrometry). In some embodiments, the VOCs present in the exhalant sample are analyzed using GC-TOF-MS (GC-time of flight-MS).

Other suitable methods for detection of VOCs in a sample are described elsewhere herein and are known in the art. For example, VOCs can be detected and analyzed using various separation techniques, spectroscopy techniques, various sensors and sensor arrays, and combinations thereof (see e.g., Hashoul and Haick. 2019. Eur Respir Rev. 28:190011; Paredi et al. 2000. Am J Respir Crit Care Med. 162:1450-1454; Kischkel et al. 2010. Clin. Chim. Acta. 411:1637-1644; de Gennaro et al. 2010. Anal Bioanal Chem. 398: 3043-3050; Baker et al. 2006. Eur Respir J. 27: 929-936; Alkhouri et al. 2014. Eur. J Gastroenterol Hepatol. 26:82-87; Broza and Haick. 2013 Nanomedicien. 8:785-806; Rock et al. 2008. Chem Rev. 108:705-725; van de Kant et al. 2012. Respir Res 13: 117; Vishinkin and Haick. 2015. Small 11:6142-6164; Montuschi et al. 2013. Respiration. 85:72-84; Tang et al. 2010. Sensors. 10: 6463-6476; and Bikov et al. 2015. J Breath Res. 9: 34001). Such methods can be used to detect one or more of the VOCs in a Dirofilaria exhalant signature described in greater detail elsewhere herein.

DEVICES

Also described herein are devices that are capable of non-invasively collecting an exhalant sample from a subject, such as a human or non-human animal subject, for VOC analysis. Thus, the devices described herein are generally suitable for collecting and containing VOCs present in the sample exhalant collected by the device. Generally, the devices are capable of collecting (such as via grabbing or actively collecting) exhalant from an individual human or non-human animal. "Non-invasive" as used in this context herein refers to collecting exhalant from a human or non-human animal without any part of the device being placed within the body of the subject, including within the mouth or nose of the subject. The device can be capable of sampling exhalant at the single, individual subject level as opposed to sampling general air within an environment (such as a room, holding area, or cage) that the subject is in. The device can be configured to allow for point of use analysis or allow for easy removal of the collected sample from the device to be sent for processing and/or analysis at an off-site facility (such as an off-site testing laboratory).

In some embodiments, a device configured to collect an exhalant for analysis of volatile organic compounds (VOCs) present in the exhalant of a single non-human animal subject include an exhalant collector configured to actively and non-invasively collect exhalant expelled from the non-human animal subject without being placed in an orifice of the subject; and one or more removable collection chambers, each removable collection chamber configured to hold an amount of exhalant collected and are suitable for containment of VOCs, where the one or more removable collection chambers are operatively coupled to the exhalant collector. In some embodiments, the number of collection chambers is 1, 2, 3, 4, 5, 6, 7, 8, 9, 10. The one or more collection chambers can be removed so as to be replaced after use (in the case of chambers that cannot be regenerated or are otherwise single-use). The one or more removable collection chambers can be configured such that after sample collection they can be removed and be sent off to an off-site lab for VOC analysis or be analyzed in-house (or at the point of collection).

In some embodiments, the exhalant collector includes or is coupled to one or more low pressure air pumps capable of moving exhalant expelled from the subject and external to the device into the exhalant collector and into the one or more removable collection chambers. The pump(s) can also be used to move air through any conduits coupling the exhalant collector and one or more removable collection chambers (such as tubes, chambers, reservoirs, filters, etc.). The device can also include one or more additional pumps coupled to one or more other parts of the device to assist with air flow throughout the device.

In some embodiments, the device can include one or more one-way air valves configured to control the flow of exhalant in one direction through the device from the external environment through the exhalant collector and into and optionally through the one or more removable collection chambers. In some embodiments, the device includes 1, 2, 3, 4, 5, 6, 7, 8, 9, 10 or more one-way valves. In some embodiments, two or more of the one-way valves can be placed in series with each other. In some embodiments, the exhalant collector can include one or more of the one or more one-way valves. In some embodiments, one or more of the one or more removable collection chambers includes one or more of the one or more one-way valves. In some embodiments, one or more of the one-way valves can be placed with in conduits that can be included in the device and connect one or more of the one or more removable collection chambers. In some embodiments, one or more of the one-way valves can be placed with in conduits that can be included in the device and that connect the exhalant collector to one or more of the one or more removable collection chambers.

In some embodiments, the exhalant collector is a tube that is configured to be placed in effective proximity to a mouth, nose, nostrils, or a combination thereof of the subject during collection and draw exhalant into the exhalant collector. In use, an operator can hold or otherwise place the intake end of the tube (i.e., the end not operatively connected to the one or more removable collection chambers and/or other portion of the exhalant collector) in effective proximity to a nose and/or mouth of the subject. Effective proximity as used in this context herein is the distance and location in space where the end of the exhalant collector can be placed such that a sample of exhalant is collected into the device. In some embodiments, the distance is 1, 2, 3, 4, 5, 6, 7, 8, 9, 10, 11, 12, 13, 14, 15, 16, 17, 18, 19, 20 or more cm from the mouth and/or nose of the subject. During use the exhalant collector can be placed in effective proximity of a mouth and/or nose of a subject to collect exhalant for a period of time. In some embodiments, the period of collection time is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds. In some embodiments, the period of collection time is 1, 2, 3, 4, or 5 minutes. The tube can be configured to be cleaned and/or sanitized between uses. In some embodiments, the tube can be removable. In some embodiments, tube is disposable and configured for single use.

In some embodiments, the exhalant collector is configured as a mask that is configured to cover the mouth and nose of the subject. In some embodiments, the mask can include one or more fastening members that can secure the mask over the mouth and/or nose of the subject during collection. In some embodiments, the mask is shaped to match the anatomical features of the mouth and/or nose region of the subject so as to minimize the amount of environmental air that is sampled. In, some embodiments, the mask includes a gasket so as to form a seal between the mask and the subject to minimize the environmental air that is collected. The mask can be configured such that it can be cleaned and/or sanitized between uses. In some embodiments, the mask can be configured as a single-use disposable mask.

In some embodiments, the one or more of the component of the device is made of one or more materials configured to preserve VOCs for analysis. In some embodiments, such materials can be capable of capturing, retaining, and/or otherwise holding VOCs from collected exhalant. In some embodiments, such a material is inert to VOCs (in other words does not react with the VOCs) or is resistant to reacting with VOCs. In some embodiments, the material is a sorbent material capable of adsorbing one or more VOCs from the collected exhalant. Suitable materials include, Nalophan, Tedlar, inertised aluminium, Teflon, or combinations thereof.

In some embodiments, the device includes one or more filters. In some embodiments, the exhalant collector, the one or more removable collection chambers, or both comprise one or more filters. In some embodiments, at least one of the one or more filters is effective to remove environmental VOCs from exhalant collected. In some embodiments, one or more of the one or more filters can filter non-VOC components of the exhalant, such as carbon dioxide or other gasses, particulates, microbes or viruses, and other compounds that can interfere with VOC collection, processing, and/or downstream analysis.

In some embodiments, the exhalant collector is operatively coupled to the one or more removable collection chambers via one or more conduits. In some embodiments, the conduits are tubing (flexible or inflexible), other chambers, reservoirs, vessels, bladders, and the like. In some embodiments, the exhalant collector is directly coupled to at least one of the one or more removable collection chambers with no conduits in between. Conduits can also be between two collection chambers. Any of the conduits included in the device can include one or more filters and/or one or more one-way valves.

The one or more removable collection chambers can be configured such that they can contain VOCs. In some embodiments, the one or more removable collection chambers is configured to preserve VOCs for analysis. In some embodiments, the one or more removable collection chambers includes one or more materials capable of capturing, retaining, and/or otherwise holding VOCs from collected exhalant. In some embodiments, such a material is inert to VOCs (in other words does not react with the VOCs) or is resistant to reacting with VOCs. In some embodiments, the material is a sorbent material capable of adsorbing one or more VOCs from the collected exhalant. Suitable materials include, Nalophan, Tedlar, inertised aluminium, Teflon, or combinations thereof. In some embodiments, the removable collection chamber(s) include solid phase microextraction fiber. In some embodiments the solid phase microextraction fiber is composed of carboxen and polydimethylsiloxane.

In some embodiments, the one or more removable collection chambers is capable of capturing VOCs is capable of releasably capturing VOCs from a collected exhalant. In some embodiments, capture VOC release is via desorption. In some embodiments, the one or more removable collection chambers is configured for single-use. In some embodiments, the one or more removable collection chambers can be regenerated and reused for subsequent collections. In some embodiments, the one or more removable collection chambers is capable of concentrating and/or enriching VOCs collected from exhalant. The one or more removable collection chamber can be any suitable shape or size. In some embodiments, the one or more removable collection chambers are tubes, bags, reservoirs, cartridges, traps, chips, or a combination thereof.

As previously described, in use exhalant from a can be actively and non-invasively collected via the exhalant collector from the mouth and/or nose of the subject. In some embodiments one or more low-pressure air pumps move the exhalant into the device, through the exhalant collector, through optional conduit, and into the one or more collection chambers. In some embodiments, VOCs are collected in one or more collection chambers (such as on one or more materials in the one or more collection chambers). VOCs can then be removed from the collection chamber(s), optionally processed (such as enriched, concentrated), and analyzed by a suitable analytical technique (such as a GC or other chromatography or compound analysis method).

In some embodiments, the device includes one or more sensors and/or sensor arrays capable of detecting one or more VOCs, such as any of the VOCs of a Dirofilaria exhalant signature described in greater detail elsewhere herein. The one or more sensors and/or sensor arrays can be any suitable sensor including, but not limited to, those described in e.g., Hashoul and Haick. 2019. Eur Respir Rev. 28:190011; Spinelle et al. 2017. Sensors. 17 (7) 1520; Wang et al., 2020. Front. Chem. doi.org/10.3389/fchem.2020.00339; and Li et al. 2020. Front. Chem. doi.org/10.3389/fchem.2020.00321. In some embodiments, the one or more sensor(s) and/or sensor array(s) are nanomaterial based. In some embodiments, the one or more sensor(s) and/or sensor array(s) are or include one or more chemoresistors (e.g., a chemoresistor based on monolayer-capped nanoparticles, single-wall carbon nanotubes, conducting polymers, metal oxide films, quartz microbalance with a selective coating), colometric sensor, surface acoustic wave sensor, and any combination thereof. In some embodiments, the one or more sensors and/or sensor arrays capable of detecting one or more VOCs is/are coupled to or are otherwise incorporated into the one or more removable collection chambers, exhalant collector, or both.

Kits

Also described herein are kits that can contain a device described herein and/or one or more components thereof, and/or one or more replacement parts. In some embodiments the kit contains, an exhalant collectors or components thereof, one or more removable collection chambers, VOC analysis reagents, VOC preservative reagents, VOC processing reagents, cleaning reagents, component regeneration agents, filters, replacement one-way valves, or any combination thereof. In some embodiments, the kit only includes reagents and/or replacement components such as filters, valves, exhalant collector or components thereof, removable sample collection chambers, or combinations thereof. In some embodiments, the kit includes a complete device, and optionally additional replacement components and/or reagents.

In some embodiments, the kit can include one or more removable collection chambers configured for use in an exhalant collection device described elsewhere herein and instructions fixed in a tangible medium of expression wherein the instructions provide directions, safety information, and/or other product information for using device, the one or more removable collection chambers, and/or other component included in the kit to collect volatile organic compounds from an exhalant of a subject and detecting a Dirofilaria exhalant signature to diagnose, prognose, and/or stage a Dirofilaria infection in the subject.

In some embodiments, the one or more removable collection chambers is configured to preserve VOCs for analysis. In some embodiments, the one or more removable collection chambers wherein the one or more removable collection chambers is capable of concentrating and/or enriching VOCs from collected exhalant. In some embodiments, the one or more removable collection chambers comprises a material capable of releasing VOCs that are captured by a material in the one or more removable collection chambers.

Further embodiments are illustrated in the following Examples which are given for illustrative purposes only and are not intended to limit the scope of the invention.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1—Canine Exhalant Sampling

This Example can at least demonstrate unique volatile organic compounds (VOCs) in exhalant from dogs infected with *D. immitis*. Exhalant was collected from twenty-four laboratory beagles (n=12 antigen positive for *D. immitis*, n=12 no antigen detected (NAD)). Exhalant was directly sampled from individual dogs and VOCs in the exhalant was analyzed using gas chromatography. Exhalant collection was performed using a very low pressure (about 1 L per minute) air pump coupled to a Teflon material coated collection bag that had about a 1 L capacity via Teflon material coated tubing that was unique to each individual dog (see e.g., FIG. 1) During sampling, the air pump was held up near the dog's nares to specifically sample the exhalant. Exhalant was sampled over a 1-3 minute period or until the collection bag was about seventy five percent full. A negative control sample was obtained as well using the same apparatus set up but obtaining a sample from the ambient environment (also referred to as "room air" herein). A positive control compound (siloxane rich deodorant) was captured in each bag to allow for confirmation that a known compound can be extracted via the downstream analytics. This methodology has advantages that it is simple and does not require extensive restraint beyond making sure it does not move from the collection area (e.g., an examination table, area, or lap it is present on/in).

Sample analysis was completed using gas chromatography-time of flight (GC-TOF). Following collection, within one week, the sample was extracted from the bag using a solid phase microextraction (SPME) fiber made of caboxen polydimethylsiloxane (CAR/PDMS) immersed in the bag septum for 15 minutes which adsorbs VOCs. The collected VOCs are then run the GC/MS.

The netCDF files were imported into MZmine software (T. Pluskal, et al. BMC Bioinformatics 11:395 (2010)) and processed with the ADAP-GC software tool using the unit mass resolution parameters suggested (A. Smirnov, et al. J. Proteome Res.171:470-478 (2018)). The resulting aligned peak list was exported in the metaboanalyst format and subsequently imported into metaboanalyst (Chong, J., et al. Nucl. Acids Res. 46, W486-494 (2018)) for statistical tests and graph generation. Compounds were identified with AMDIS and NIST 2.0. In order to extract volatiles from the Teflon material coated bags, a SPME CAR/PDMS fiber is inserted into the septum of the bag and held in place for about 60 minutes to allow VOCs to adsorb to the fibers. The SPME is then retracted and inserted into a GC-TOF, with the following settings for thermal desorption: Start at 35 degrees Celsius, hold for about 1 minute, ramp 10 degrees Celsius per minute to 50 degrees Celsius, then ramp 30 degrees Celsius per minute to 250 degrees Celsius and hold for about 2 minutes. The output chromatograph files were processed manually and then through AMDIS software to compare manual and automated mass spec methods.

Results

In dogs infected with heartworm and negative control dogs without heartworm, 1 L of breath was sampled from each dog using the method above (without direct physical contact between the dogs and collectors) over a 1-3 minute period.

Figure 2:
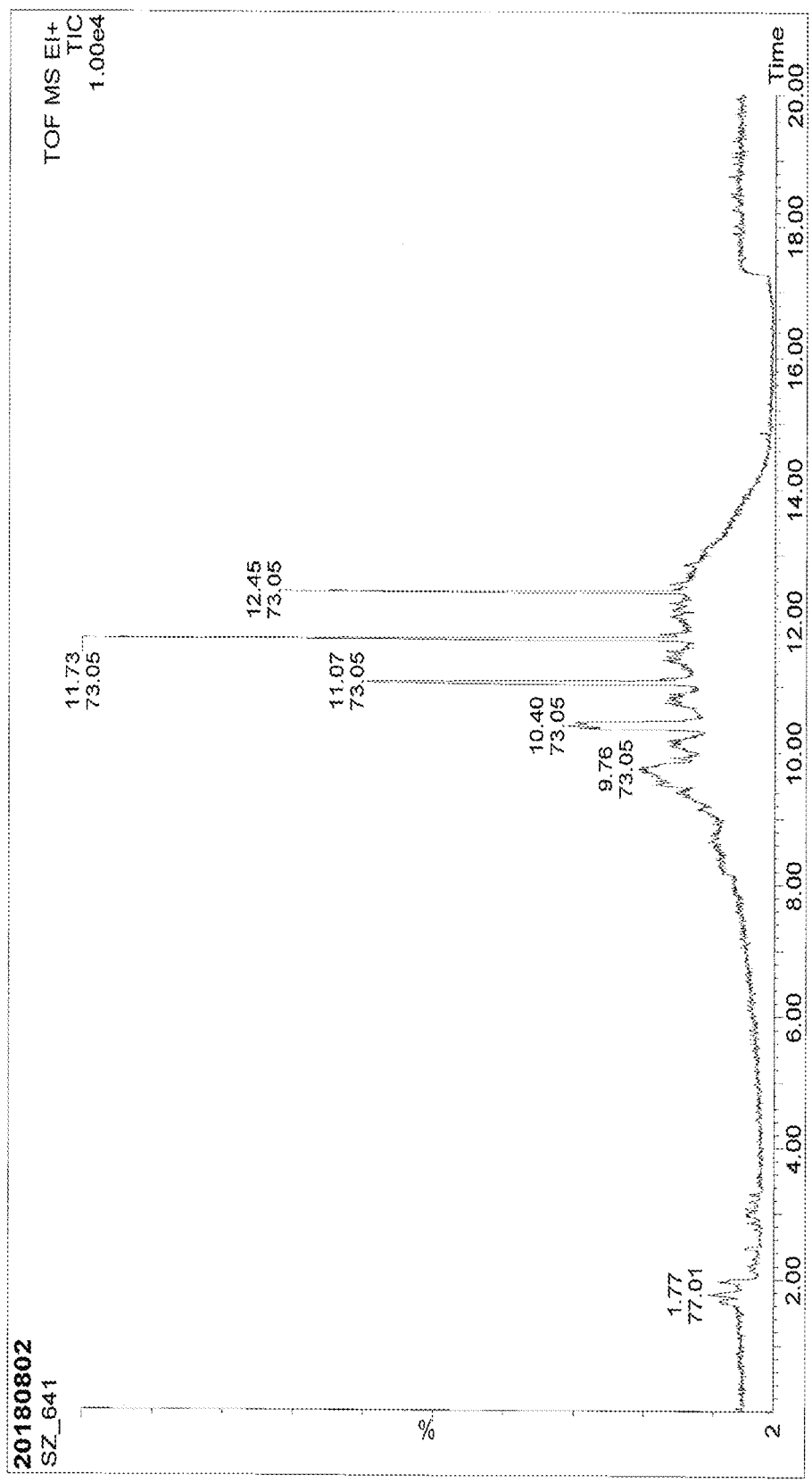
FIG. 2 shows an exemplary chromatogram resulting from SPME adsorbed fibers immersed in a 1 L breath capture bag and shows detected compounds from a canine breath sample.

Dog breath samples were collected and analyzed using a GC-TOF and SPME fibers to adsorb and then thermally desorb VOC compounds into the GC. Resultant chromatographs were saved and analyzed using AMDIS library software that uses an algorithm to determine which compounds are present in the chromatograph (FIG. 2 and Table 1). Individual compounds were also pulled manually and the library of compounds from samples using the automated and manual processes was compared.

TABLE 1

| Sample of detected VOCs |
|---|
| Eicosane, 3-methyl |
| Octane, 2,3,6,7-tetramethyl |
| Quinoxaline, 2,3-diphenyl |
| Acetamide, 2-fluoro |
| Asparagine |
| Methanamine, N,N-dimethyl, N-oxide |

TABLE 1-continued

Sample of detected VOCs

1-Triethylsilyloxyheptadecane
1-Propanamine, N-nitro

Example 2—Compounds in Exhalant Separate *D. immitis* Infected Dogs from Non-Infected Dogs Dogs known to be infected with canine heartworm (Dirofilaria *immitis*) and individuals who are confirmed negative were surveyed to detect VOC signatures. Exhalant sampling was performed as described in Example 1. Out of 40 sampled dogs, and negative control room air samples, a total of 411 unique VOC compounds were identified. VOCs extracted from samples were then classified into chemical class and subclass. For example, if 1,1-Difluoro-trans-2,3-dimethyl-cyclopropane was extracted from them sample, it was grouped into the class-alkenes and subclass-cyclic alkene. Once classified, heat maps were generated from the subclass to identify broad trends.

Results

Figure 3:
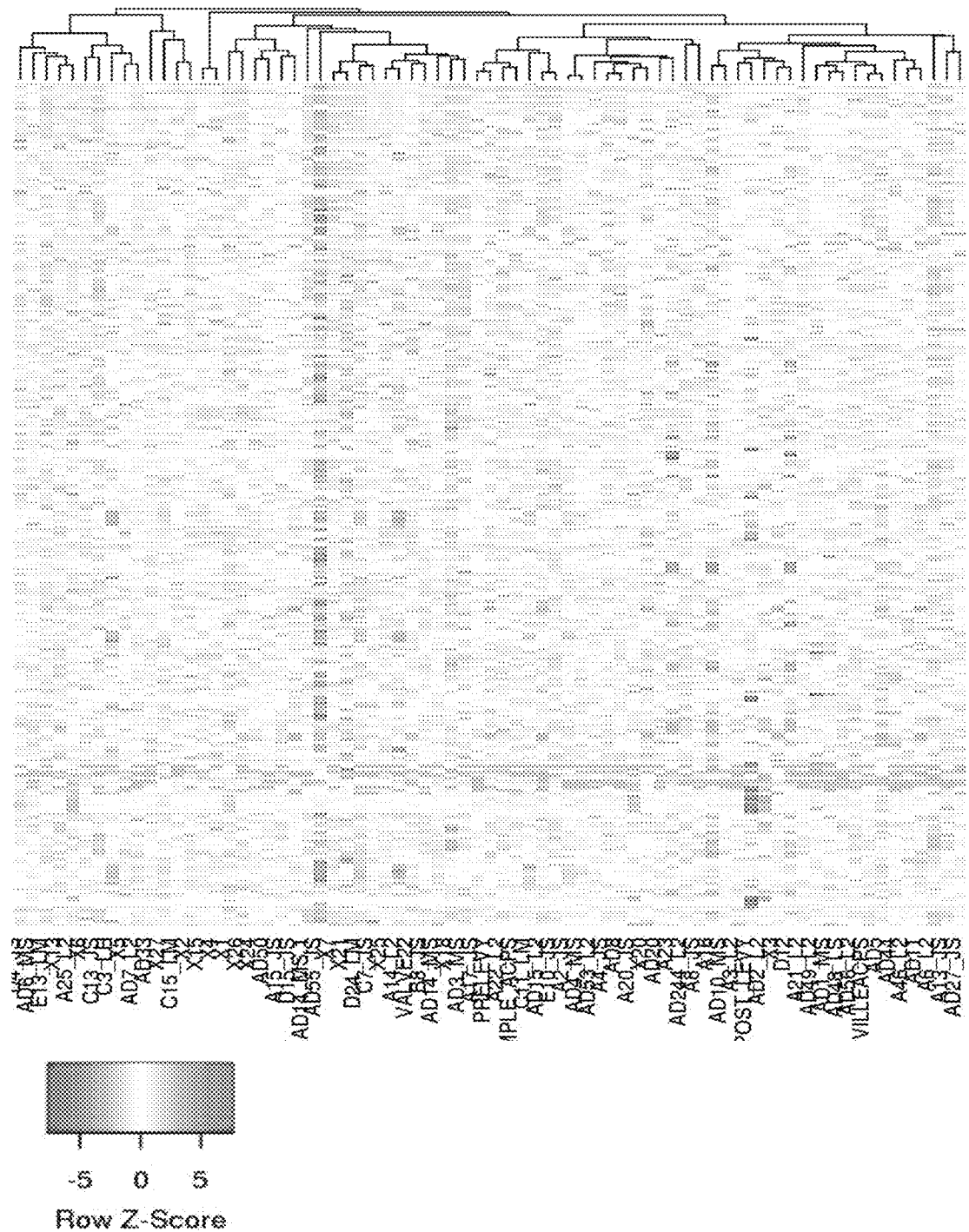
FIG. 3 shows a gas chromatography array heat map of a Dirofilaria immitis (D. immitis) naturally infected population. Each row represents a different individual canine.

FIG. 3 shows a gas chromatography array heat map of *D. immitis* naturally infected population. Each row represents a different individual canine.

Figure 4A:
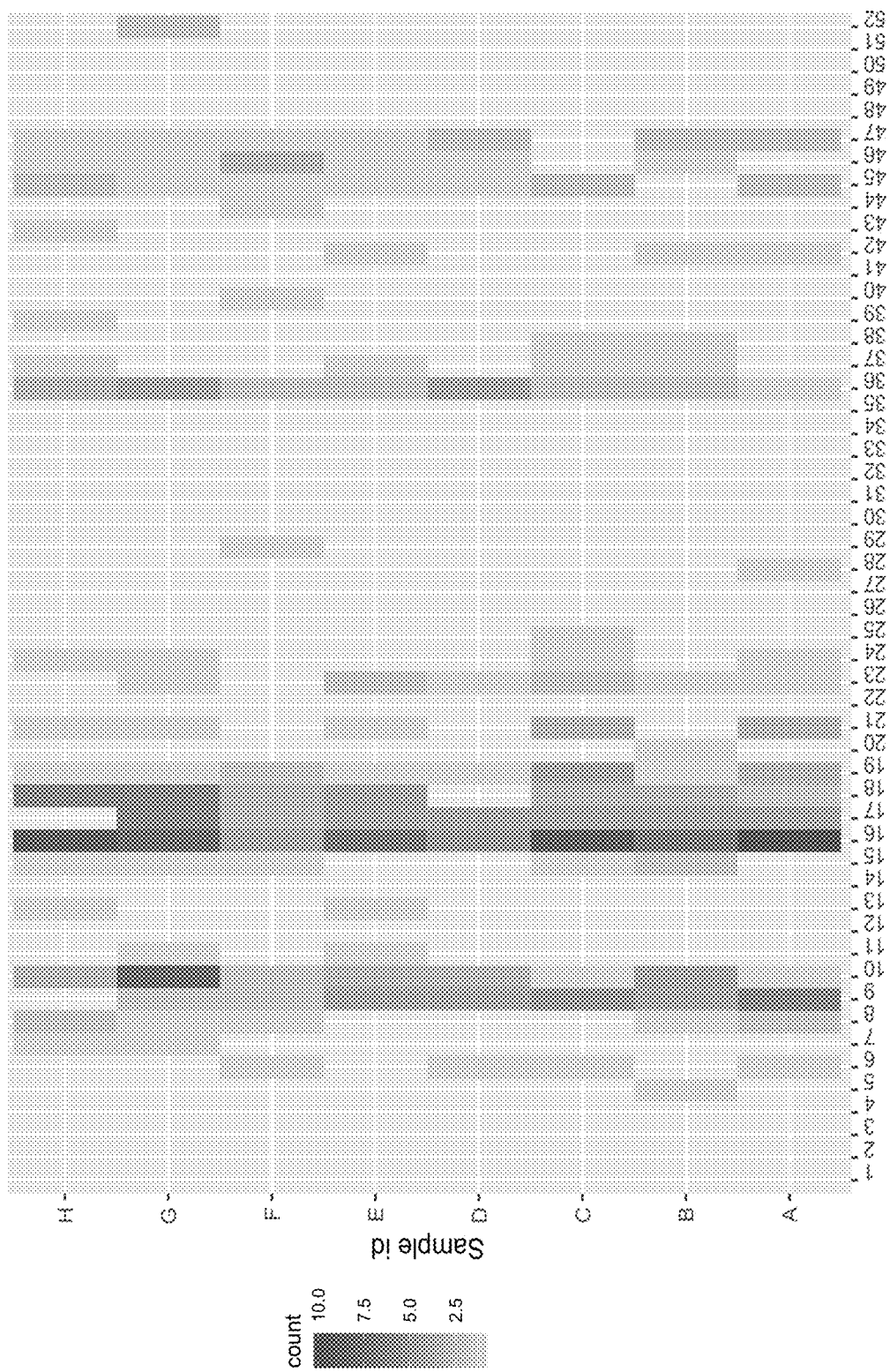
FIGS. 4A-4B show gas chromatography arrays that can demonstrate that there are significantly more VOCs in canines infected with D. immitis (FIG. 4A) as compared to non-infected canines (FIG. 4B) (395 v. 277 P<0.01).
Figure 4B:
Figure 5A:
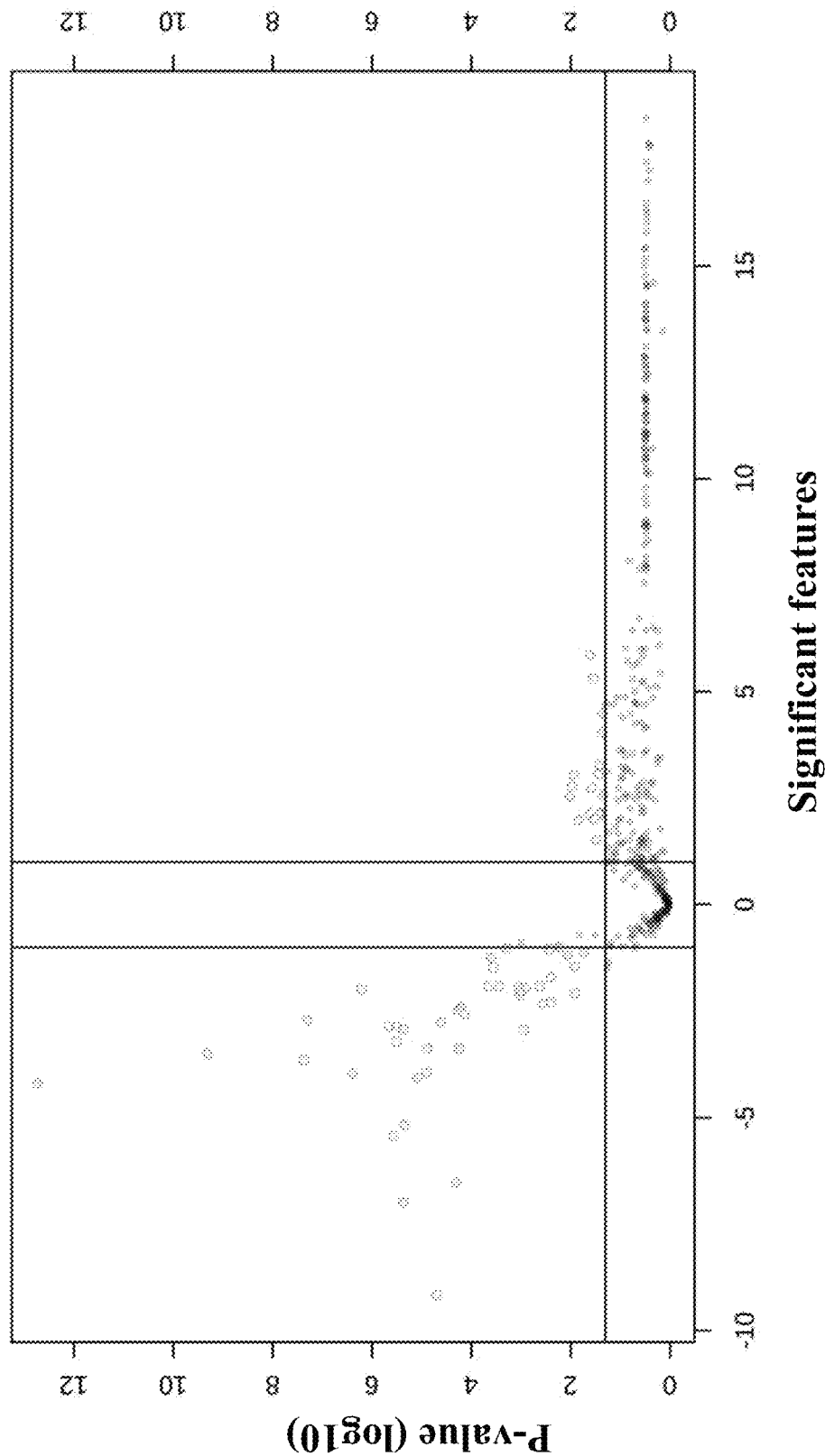
FIGS. 5A-5B show plots demonstrating volatile organic compounds (VOCs) detected in canine exhalant. 502 total unique compounds were detected. Results demonstrate that breath capture can allow for detection of distinct compounds in canine exhalant when comparing pre- and post-room sampling.
Figure 5B:
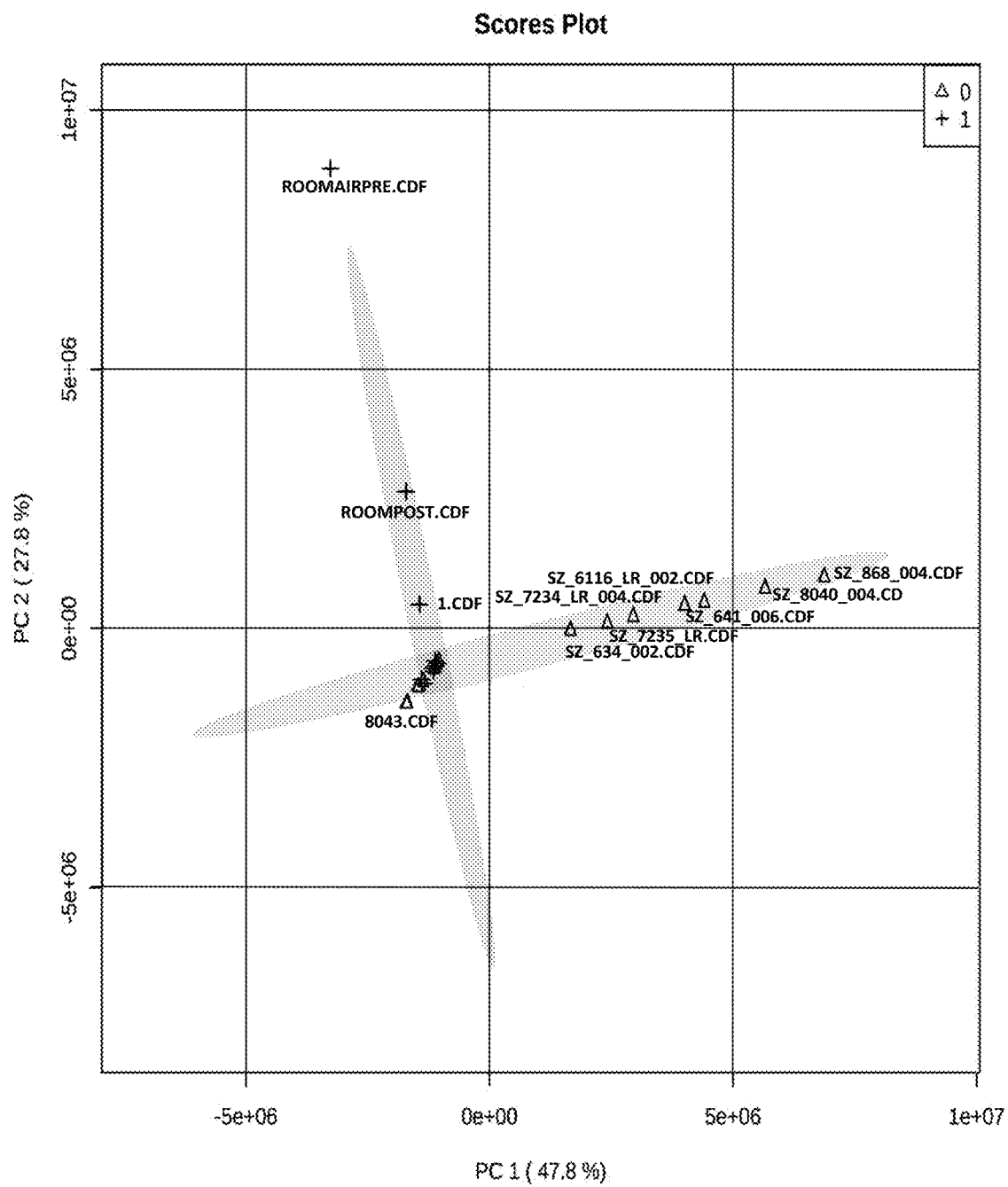

FIGS. 4A-4B show gas chromatography arrays that can demonstrate that there are significantly more VOCs in canines infected with *D. immitis* (FIG. 4A) as compared to non-infected canines (FIG. 4B) (395 v. 277 P<0.01). The heat map subclass of VOCs found in the exhalant of sampled dogs in FIGS. 4A-4B show that *D. immitis* infected canines have a broader diversity of subclass VOCs in their exhalant that non-infected (or NAD) canines. FIGS. 5A-5B show plots demonstrating volatile organic compounds (VOCs) detected in canine exhalant. 502 total compounds were detected. Results can demonstrate that breath capture can allow for detection of distinct compounds in canine exhalant when comparing pre- and post-room sampling. FIGS. 5A-5B can demonstrate that VOCs captured from dog exhalant were significantly different than those in room air and validate the sample collection and analysis method.

Figure 6A:
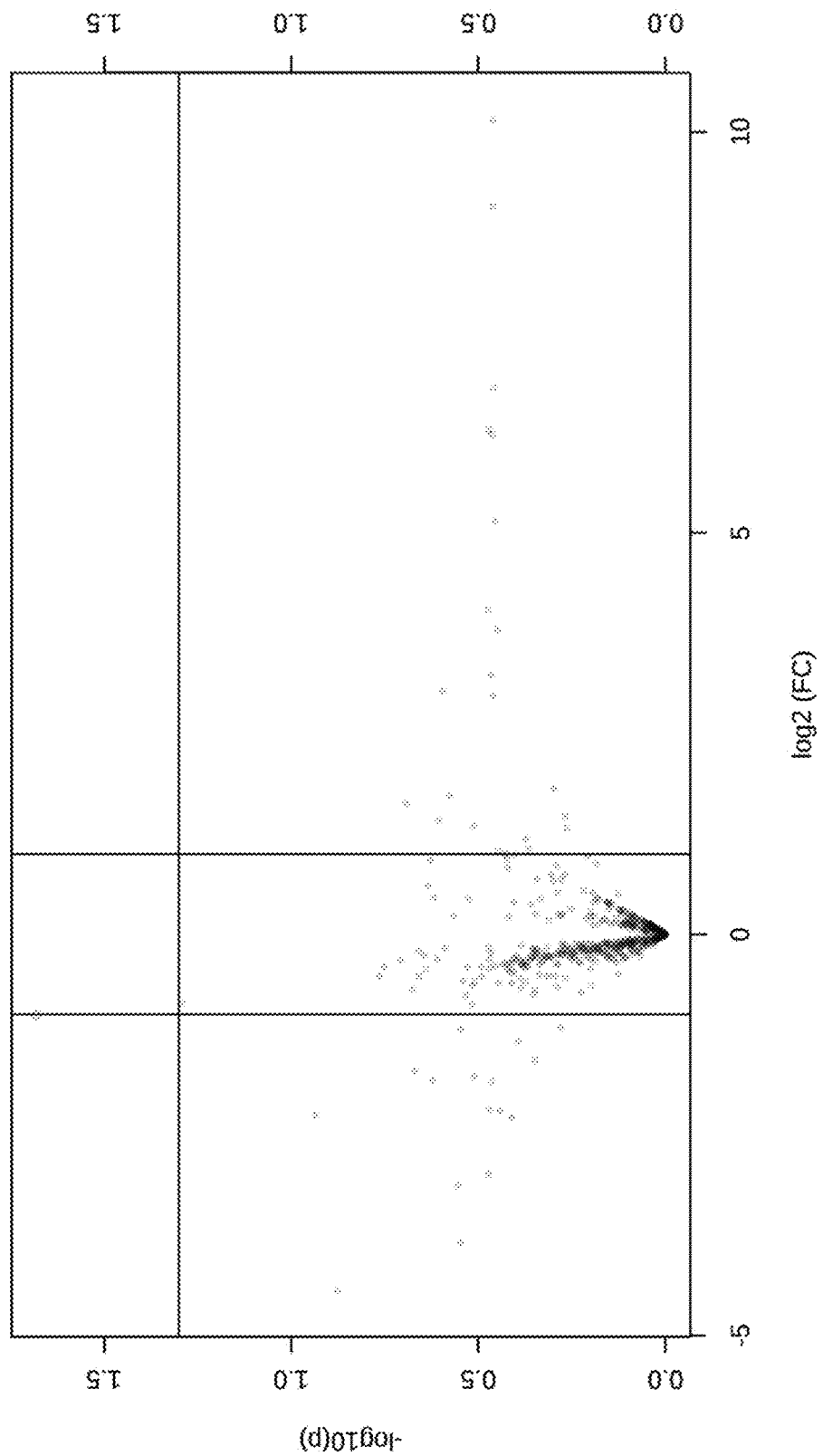
FIGS. 6A-6B show plots that can demonstrate no significant differences in VOCs were attributable to sex differences.
Figure 6B:
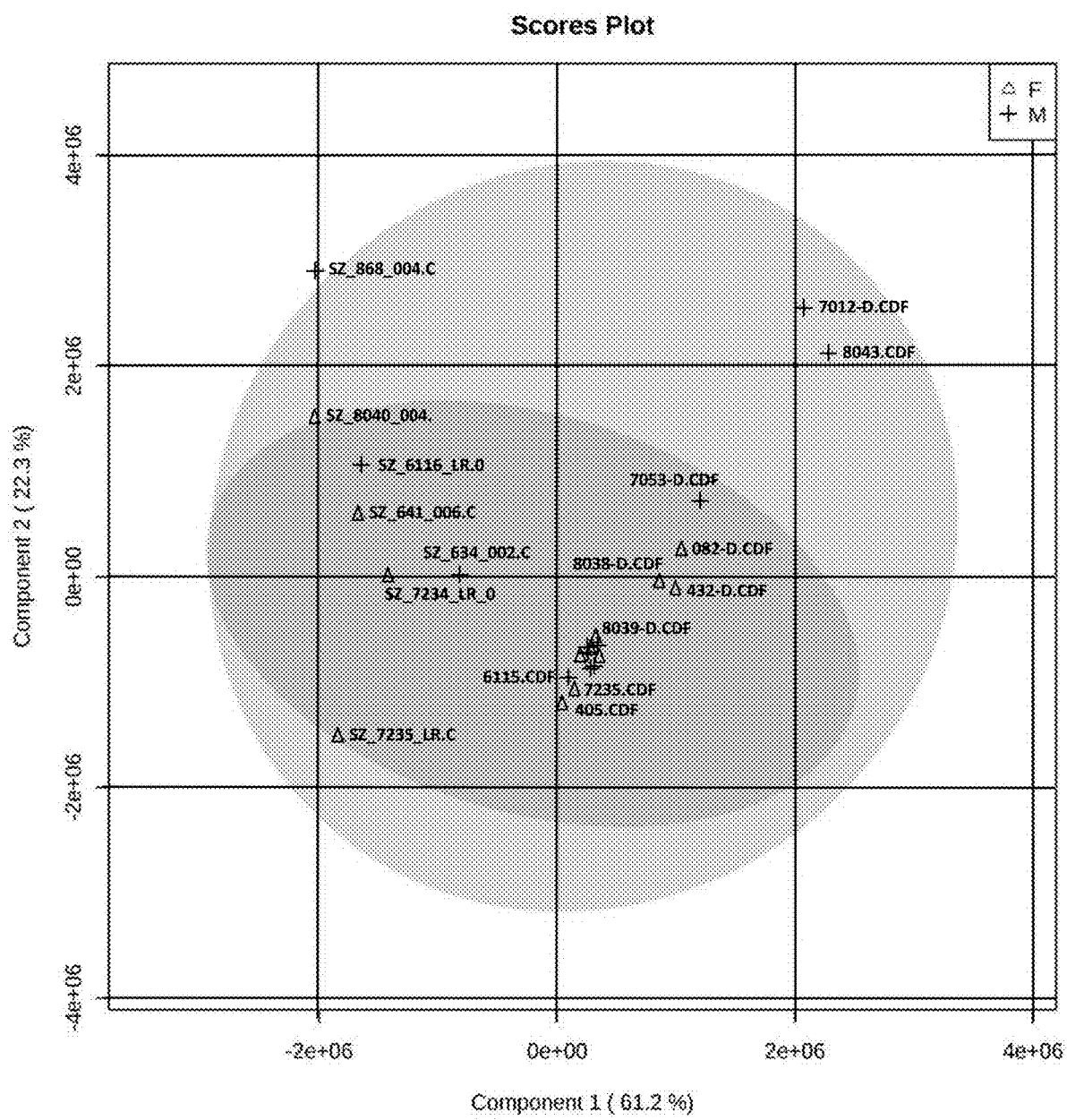
Figure 7A:
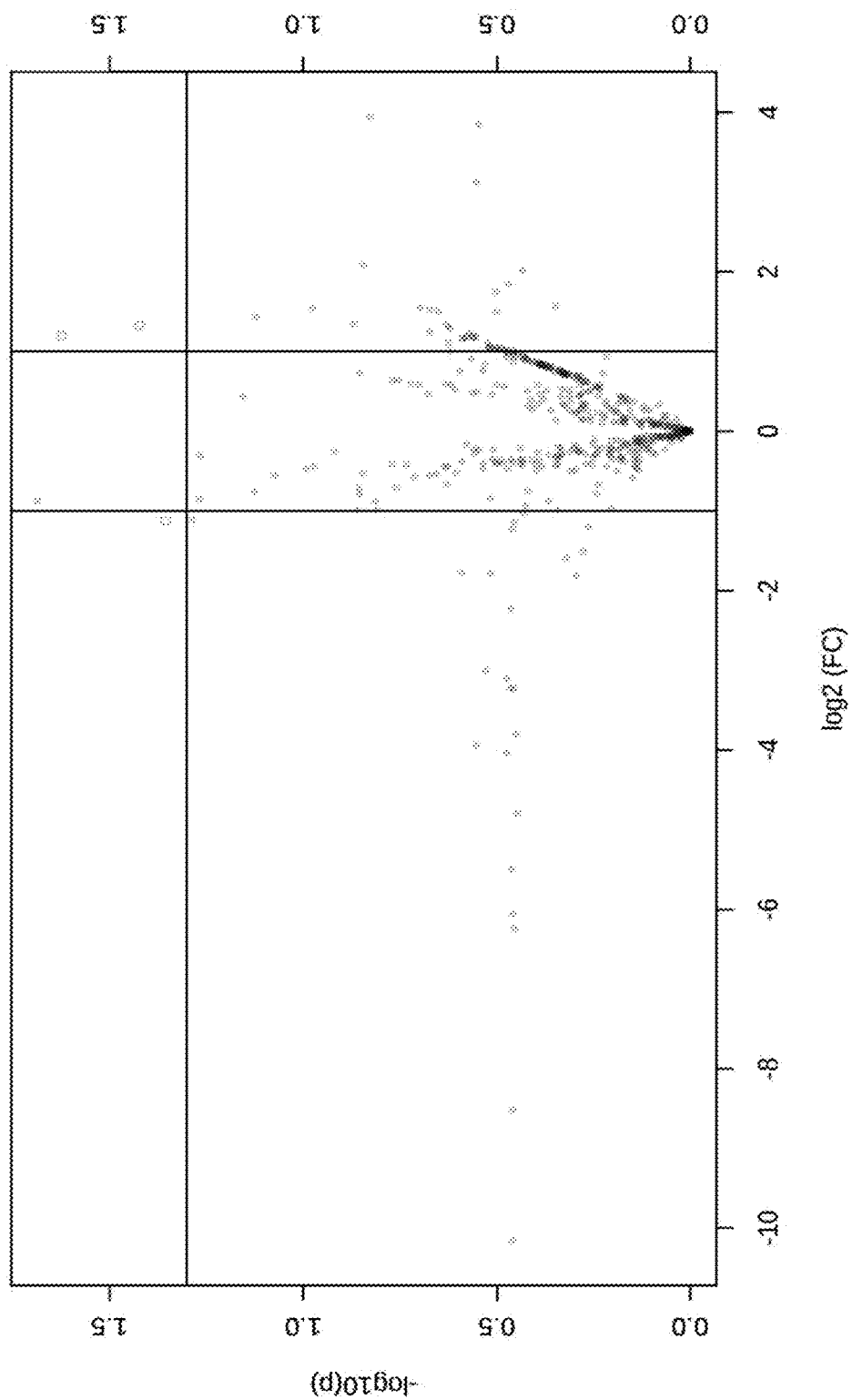
FIGS. 7A-7B show plots that can demonstrate that there were no significant differences in VOCs that were attributable to weight class (5.3-12.6 kg).
Figure 7B:
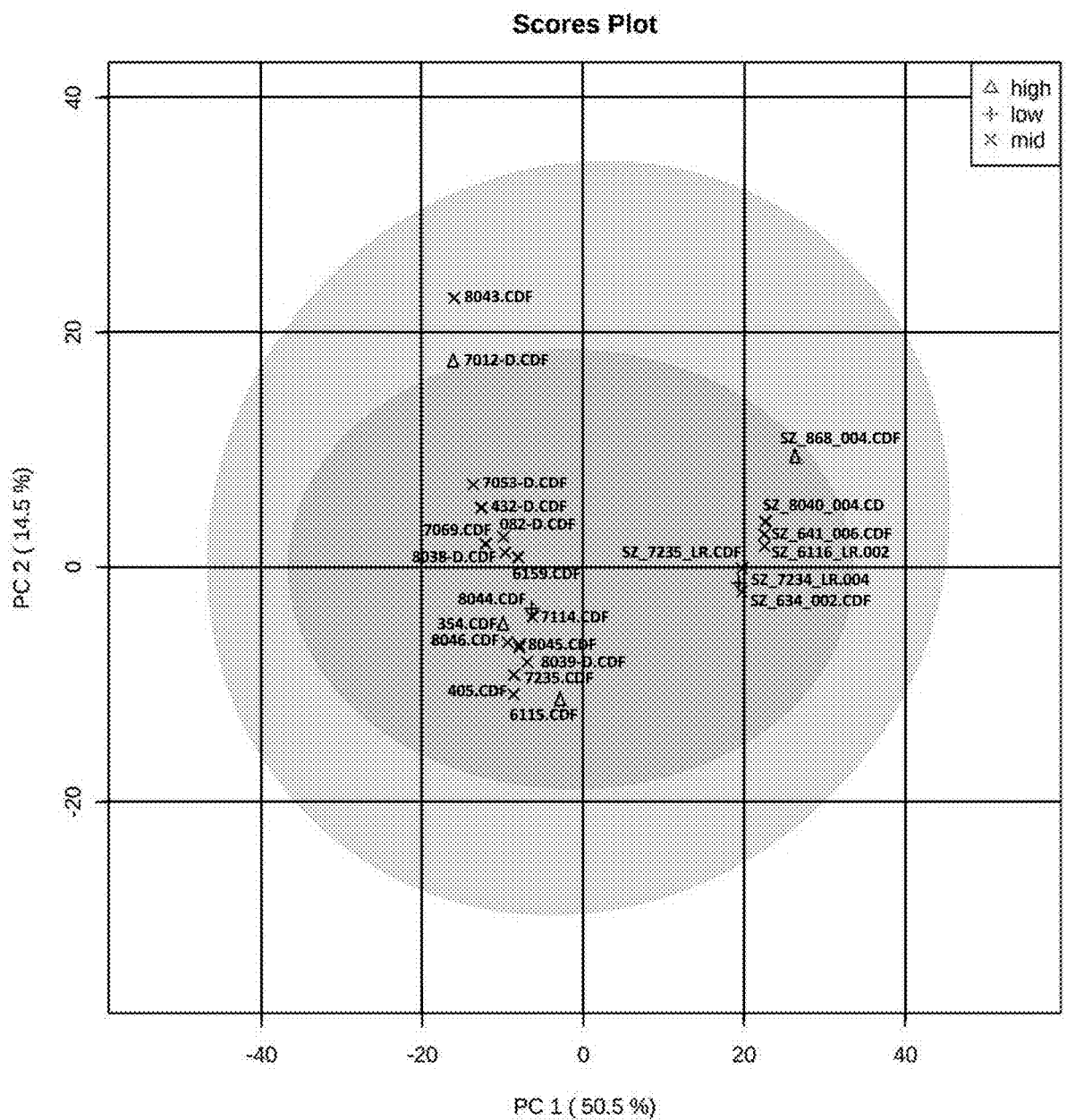
Figure 8A:
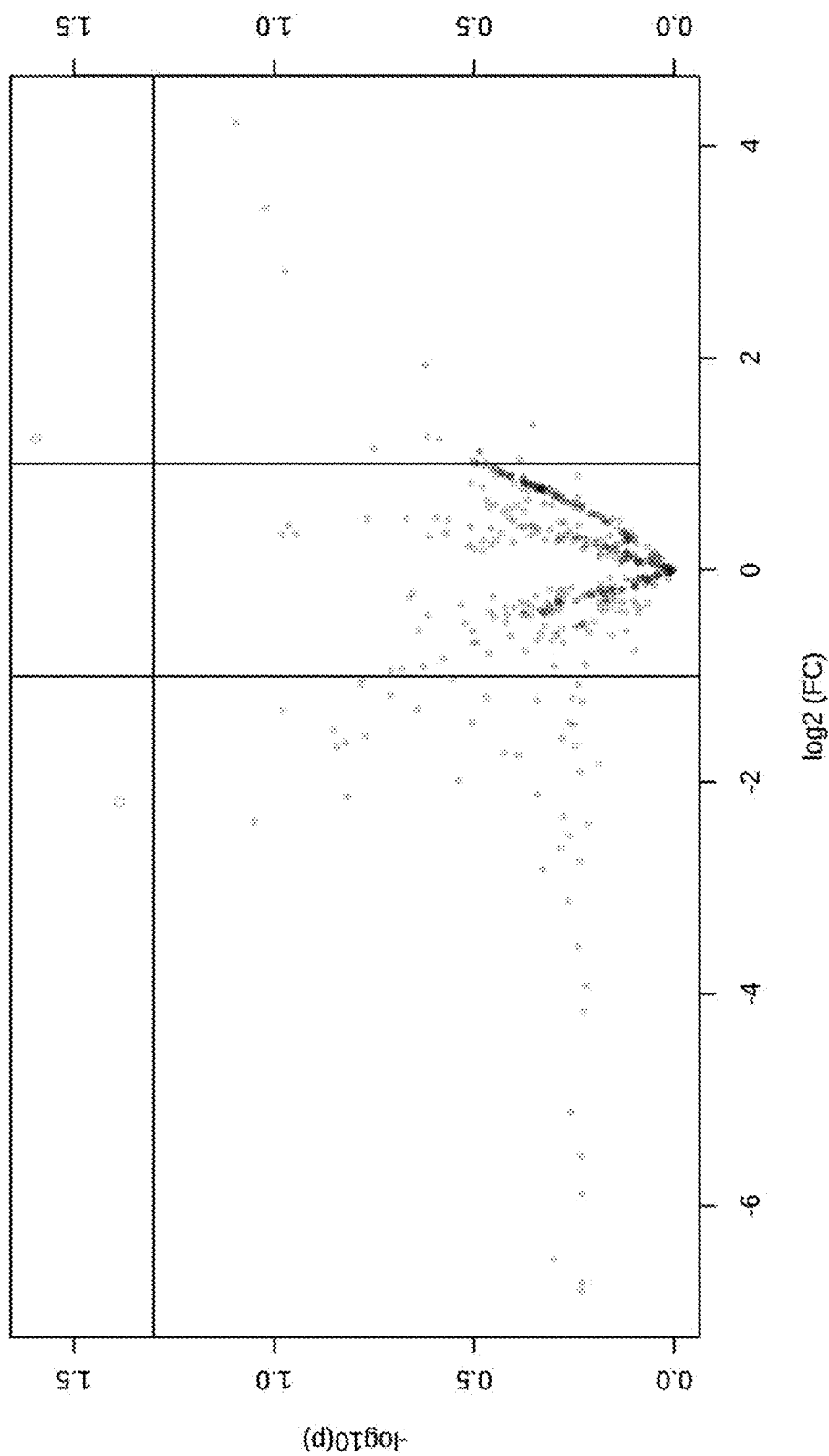
FIGS. 8A-8B show plots that can demonstrate no significant differences in VOCs were attributable to age.
Figure 8B:
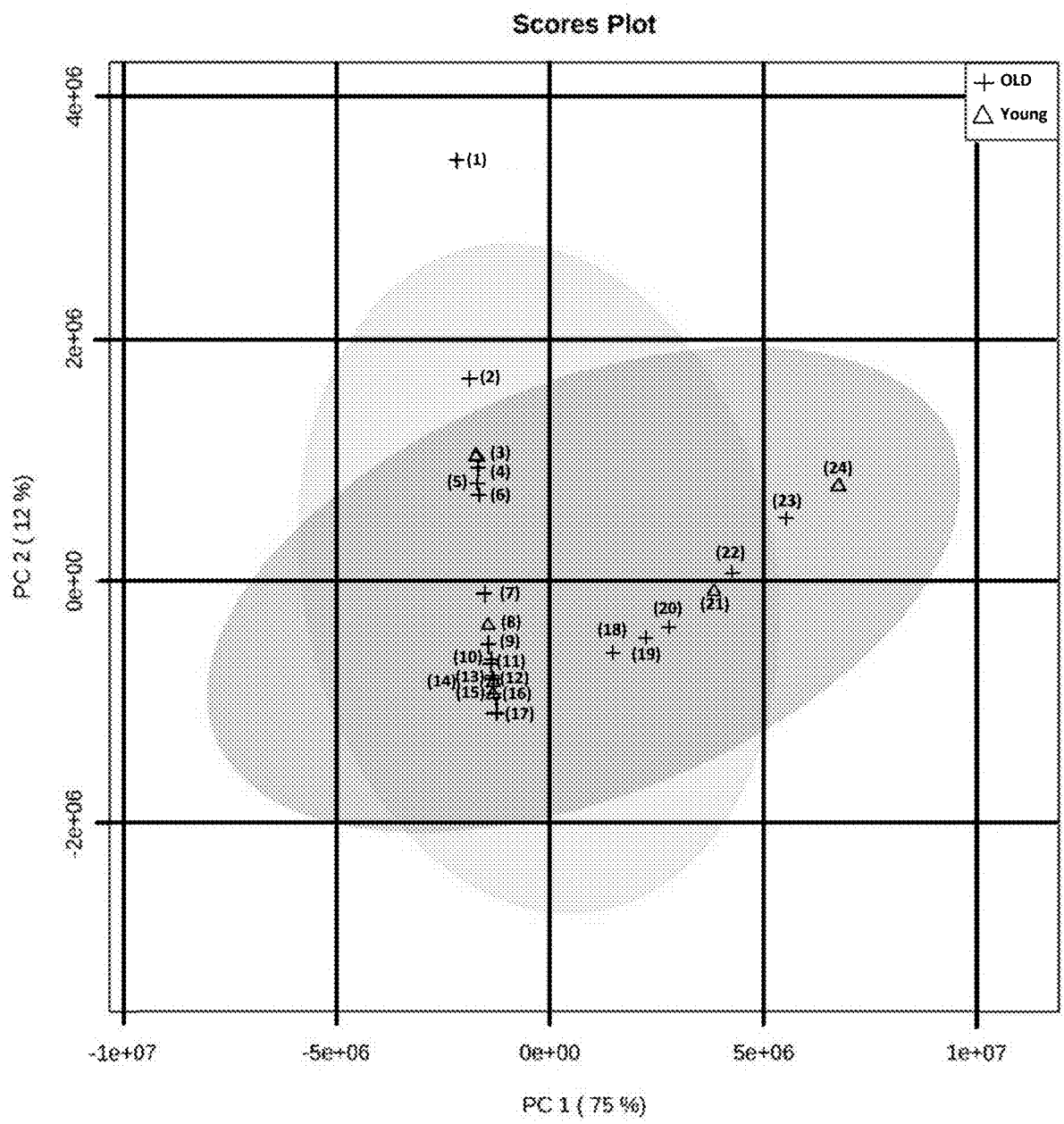

FIGS. 6A-6B show plots that can demonstrate no significant differences in VOCs were attributable to sex differences. A principle component analysis (PCA) was performed based on the sex of the dog. Normalizing the data to account for potential sex differences in the volume of exhalant did not alter the observed results. FIGS. 7A-7B show plots that can demonstrate that there were no significant differences in VOCs that were attributable to weight class (5.3-12.6 kg). Data by weight was analyzed using ANOVA and/or PCA analysis. FIGS. 8A-8B show plots that can demonstrate no significant differences in VOCs were attributable to age (young v. old).

Figure 9A:
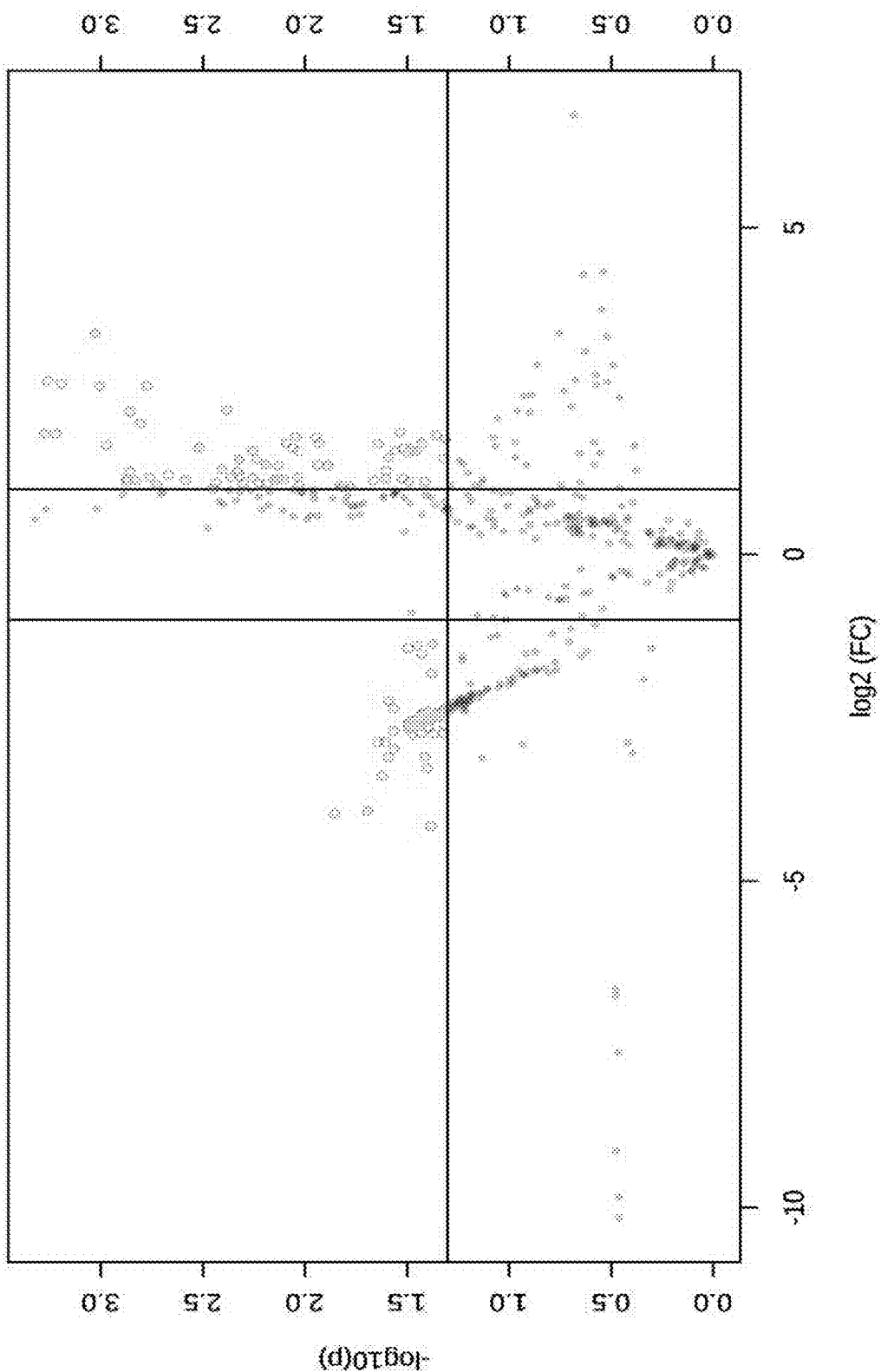
FIGS. 9A-9B show plots that can demonstrate that there are significantly more VOCs in canines infected with D. immitis (FIG. 9A) as compared to non-infected canines (FIG. 9B).
Figure 9B:
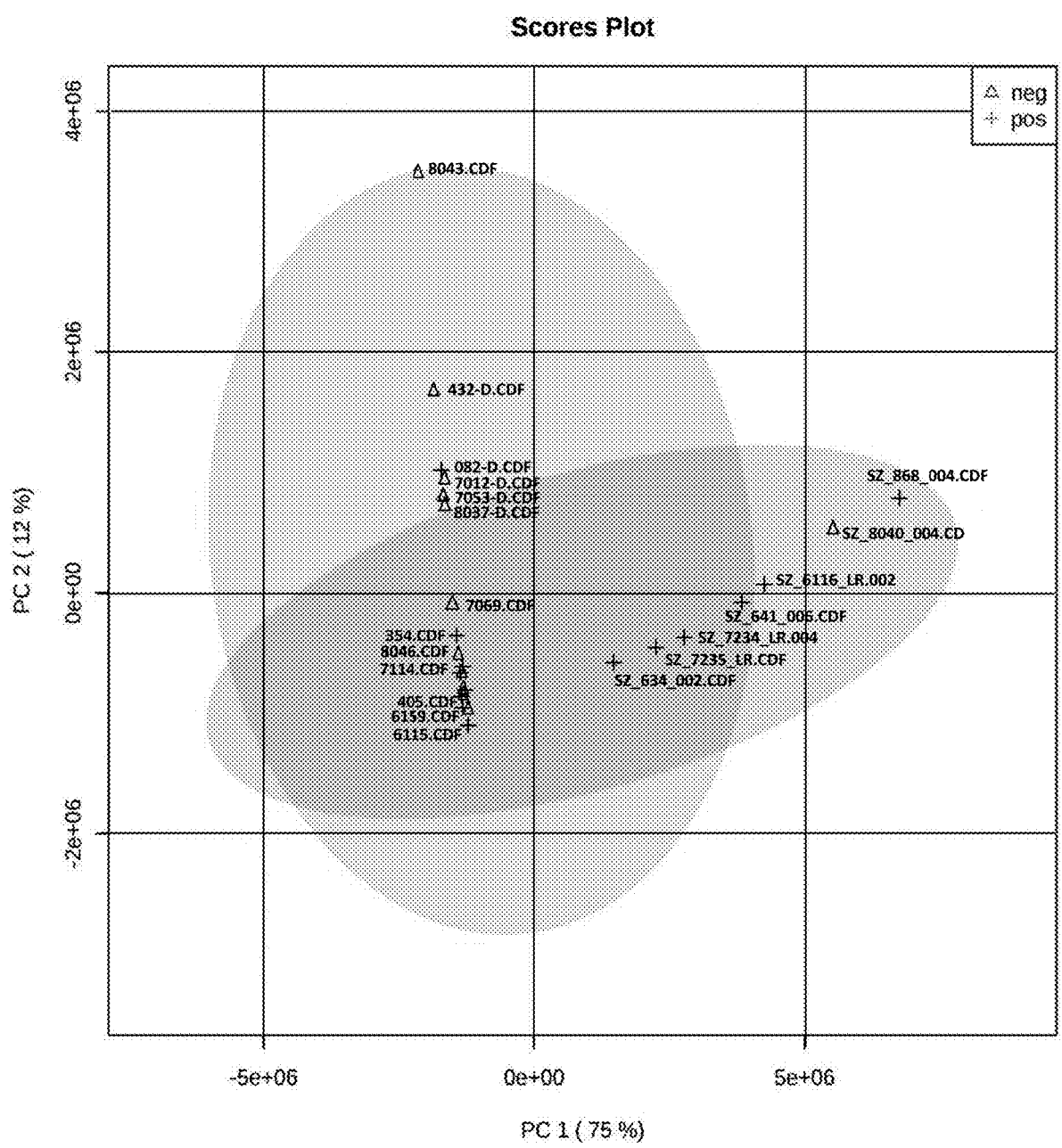

FIGS. 9A-9B show plots that can demonstrate that there are significantly more VOCs in canines infected with *D. immitis* (FIG. 9A) as compared to non-infected canines (FIG. 9B). With adjustment via ICR 56 peaks/compounds/features change with P<0.05. Using a FalseDiscoveryRate (FDR) of less than 0.05 (instead of p-value), 19 interesting features were observed. When the infection is changed to 4 groups and IQR and autoscaling were used, the PCA was more interesting. The ANOVA analysis with a p-value of 0.05 resulted in 53 peaks/compounds/features changing significantly (see e.g., Table 9).

TABLE 9

| | f.value | p.value | −log10(p) | FDR | Fisher's LSD |
|---|---|---|---|---|---|
| 232/108.2246 mz/1.43 min | 16.909 | 5.0729E−06 | 5.2947 | 0.0022625 | neg - early; neg - pos; neg - transplant |
| 416/92.2179 mz/1.45 min | 13.711 | 2.4427E−05 | 4.6121 | 0.0054471 | neg - early; neg - pos; neg - transplant |
| 380/153.5183 mz/2.67 min | 10.831 | 0.00012398 | 3.9066 | 0.018432 | neg - early; neg - pos; neg - transplant |
| 6/91.0714 mz/1.43 min | 10.209 | 0.00018167 | 3.7407 | 0.020128 | neg - early; neg - pos; neg - transplant |
| 387/106.1286 mz/1.49 min | 9.8658 | 0.00022565 | 3.6466 | 0.020128 | neg - early; neg - pos; neg - transplant |
| 324/120.9167 mz/2.91 min | 9.0808 | 0.00037603 | 3.4248 | 0.027952 | neg - early; neg - pos; neg - transplant |
| 350/90.9607 mz/3.83 min | 8.7468 | 0.00047053 | 3.3274 | 0.028254 | early - transplant; neg - pos; neg - transplant |
| 420/123.0680 mz/3.21 min | 8.3056 | 0.00063694 | 3.1959 | 0.028254 | early - transplant; neg - pos; neg - transplant |
| 64/160.1658 mz/3.94 min | 8.1885 | 0.00069112 | 3.1604 | 0.028254 | neg - pos; neg - transplant |
| 303/160.1201 mz/3.89 min | 7.9494 | 0.00081805 | 3.0872 | 0.028254 | neg - early; neg - pos; neg - transplant |
| 409/118.9414 mz/4.21 min | 7.9287 | 0.00083014 | 3.0808 | 0.028254 | early - pos; early - transplant; neg - pos; neg - transplant |
| 351/109.0858 mz/3.89 min | 7.9029 | 0.00084549 | 3.0729 | 0.028254 | neg - pos; neg - transplant |
| 353/159.6715 mz/3.95 min | 7.8787 | 0.00086019 | 3.0654 | 0.028254 | neg - pos; neg - transplant |
| 331/122.8530 mz/4.25 min | 7.7138 | 0.0009681 | 3.0141 | 0.028254 | neg - early; neg - pos; neg - transplant |
| 62/155.0464 mz/3.08 min | 7.6386 | 0.0010221 | 2.9905 | 0.028254 | neg - pos; neg - transplant |
| 404/95.0821 mz/3.79 min | 7.5636 | 0.0010792 | 2.9669 | 0.028254 | neg - pos; neg - transplant |
| 428/97.0643 mz/3.54 min | 7.5517 | 0.0010886 | 2.9631 | 0.028254 | neg - pos; neg - transplant |
| 352/123.0849 mz/3.93 min | 7.4638 | 0.0011606 | 2.9353 | 0.028254 | neg - pos; neg - transplant |
| 411/109.0661 mz/4.49 min | 7.4141 | 0.0012036 | 2.9195 | 0.028254 | neg - early; neg - pos; neg - transplant |
| 334/123.0466 mz/4.58 min | 7.1703 | 0.0014412 | 2.8413 | 0.031614 | early - transplant; neg - pos; neg - transplant |
| 270/97.0554 mz/2.79 min | 7.1269 | 0.0014886 | 2.8272 | 0.031614 | neg - early; neg - pos; neg - transplant |
| 401/139.2714 mz/2.58 min | 7.0096 | 0.0016253 | 2.7891 | 0.031737 | neg - early; neg - pos; neg - transplant |
| 146/116.9893 mz/3.94 min | 6.9366 | 0.0017172 | 2.7652 | 0.031737 | neg - pos; neg - transplant |
| 407/167.2459 mz/4.10 min | 6.8842 | 0.0017867 | 2.748 | 0.031737 | neg - pos; neg - transplant |

TABLE 9-continued

| | f.value | p.value | −log10(p) | FDR | Fisher's LSD |
|---|---|---|---|---|---|
| 368/143.0086 mz/3.08 min | 6.8763 | 0.0017973 | 2.7454 | 0.031737 | neg - early; neg - pos; neg - transplant |
| 347/168.0597 mz/2.79 min | 6.8382 | 0.0018501 | 2.7328 | 0.031737 | neg - early; neg - pos; neg - transplant |
| 427/159.1007 mz/3.38 min | 6.6969 | 0.0020609 | 2.6859 | 0.033619 | neg - pos; neg - transplant |
| 277/97.0679 mz/2.94 min | 6.6658 | 0.0021106 | 2.6756 | 0.033619 | early - transplant; neg - pos; neg - transplant |
| 329/164.9012 mz/4.43 min | 6.5886 | 0.00224 | 2.6498 | 0.034274 | neg - pos; neg - transplant |
| 231/102.9625 mz/1.43 min | 6.5514 | 0.0023054 | 2.6373 | 0.034274 | neg - early; neg - pos; neg - transplant |
| 393/115.0093 mz/3.94 min | 6.4396 | 0.0025146 | 2.5995 | 0.035147 | neg - pos; neg - transplant |
| 281/97.0841 mz/3.68 min | 6.4359 | 0.0025217 | 2.5983 | 0.035147 | early - transplant; neg - pos; neg - transplant |
| 446/155.0144 mz/3.16 min | 6.1672 | 0.0031153 | 2.5065 | 0.040256 | neg - pos; neg - transplant |
| 11/153.3913 mz/2.22 min | 6.1009 | 0.0032838 | 2.4836 | 0.040256 | neg - early; neg - pos; neg - transplant |
| 298/168.2153 mz/2.49 min | 6.0763 | 0.003349 | 2.4751 | 0.040256 | neg - pos; neg - transplant |
| 60/118.9750 mz/3.00 min | 6.0444 | 0.0034354 | 2.464 | 0.040256 | neg - early; neg - pos; neg - transplant |
| 282/160.4001 mz/4.45 min | 6.0063 | 0.003542 | 2.4508 | 0.040256 | neg - pos; neg - transplant |
| 445/154.5036 mz/3.17 min | 6.0015 | 0.0035556 | 2.4491 | 0.040256 | early - transplant; neg - pos; neg - transplant |
| 12/140.9394 mz/2.26 min | 5.9718 | 0.0036414 | 2.4387 | 0.040256 | neg - early; neg - pos; neg - transplant |
| 222/146.9607 mz/6.56 min | 5.967 | 0.0036553 | 2.4371 | 0.040256 | early - transplant; neg - pos; neg - transplant; pos - transplant |
| 429/111.9252 mz/4.39 min | 5.9325 | 0.0037583 | 2.425 | 0.040256 | neg - pos; neg - transplant |
| 16/132.9500 mz/2.64 min | 5.9186 | 0.0038007 | 2.4201 | 0.040256 | neg - early; neg - pos; neg - transplant |
| 426/98.2304 mz/3.37 min | 5.8921 | 0.0038828 | 2.4109 | 0.040256 | neg - pos; neg - transplant |
| 370/131.0112 mz/3.93 min | 5.8541 | 0.0040041 | 2.3975 | 0.040256 | neg - pos; neg - transplant |
| 197/166.9179 mz/2.65 min | 5.8365 | 0.0040617 | 2.3913 | 0.040256 | neg - early; neg - pos; neg - transplant |
| 273/140.5260 mz/3.71 min | 5.7787 | 0.0042568 | 2.3709 | 0.041273 | neg - pos; neg - transplant |
| 320/108.8446 mz/2.54 min | 5.7496 | 0.0043589 | 2.3606 | 0.041363 | neg - early; neg - pos; neg - transplant |
| 413/110.7801 mz/4.76 min | 5.719 | 0.0044693 | 2.3498 | 0.041527 | neg - pos; neg - transplant |
| 82/126.7050 mz/3.68 min | 5.6272 | 0.0048185 | 2.3171 | 0.043858 | neg - pos; neg - transplant |
| 424/111.4964 mz/3.26 min | 5.4948 | 0.0053754 | 2.2696 | 0.047948 | early - transplant; neg - pos; neg - transplant |
| 115/119.0286 mz/2.64 min | 5.4416 | 0.0056185 | 2.2504 | 0.049134 | neg - early; neg - pos; neg - transplant |
| 335/158.4309 mz/4.68 min | 5.3981 | 0.0058256 | 2.2347 | 0.049966 | neg - pos; neg - transplant |

Figure 10:
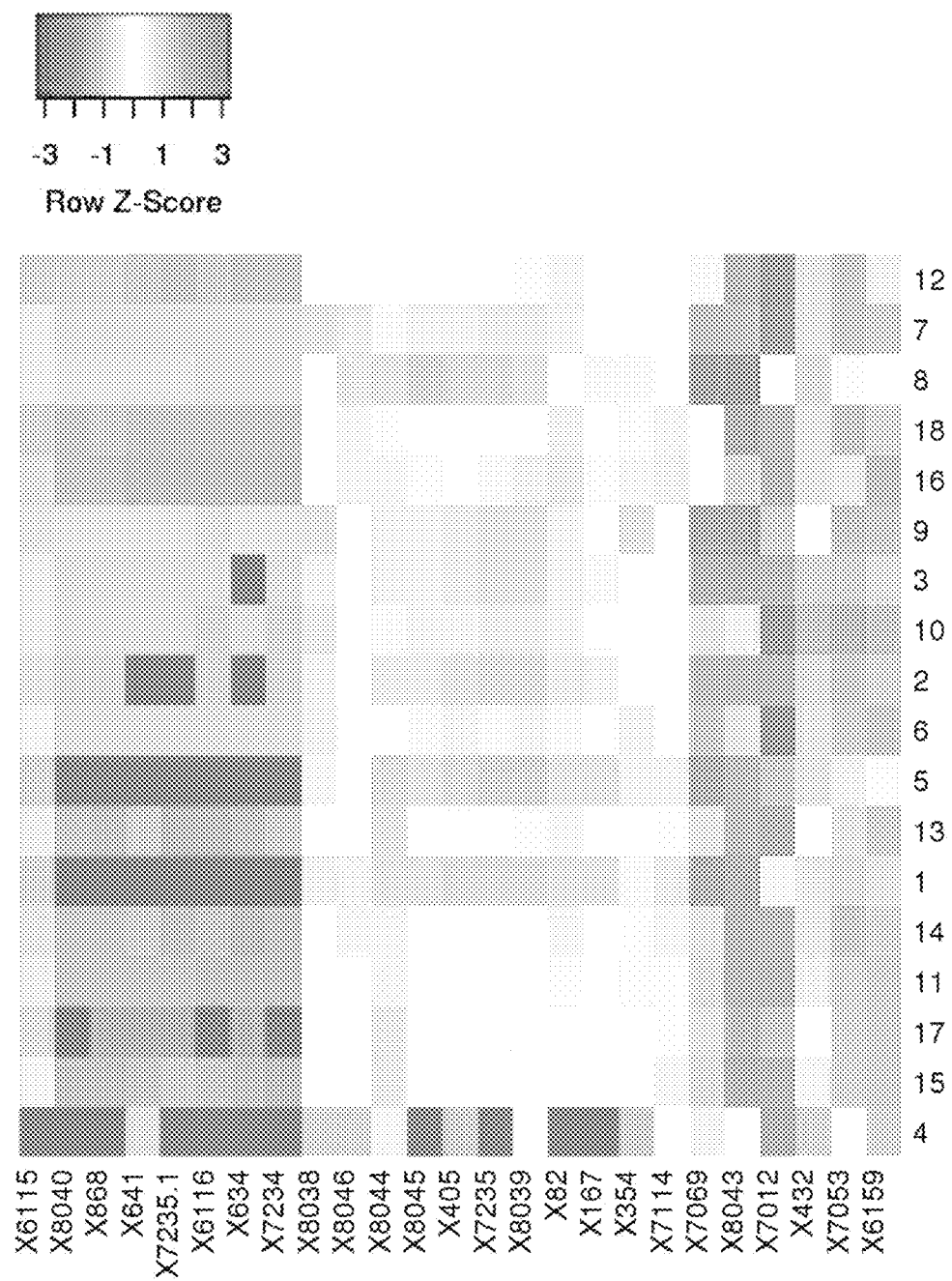
FIG. 10 shows a gas chromatography array heat map that can demonstrate 19 distinct groupings when the differential significant features separating D. immitis infected individuals from non-infected individuals. See also Table 2.
Figure 11A:
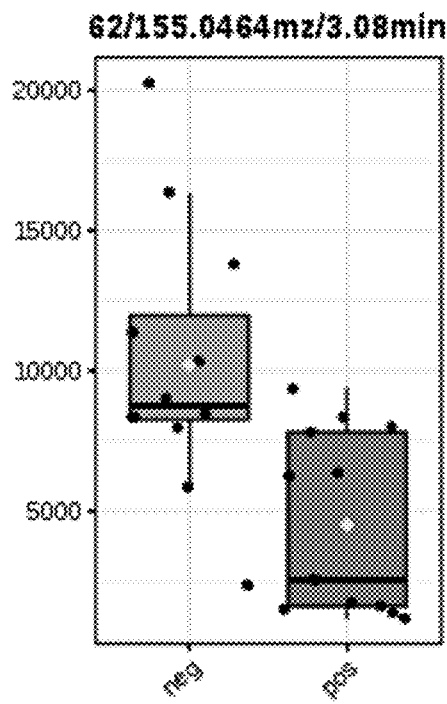
FIGS. 11A-11D show box and whisker plots that can demonstrate the data plots for the data featured in Table 4 and indicate the features are all greater in the D. immitis negative canines (neg) as compared to positive (pos) canines.
Figure 11B:
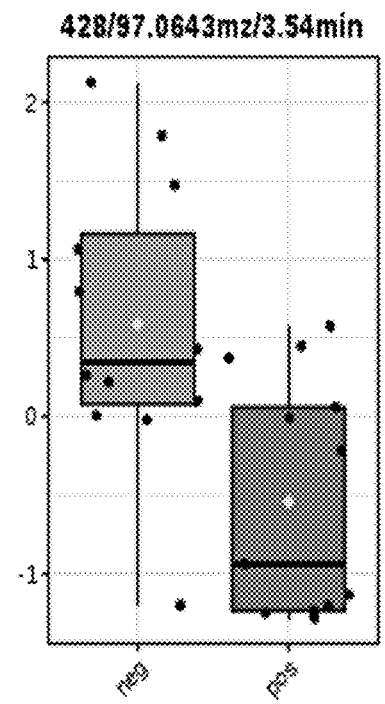
Figure 11C:
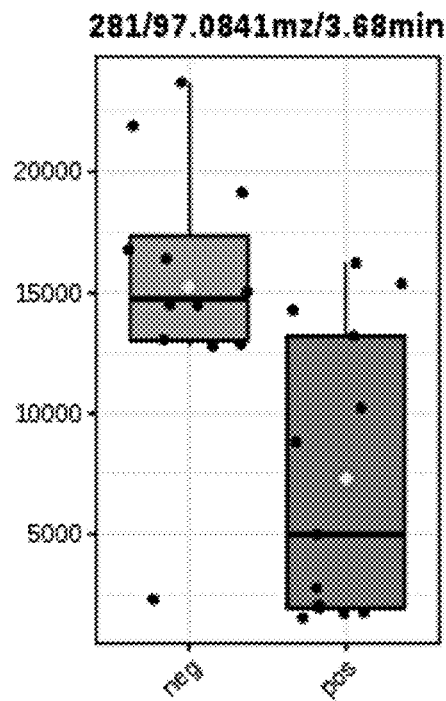
Figure 11D:
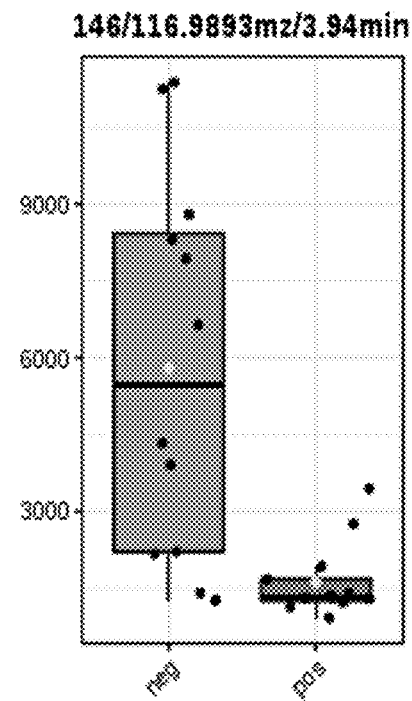

FIG. 10 shows a gas chromatography array heat map that can demonstrate 19 distinct groupings when the differential significant features separating *D. immitis* infected individuals from non-infected individuals. See also Table 2. Values were determined using a metaboanalyst and IQR normalization and the values shown in Table 2 were assembled with an FDR less than 0.05. Numbers 370, 352, 64, 146, 393, and 408 were observed at very similar retention times, were observed in all spectra. As shown in Table 3, about 9 compounds were observed to differentiate samples from infected and non-infected subjects because ions observed originated from the same compound(s). Table 2 reports the identities of the compounds with AMDIS/NIST 2.0. Spectra and identities are organized by retention time and a summary of identity information by class and compound is shown in Table 2.

FIGS. 14-23 shows a representative GC-MS spectra at the various retention times as indicated.

TABLE 2

Differential Significant Features Sorted by Masses and Retention Time

| | ion | retention time | FC | p.adjusted |
|---|---|---|---|---|
| 232 | 108.2246 mz | 1.43 min | 3.5965 | 0.040847 |
| 62 | 155.0464 mz | 3.08 min | 2.262 | 0.040847 |

TABLE 2-continued

Differential Significant Features Sorted by Masses and Retention Time

| | ion | retention time | FC | p.adjusted |
|---|---|---|---|---|
| 427 | 159.1007 mz | 3.38 min | 10.426 | 0.040847 |
| 428 | 97.0643 mz | 3.54 min | 2.1943 | 0.048212 |
| 281 | 97.0841 mz | 3.68 min | 2.087 | 0.04092 |
| 303 | 160.1201 mz | 3.89 min | 5.9586 | 0.040847 |
| 351 | 109.0858 mz | 3.89 min | 2.1989 | 0.040847 |
| 370 | 131.0112 mz | 3.93 min | 4.0316 | 0.040847 |
| 352 | 123.0849 mz | 3.93 min | 2.4037 | 0.040847 |
| 64 | 160.1658 mz | 3.94 min | 6.1105 | 0.040847 |
| 146 | 116.9893 mz | 3.94 min | 3.586 | 0.040847 |
| 393 | 115.0093 mz | 3.94 min | 3.1877 | 0.040847 |
| 353 | 159.6715 mz | 3.95 min | 6.2927 | 0.040847 |
| 408 | 170.8526 mz | 4.13 min | 5.9794 | 0.040847 |
| 329 | 164.9012 mz | 4.43 min | 2.3253 | 0.041659 |
| 282 | 160.4001 mz | 4.45 min | 4.5273 | 0.040847 |
| 411 | 109.0661 mz | 4.49 min | 2.1721 | 0.040847 |
| 334 | 123.0466 mz | 4.58 min | 2.2301 | 0.040847 |

As shown in Table 3, nine distinct compounds were observed to separate infected from non-infected animals.

TABLE 3

Compounds Separating *D. immitis* Infected and Non-infected Canines

| Retention time (min) | Compound Classification | Example Compound |
|---|---|---|
| 1.43 | Aromatic hydrocarbon | Ortho xylene |
| 3.08 | Monoterpene | p-Menthane-1,2,3-triol |
| 3.36 | Alkyl alcohol | 3,7,11-trimethyl-1-Dodecanol |
| 3.54 | Cyclopentanone | 2-ethyl-Cyclohexanone |
| 3.68 | Aziridine | 2-mehtyl-2-(2,2,4,4,6,6,-hexamethylheptyl)-Aziridine |
| 3.94 | Alkane hydrocarbon | 1,2,3,6,7,8,8a,8b-octahydro-, trans-Biphenylene |
| 4.13 | Alkane hydrocarbon | 2,6,10-trimethyl-Tetradecane |
| 4.45 | Phenol | 5,6,6-Trimethyl-5-(3-oxobut-1-enyl)-1-oxaspiro[2.5]octan-4-one |
| 4.58 | Ketone | 5,5-Dibutylnonane |

Example 3—Using VOCs from Canine Exhalant to Detect *D. immitis* Positive Canines Two sample sets of data was used for This Example (Data Set A and Data Set B). For both, canine exhalant samples for VOC analysis were collected using the collection methodology and GC analysis for VOCs as described in Example 1. Table 4 summarizes the similarity of GC spectra obtained from samples between Data Set A and Data Set B. * indicates spectra which exhibit more than 2 similar masses (within 0.5 amu). FIGS. 11A-11D show the data plots for the features with * in Table 4 and demonstrate that these features are all greater in the *D. immitis* negative canines. Although there can be some overlap in the groups shown by this data, there are at least 9 unique compounds that can be used to separate *D. immitis* positive and negative canines (see e.g., Example 21).

TABLE 4

Similarity of GC spectra from different data sets at two different time periods

| Retention time (min) Data set A | Retention time (min) Data set B | Qualitative number of matching masses in spectra |
|---|---|---|
| 1.43 | 6.71 | 0 of 6 |
| 3.08* | 4.73* | 6 of 12* |
| 3.36 | 2.02 | 0 of 9 |
| 3.54* | 3.83* | 9 of 21* |
| 3.68* | 3.79* | 9 of 17* |
| 3.89 | 7.24 | 0 of 5 |
| 3.94* | 7.58* | 3 of 7* |
| 4.13 | 4.73 | 0 of 20 |
| 4.45 | 7.21 | 0 of 20 |
| 4.58 | 5.34 | 2 of 10 |

Figure 12A:
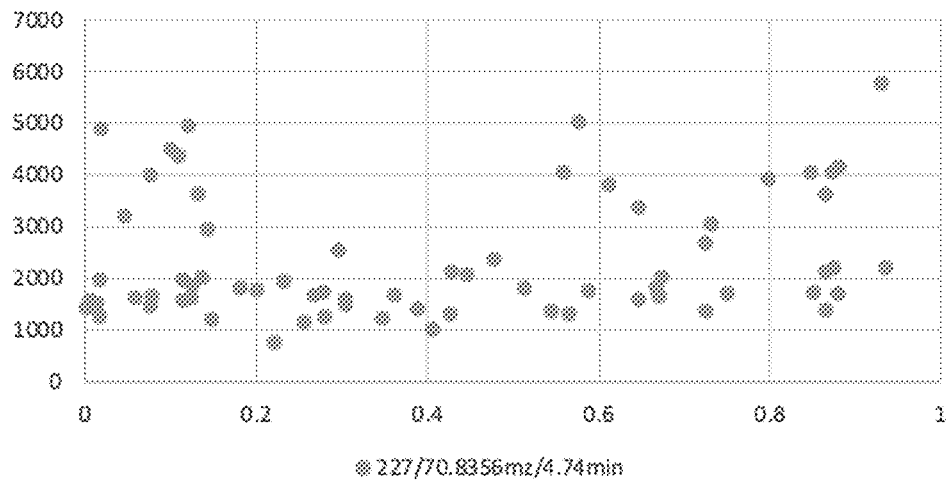
FIGS. 12A-12C show graphs created using similar features in the Group B data corresponding to the 3.08 min retention time in the Group A data. The x-axis of each graph is a random number that has been assigned to each sample. There is more than one feature in the data which corresponds to the Group A data, with the features being graphed separately. Zero values have been imputed very small values (typically 1). The graphs can demonstrate correlations among the different masses at a given retention time.
Figure 12B:
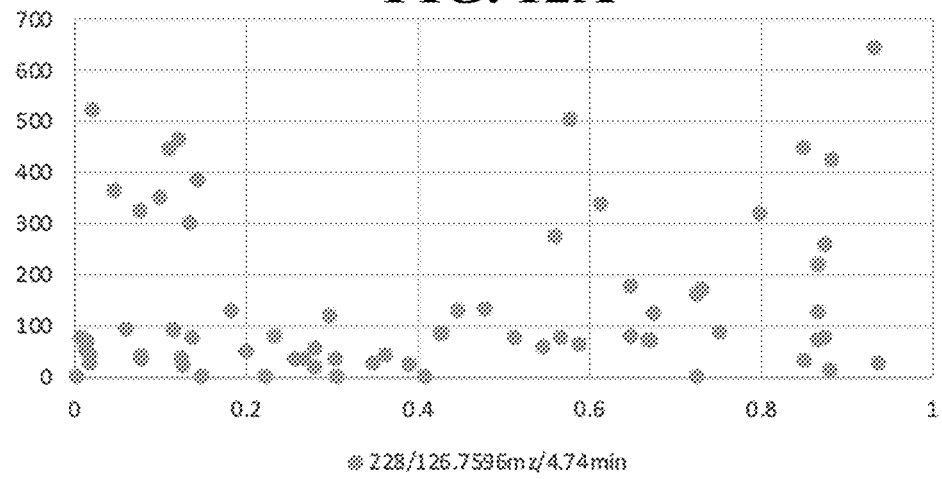
Figure 12C:
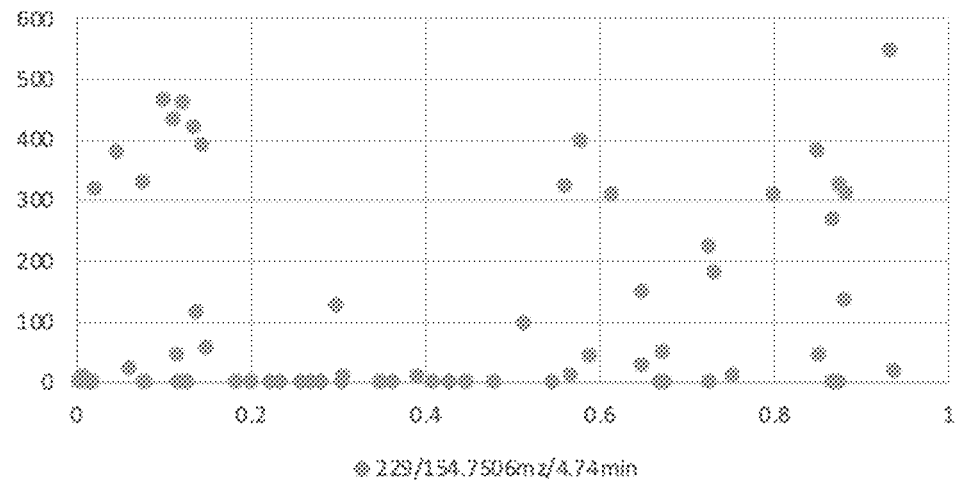
Figure 14:
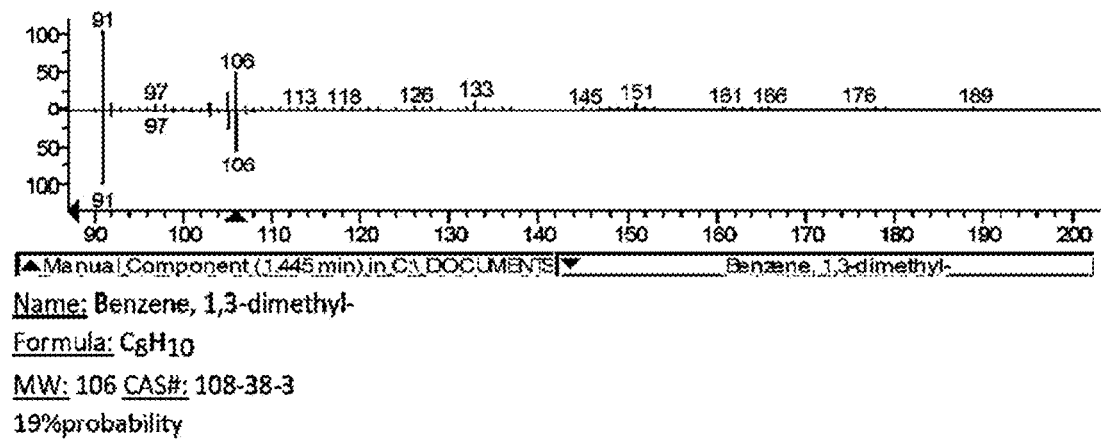
FIG. 14 shows a representative GC-MS spectra at retention time 1.43 minutes.
Figure 15A:
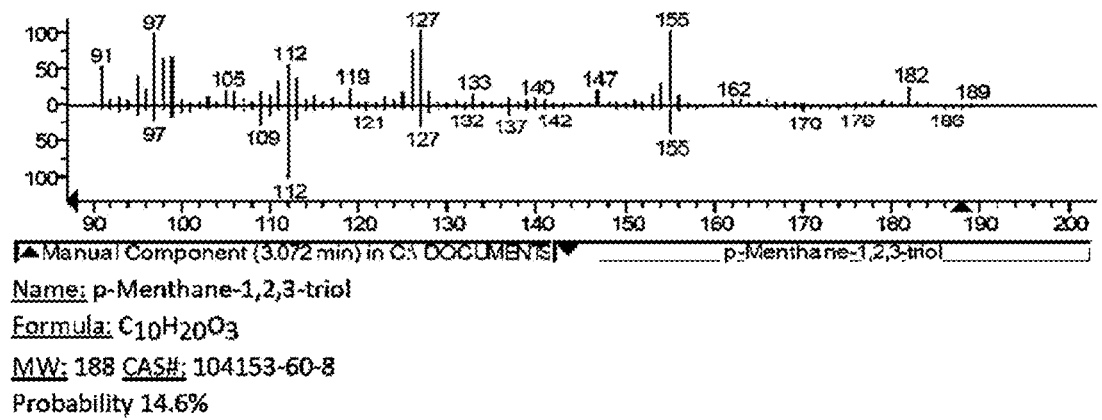
FIGS. 15A-15B show representative raw spectra (FIG. 15A) and spectra with the neighboring peak subtracted (FIG. 15B) at retention time 3.08 minutes.
Figure 15B:
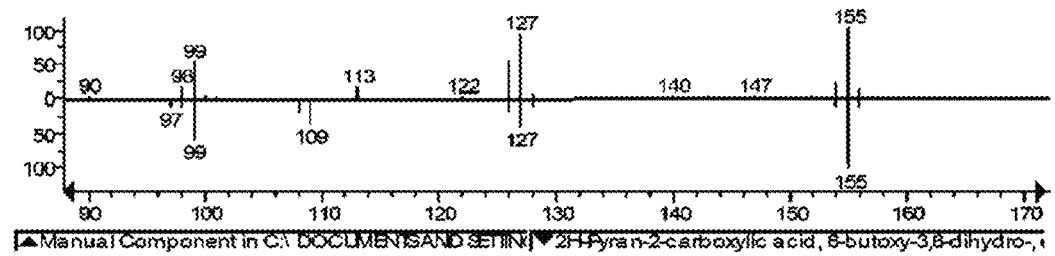
Figure 16A:
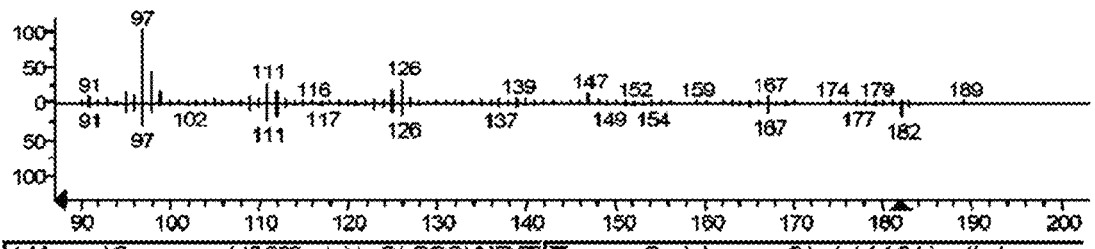
FIGS. 16A-16B show representative GC-MS spectra at retention time 3.38 minutes.
Figure 16B:
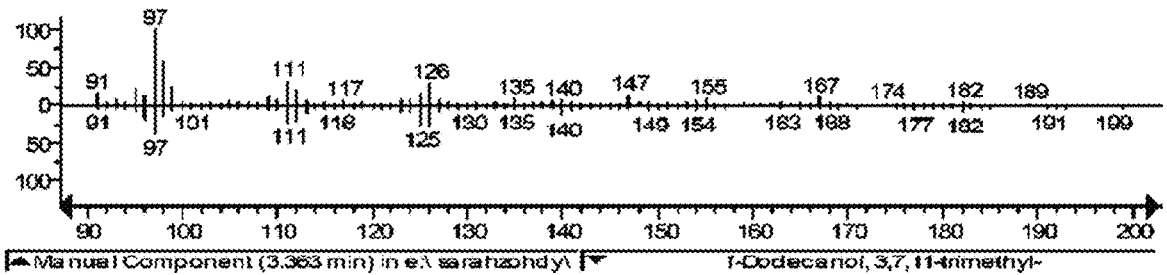
Figure 17:
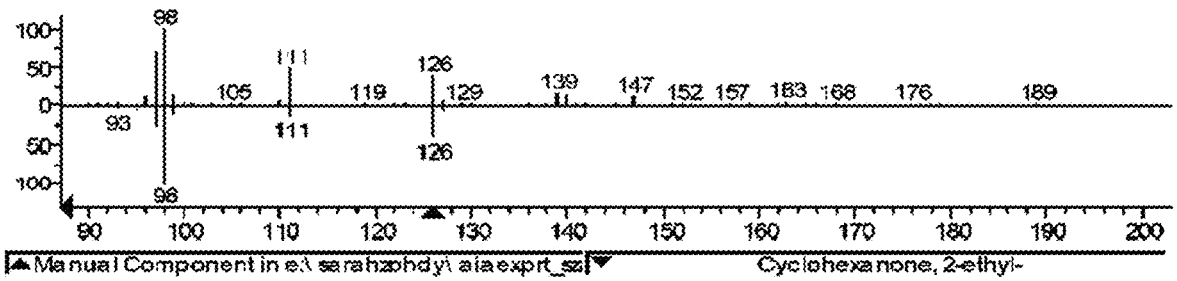
FIG. 17 shows a representative GC-MS spectra at retention time 3.54 minutes.
Figure 18:
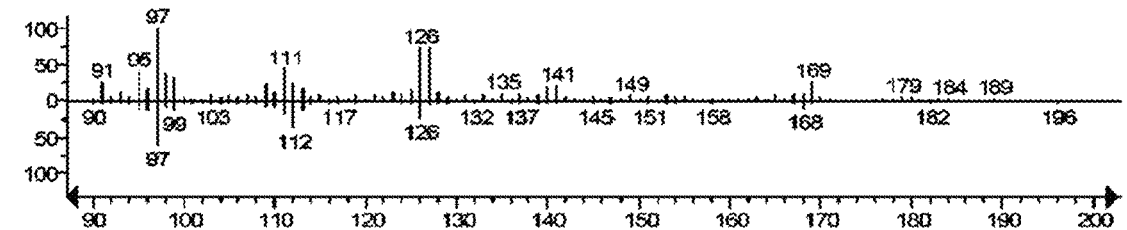
FIG. 18 shows a representative GC-MS spectra at retention time 3.68 minutes.
Figure 19:
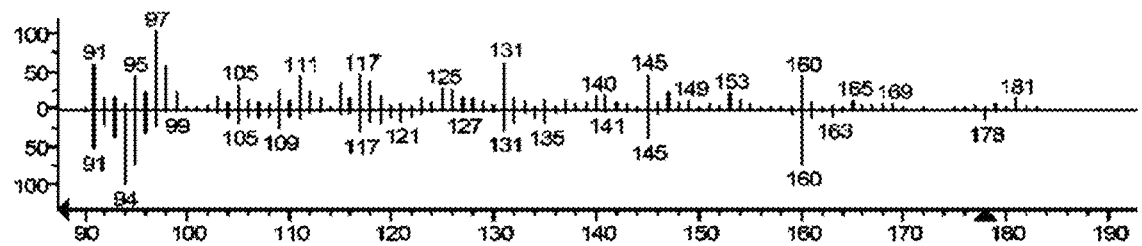
FIG. 19 shows a representative GC-MS spectra at retention time 3.89 minutes.
Figure 20A:
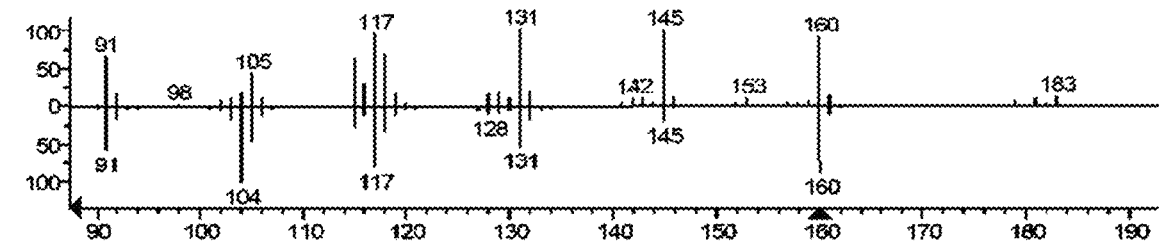
FIGS. 20A-20B show representative GC-MS spectra at retention time 3.95 minutes.
Figure 20B:
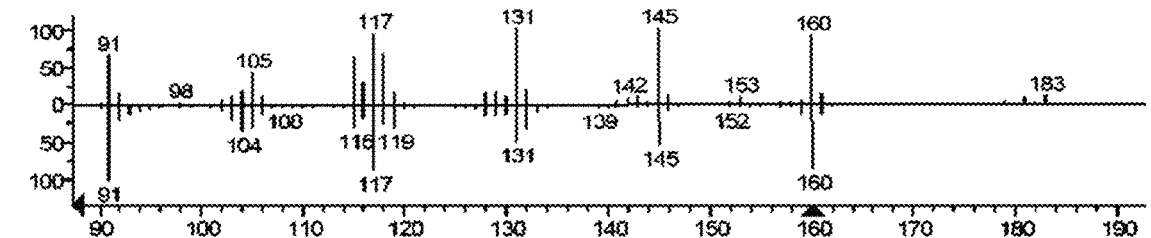
Figure 21A:
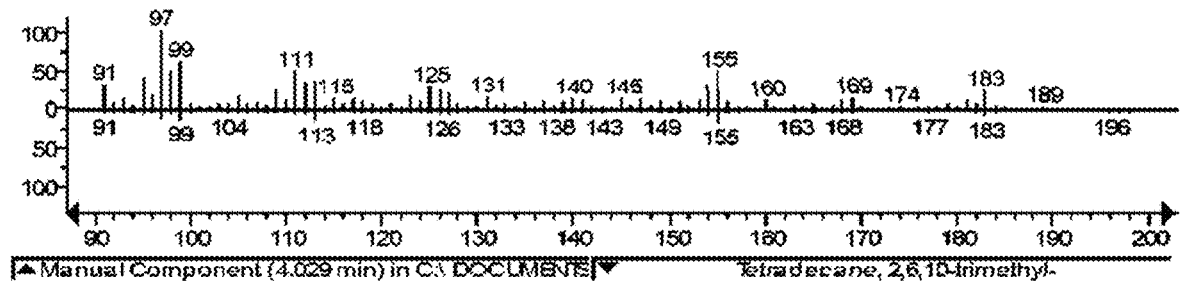
FIGS. 21A-21B show representative GC-MS spectra at retention time 4.13 minutes.
Figure 21B:
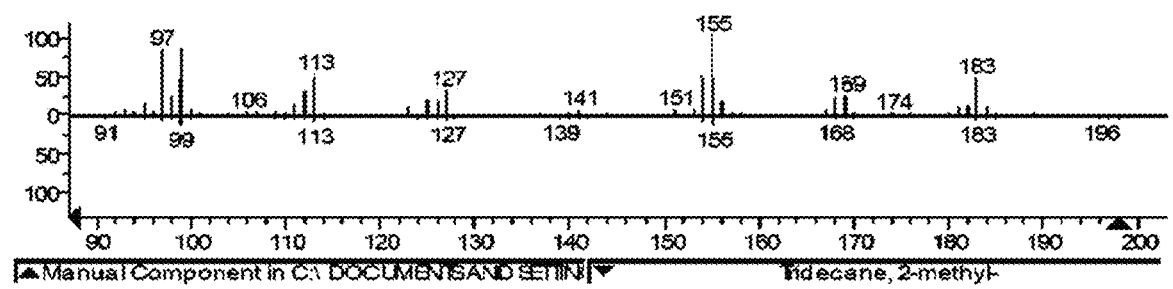
Figure 22A:
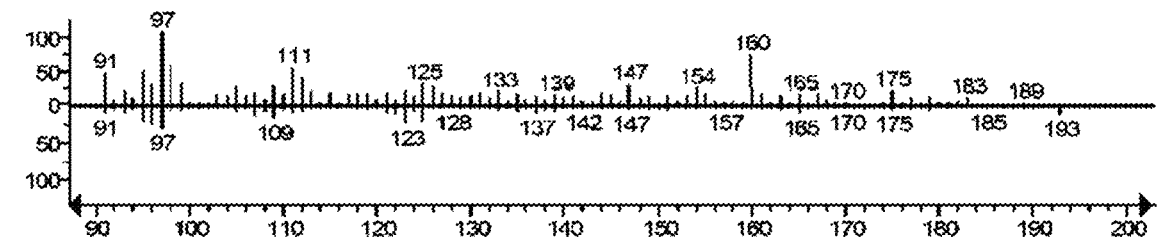
FIGS. 22A-22B show representative raw spectra (FIG. 22A) and spectra with the neighboring peak subtracted (FIG. 22B) at retention time 4.45 minutes.
Figure 22B:
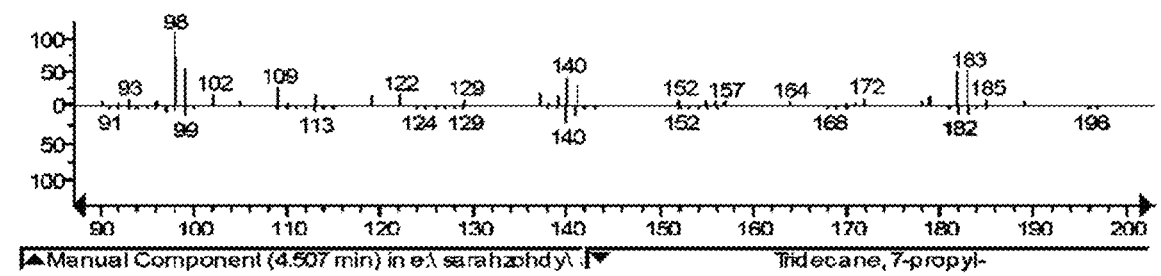
Figure 23:
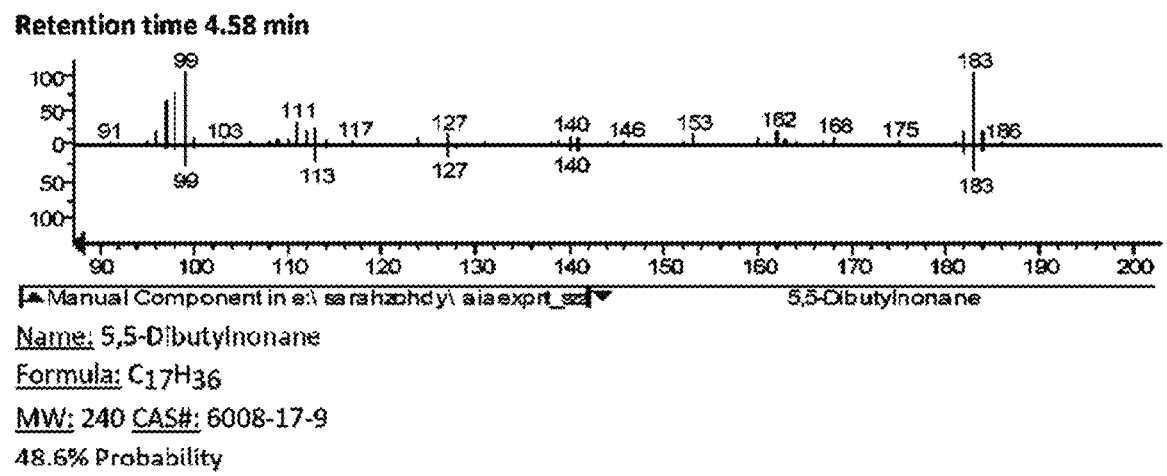
FIG. 23 shows a representative GC-MS spectra at retention time 4.58 minutes.

FIGS. 12A-12C show graphs that have been generated from the similar features identified from Data Set B corresponding to the 3.08 minute retention time in Data Set A. The X-axis in these graphs represents a random number that has been assigned to the samples. There is more than one feature in Data set B that correlates to Data set A. For clarity, the features have been graphed separately (i.e., each graph of 12A-12C corresponds to a different feature) to allow for the determination of correlations that exist amongst the different masses at the same 3.08 minute retention time. Tables 5-8 provides the sample names corresponding to the samples in the highest quartile in FIGS. 12A-12C (which should be *D. immitis* negative samples) and those in the lowest quartile in FIGS. 12A-12C (which should be *D. immitis* positive samples). FIGS. 12A-12C and Tables 5-8 demonstrate how the data can be quickly summarized into potentially positive and negative dogs (organize into high and low quartiles).

TABLE 5

Summary of high (negative) and low (positive) samples for feature at 3.08 min in Data Set A

| Data Name | Sample Name | 227/70.8356 mz/ 4.74 min | 228/126.7596 mz/ 4.74 min | 229/154.7506 mz/ 4.74 min |
|---|---|---|---|---|
| Above highest Quartile, less than highest Quartile | | | | |
| SZ_21_009.CDF | 21 | 5754.523 | 645.77 | 547.693 |
| SZ_26_006.CDF | 26 | 5023.088 | 504.6555 | 398.5235 |
| SZ_13_008.CDF | 13 | 4960.994 | 466.206 | 462.29 |
| SZ_18_011.CDF | 18 | 4891.803 | 524.9655 | 321.174 |
| SZ_6_009.CDF | 6 | 4499.268 | 353.179 | 466.243 |
| SZ_15_012.CDF | 15 | 4376.842 | 446.2485 | 434.455 |
| SZ_5_005.CDF | 5 | 4155.86 | 425.7955 | 314.21 |
| SZ_7_010.CDF | 7 | 4057.997 | 277.1505 | 324.6895 |
| SZ_2_012.CDF | 2 | 4056.913 | 261.332 | 327.9315 |
| SZ_27_015.CDF | 27 | 4052.896 | 449.924 | 383.0425 |
| SZ_24_004.CDF | 24 | 4003.613 | 326.6225 | 330.9625 |
| SZ_4_013.CDF | 4 | 3919.824 | 321.875 | 310.2075 |

TABLE 5-continued

Summary of high (negative) and low (positive) samples for feature at 3.08 min in Data Set A

| Data Name | Sample Name | 227/70.8356 mz/ 4.74 min | 228/126.7596 mz/ 4.74 min | 229/154.7506 mz/ 4.74 min |
|---|---|---|---|---|
| SZ_1_002.CDF | 1 | 3810.525 | 340.0065 | 310.215 |
| SZ_A23_SLOWER_GRAD_009.CDF | A23 | 3637.765 | 302.775 | 422.4085 |
| SZ_POST_LEVY_NEWRAMP_010.CDF | PostLevy | 3625.488 | 221.8565 | 271.0755 |
| SZ_AD55_JS_NEWRAMP3009.CDF | AD55 | 3362.805 | 179.97 | 150.864 |
| SZ_VALVE22_003.CDF | Valve22 | 3213.003 | 366.347 | 381.5165 |
| Below Lowest Quartile, greater than Lowest Quartile | | | | |
| SZ_D12_SLOWERGRAD_010.CDF | D12 | 1519.19 | 69.7585 | 1 |
| SZ_AD11_SLOWERGRAD_007.CDF | AD11 | 1497.148 | 35.871 | 1 |
| SZ_AD49_L2_011.CDF | AD49 | 1478.675 | 42.141 | 1 |
| SZ_AD48_LS_004.CDF | AD48 | 1440.205 | 1 | 1 |
| SZ_AD1_MS_012.CDF | AD1 | 1434.589 | 51.8715 | 1 |
| SZ_A15_JS_SLOWERGRAD012.CDF | A15 | 1427.738 | 26.4 | 11.517 |
| SZ_A20_JS_005.CDF | A20 | 1391.13 | 74.227 | 1 |
| SZ_AD2_L2_002.CDF | AD2 | 1372.26 | 1 | 1 |
| SZ_AD20_JS_017.CDF | A20 | 1358.535 | 60.284 | 1 |
| SZ_C11_LM_016.CDF | C11 | 1323.859 | 85.965 | 1 |
| SZ_A22_L2_015.CDF | A22 | 1318.095 | 77.815 | 12.837 |
| SZ_AD244_L2_008.CDF | AD244 | 1255.252 | 28.149 | 1 |
| SZ_A21_L2_006.CDF | A21 | 1248.575 | 21.417 | 1 |
| SZ_AD44_SLOWERGRAD_003.CDF | AD44 | 1246.271 | 28.842 | 1 |
| SZ_AD5_SLOWERGRAD_002.CDF | AD5 | 1198.832 | 1 | 58.575 |
| SZ_E10_JS_010.CDF | E10 | 1166.344 | 36.894 | 1 |
| SZ_AD15_L2_009.CDF | AD15 | 1036.004 | 1 | 1 |
| SZ_A6_L2_002.CDF | A6 | 767.052 | 1 | 1 |

Tables 6-8 show the other retention times that have similar masses in the top 25% and lowest 25% of the data.

TABLE 6

Data somewhat corresponding to retention time 3.53 min in Aug data (masses are not similar between Data Set A and Data Set B)

| Raw Data | Sample Name | 237/90.8027 mz/ 3.80 min | 96/92.8056 mz/ 3.80 min |
|---|---|---|---|
| Highest Quartile, not highest quartile | | | |
| SZ_AD55_JS_NEWRAMP3_009.CDF | AD55 | 1829.707 | 907.667 |
| SZ_A25_L2_002.CDF | L2 | 1236.781 | 465.3175 |
| SZ_AD33_SLOWERGRAD_005.CDF | AD33 | 1213.878 | 380.685 |
| SZ_AD14_MS_004.CDF | AD14 | 1211.287 | 530.948 |
| SZ_AD3_MS_003.CDF | AD33 | 1204.637 | 457.2895 |
| SZ_A14_L2_004.CDF | A14 | 1197.947 | 463.524 |
| SZE13LM 008.CDF | E13 | 1183.106 | 510.894 |
| SZ_D24_LM_006.CDF | D24 | 1157.946 | 322.012 |
| SZ_AD2_L2_002.CDF | AD2 | 1130.862 | 323.278 |
| SZ_C13_JS_009.CDF | C13 | 1128.181 | 525.7715 |
| SZ_AD50_SLOWERGRAD_004.CDF | AD50 | 1124.335 | 398.223 |
| SZ_B8_JS_008.CDF | B8 | 1050.69 | 334.524 |
| SZ_C7_JS_005.CDF | C7 | 1039.446 | 435.5115 |
| SZ_C3_LH_003.CDF | C3 | 1021.188 | 311.7775 |
| SZ_C15_LM_006.CDF | C15 | 1015.984 | 215.44 |
| SZ_AD14_MS_014.CDF | AD14 | 1012.418 | 408.7545 |
| SZ_D4_JS_007.CDF | D4 | 1006.497 | 412.414 |
| SZ_AD56_L2_005.CDF | AD56 | 989.263 | 223.188 |
| Lowest Quartile, Not lowest Quartile | | | |
| SZ_AD27_JS_005.CDF | AD27 | 675.2885 | 339.538 |
| SZ_A13_JS_003.CDF | A13 | 670.6425 | 211.967 |
| SZ_A6_L2_002.CDF | A6 | 647.4895 | 156.718 |
| SZ_5_005.CDF | 5 | 636.974 | 301.912 |
| SZ_6_009.CDF | 6 | 615.924 | 313.1045 |
| SZ_13_008.CDF | 13 | 613.1725 | 393.8025 |
| SZ_15_012.CDF | 15 | 593.4915 | 358.671 |
| SZ_D12_SLOWERGRAD_010.CDF | D12 | 586.147 | 387.0505 |
| SZ_A16_SLOWERGRAD_008.CDF | A16 | 567.631 | 152.2685 |
| SZ_VALVE22_003.CDF | Valve22 | 560.384 | 399.01 |
| SZ_4_013.CDF | 4 | 558.0395 | 329.0755 |
| SZ_25_011.CDF | 25 | 557.545 | 373.0275 |
| SZ_27_015.CDF | 27 | 554.303 | 271.731 |

TABLE 6-continued

Data somewhat corresponding to retention time 3.53 min in Aug data (masses are not similar between Data Set A and Data Set B)

| Raw Data | Sample Name | 237/90.8027 mz/ 3.80 min | 96/92.8056 mz/ 3.80 min |
|---|---|---|---|
| SZ_A23_SLOWERGRAD_009.CDF | A23 | 547.1245 | 216.843 |
| SZ_POST_LEVY_NEWRAMP_010.CDF | Post Levy | 546.554 | 208.455 |
| SZ_20_014.CDF | 20 | 525.272 | 202.8755 |
| SZ_3_010.CDF | 3 | 511.1785 | 230.6745 |
| SZ_24_004.CDF | 24 | 501.9515 | 343.4015 |

TABLE 7

Data corresponding to 3.68 min data

| Raw Data Name | Sample Name | 33/97.0027 mz/ 3.79 min | 176/111.7699mz/ 3.79 min | 234/127.0192 mz/ 3.79 min |
|---|---|---|---|---|
| *Highest Quartile, not highest quartile* | | | | |
| SZ_AD55_JS_NEWRAMP3_009.CDF | Ad55 | 45370.71 | 20806.43 | 38518.84 |
| SZ_7_010.CDF | 7 | 30710.1 | 12700.16 | 28218 |
| SZ_AD_14_MS_004.CDF | AD14 | 28654.31 | 18615.08 | 26107.56 |
| SZ_C13_JS_009.CDF | C13 | 28023.2 | 18197.41 | 27151.24 |
| SZ_1_002.CDF | 1 | 27573.2 | 10854.24 | 24612.24 |
| SZ_A14_L2_004.CDF | A14 | 27377.51 | 14308.14 | 23895.98 |
| SZ_AD7_L2_013.CDF | AD7 | 27295.76 | 14861.61 | 23426.51 |
| SZA25L2 002.CDF | A25 | 27191.07 | 15086.54 | 24416.98 |
| SZ_B8_JS_008.CDF | B8 | 26779.48 | 16057.21 | 23541.81 |
| SZ_AD3_MS_003.CDF | AD3 | 26592.99 | 18009.45 | 25209.92 |
| SZ_A8_JS_012.CDF | A8 | 26479.03 | 13981.42 | 23544.45 |
| SZ_AD50_SLOWERGRAD_004.CDF | AD50 | 26432.77 | 13919.8 | 23864.33 |
| SZ_D24_LM_006.CDF | D24 | 26403.33 | 16339.96 | 24505.41 |
| SZ_AD6_MS_004.CDF | AD6 | 25934.98 | 13868.35 | 23829.2 |
| SZ_AD33_SLOWERGRAD_005.CDF | AD33 | 25823.78 | 15770.23 | 24037.61 |
| SZ_C7_JS_005.CDF | C7 | 25351.06 | 15921.14 | 24384.26 |
| SZ_AD14_MS_014.CDF | AD14 | 25015 | 16464.67 | 23252.24 |
| SZ_E13_LM_008.CDF | C13 | 24995.62 | 18617.3 | 25378.71 |
| SZ_AD20_JS_017.CDF | AD20 | 24933.97 | 13161.99 | 22657.5 |
| *Lowest Quartile. Or Not lowest Quartile* | | | | |
| SZ_AD5_SLOWERGRAD_002.CDF | AD5 | 19730.85 | 9766.892 | 16465.34 |
| SZ_VALVE22_003.CDF | Valve 22 | 19663.9 | 8187.309 | 19691.95 |
| SZ_A21_L2_006.CDF | A21 | 19484.15 | 11180.51 | 17797.63 |
| SZ_A16_SLOWERGRAD_008.CDF | A16 | 19379.12 | 10207.05 | 17248.51 |
| SZ_25_011.CDF | 25 | 19361.11 | 8733.576 | 21431.32 |
| SZ_POST_LEVY_NEWRAMP_010.CDF | PostLevy | 19271.3 | 8207.461 | 18172.49 |
| SZ_A13_JS_003.CDF | A13 | 19084.75 | 10280.04 | 18324.75 |
| SZ_5_005.CDF | 5 | 19072.19 | 8306.722 | 21113.61 |
| SZ_27_015.CDF | 27 | 18414.56 | 8141.893 | 19411.7 |
| SZ_15_012.CDF | 15 | 18354.12 | 8187.829 | 19293.76 |
| SZ_3_010.CDF | 3 | 18294.67 | 7803.813 | 18935.94 |
| SZ_A22_L2_015.CDF | A22 | 18017.62 | 11509.92 | 17913.81 |
| SZ_4_013.CDF | 4 | 17535.35 | 8057.858 | 16434.94 |
| SZ_E10_JS_010.CDF | E10 | 17404.72 | 9887.275 | 16566.51 |
| SZ_24_004.CDF | 24 | 17306 | 7768.042 | 19121.71 |
| SZ_AD15_L2009.CDF | A15 | 16306.37 | 9535.646 | 14804.2 |
| SZ_A6_L2_002.CDF | A6 | 15633.03 | 8462.27 | 13975.62 |
| SZ_20_014.CDF | 20 | 14400.06 | 6530.087 | 15983.3 |

TABLE 8

Data corresponding to 3.94 min data, the optimal matching ion is 146

| Raw Data name | Sample name | 212/146.5202 mz/ 7.61 min | 238/86.4858 mz/ 7.61 min | 225/102.6128 mz/ 7.62 min | 276/136.6017 mz/ 7.61 min |
|---|---|---|---|---|---|
| *Highest Quartile or NOT* | | | | | |
| SZ_POST_LEVY_NEWRAMP_010.CDF | post levy | 1674.954 | 1586.913 | 2120.477 | 815.1765 |
| SZ_AD2_L2_002.CDF | AD2 | 763.4315 | 1294.668 | 1961.084 | 245.382 |
| SZ_A20_JS_005.CDF | A20 | 643.065 | 2090.545 | 1367.459 | 233.127 |
| SZ_A25_L2_002.CDF | A25 | 633.381 | 2193.089 | 1489.074 | 111.615 |

TABLE 8-continued

Data corresponding to 3.94 min data, the optimal matching ion is 146

| Raw Data name | Sample name | 212/146.5202 mz/ 7.61 min | 238/86.4858 mz/ 7.61 min | 225/102.6128 mz/ 7.62 min | 276/136.6017 mz/ 7.61 min |
|---|---|---|---|---|---|
| SZ_1_002.CDF | 1 | 451.6445 | 1670.223 | 1094.59 | 153.5655 |
| SZ_AD5_SLOWERGRAD_002.CDF | AD5 | 434.0335 | 1463.172 | 1056.681 | 70.202 |
| SZ_D4_JS_007.CDF | D4 | 384.058 | 1812.007 | 1062.7 | 102.1615 |
| SZ_A6_L2_002.CDF | A6 | 250.137 | 1313.233 | 607.3385 | 52.0925 |
| SZ_AD244_L2_008.CDF | AD244 | 223.1045 | 1153.193 | 622.369 | 41.58 |
| SZ_27_015.CDF | 27 | 200.384 | 1492.889 | 846.379 | 62.04 |
| SZ_A15_JS_SLOWERGRAD_012.CDF | A15 | 200.261 | 1193.05 | 569.8395 | |
| SZAD55JSNEWRAMP3_009.CDF | AD55 | 192.21 | 1162.376 | 689.9545 | 126.175 |
| SZ_20_014.CDF | 20 | 141.7775 | 1062.795 | 577.502 | |
| SZ_E10_JS_010.CDF | E10 | 122.916 | 1212.349 | 471.4135 | 23.991 |
| SZ_6_009.CDF | 6 | 88.477 | 948.502 | 391.126 | 13.959 |
| SZ_AD33_SLOWERGRAD_005.CDF | AD33 | 80.709 | 792.192 | 311.151 | |
| | | Lowest Quartile or NOT | | | |
| SZ_C3_LH_003.CDF | C3 | 26.928 | 1078.892 | 322.9545 | |
| SZ_E13_LM_008.CDF | E13 | 26.103 | 1371.137 | 349.731 | |
| SZ_C15_LM_006.CDF | C15 | 25.806 | 1281.96 | 310.3735 | |
| SZ_AD49_L2_011.CDF | AD49 | 24.5235 | 766.522 | 162.498 | |
| SZ_D12_SLOWERGRAD_010.CDF | D12 | 24.453 | 917.146 | 260.0745 | |
| SZ_AD6_MS_004.CDF | AD6 | 13.497 | 939.1435 | 167.8865 | |
| SZ_A4_JS_007.CDF | A4 | 13.233 | 751.483 | 197.224 | |
| SZ_AD14_MS_014.CDF | AD14 | 12.969 | 1233.677 | 335.4395 | 14.685 |
| SZ_C11_LM_016.CDF | C11 | 12.408 | 1009.668 | 285.038 | |
| SZ_A13_JS_003.CDF | A13 | 12.309 | 639.2045 | 97.683 | |
| SZ_AD4_MS_009.CDF | AD49 | 11.946 | 973.759 | 158.744 | |
| SZ_13_008.CDF | 13 | 11.418 | 926.487 | 320.874 | |
| SZ_15_012.CDF | 15 | 11.319 | 918.113 | 217.2635 | |
| SZ_A8_JS_012.CDF | A8 | 10.692 | 1141.676 | 301.6715 | |
| SZ_A2_JS_SLOWERGRAD_011.CDF | A2 | 10.527 | 692.7165 | 335.727 | 10.8665 |
| SZ_4_013.CDF | 4 | 10.3075 | 1162.103 | 300.995 | 10.197 |
| SZ_A17_JS_006.CDF | A17 | | 859.7025 | 83.391 | |
| SZ_AD44_SLOWERGRAD_003.CDF | AD44 | | 758.7385 | 252.991 | |
| SZ_A22_L2_015.CDF | A22 | | 978.504 | 143.798 | |
| SZ_AD15_L2_009.CDF | AD15 | | 577.526 | 112.2795 | |
| SZ_AD1_MS_012.CDF | AD1 | | 774.4865 | 218.4395 | |
| SZ_5_005.CDF | 5 | | 971.101 | 268.3705 | |
| SZ_A14_L2_004.CDF | A14 | | 1081.059 | 352.318 | |
| SZ_26_006.CDF | 26 | | 1001.473 | 207.385 | |
| SZ_D15_JS_007.CDF | D15 | | 1087.344 | 307.2945 | |

FIG. 13 shows a table demonstrating samples found to be in the highest (negative for *D. immitis*) and lowest (positive for *D. immitis*) quartiles from Tables 5-8. Columns and rows are organized low to high. The medium gray shading with white lettering indicates that the sample can be found in both the highest and lowest quartiles (for different features). The black shading with white lettering indicates that the sample can be found only in the highest quartiles. The lightest gray shading with black lettering indicates that the sample can be found only in the lowest quartiles. The white with black lettering indicates a sample was only found a single time.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

Further attributes, features, and embodiments of the present invention can be understood by reference to the following numbered aspects of the disclosed invention. Reference to disclosure in any of the preceding aspects is applicable to any preceding numbered aspect and to any combination of any number of preceding aspects, as recognized by appropriate antecedent disclosure in any combination of preceding aspects that can be made. The following numbered aspects are provided:

1. A Dirofilaria exhalant signature comprising:
   one or more volatile organic compounds (VOCs) selected from the group consisting of: an aromatic hydrocarbon, a monoterpene, a cyclopentanone, an aziridine, an alkane hydrocarbon, a phenol, a ketone, and combinations thereof.
2. The Dirofilaria exhalant signature of aspect 1, wherein the number of VOCs in the Dirofilaria exhalant signature is 1, 2, 3, 4, 5, 6, 7, 8, 9, 10, 11, 12, 13, 15, or 15.
3. The Dirofilaria exhalant signature of any one of aspects 1-2, wherein the number of VOCs in the Dirofilaria exhalant signature is 9 and wherein the 9 VOCs are an aromatic hydrocarbon, a monoterpene, an alkyl alcohol, a cyclopentanone, an aziridine, two alkane hydrocarbons, a phenol, and a ketone.
4. The Dirofilaria exhalant signature of any one of aspects 1-3, wherein the one or more VOCs are ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

5. The Dirofilaria exhalant signature of any one of aspects 1-4, wherein the one or more VOCs are selected from the group consisting of: ortho xylene, p-Methane-1,2,3-triol, 3,7,11-trimethyl-1-Dodecanol, 2-ethyl-Cyclohexanone, 2-mehtyl-2-(2,2,4,4,6,6-hexamethylheptyl)-Aziridine, 1,2,3,6,7,8,8a,8b-octahydro, trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

6. The Dirofilaria exhalant signature of any one of aspects 1-5, wherein the Dirofilaria exhalant signature is a Dirofilaria *immitis, Dirofilaria repens, Dirofilaria tenuis, Dirofilaria ursi*, D. subdermata, *D. striata*, or a *D. hongkongensis* exhalant signature.

7. A non-invasive method of diagnosing, prognosing, staging, and/or monitoring Dirofilaria infection in a subject, the method comprising:
detecting a Dirofilaria exhalant signature in an exhalant sample obtained from the subject, wherein the Dirofilaria exhalant signature is as in any one of any one of aspects 1-6,
whereby detection of a decrease, increase, or both of one or more VOCs of the Dirofilaria exhalant signature as compared to a threshold value, a suitable control, or both indicates the presence or absence of Dirofilaria infection in the subject.

8. The method of aspect 7, wherein the Dirofilaria infection is a Dirofilaria *immitis* infection.

9. The method of any one of aspects 7-8, wherein the subject is a human.

10. The method of any one of aspects 7-8, wherein the subject is a non-human animal.

11. The method of aspect 10, the subject is a canine.

12. A method of treating and/or preventing Dirofilaria infection in a subject, the method comprising:
non-invasively diagnosing, prognosing, and/or staging Dirofilaria infection in the subject by detecting a Dirofilaria exhalant signature in an exhalant sample obtained from the subject, wherein the Dirofilaria exhalant signature is as in any one of aspects 1-6,
whereby detection of a decrease, increase, or both of one or more VOCs of the Dirofilaria exhalant signature as compared to a threshold value, a suitable control, or both indicates the presence or absence of Dirofilaria infection in the subject; and
administering to the subject an anthelmintic effective to prevent at least the adult stage of Dirofilaria in the subject one or more times, administering to the subject a treatment effective to kill the adult stage of Dirofilaria in the subject one or more times, or both.

13. The method of aspect 12, wherein the subject is a canine.

14. The method of aspects 12-13, wherein the Dirofilaria is *D. immitis*.

15. The method of any one of aspects 12-14, wherein the anthelmintic effective to prevent at least the adult stage of Dirofilaria comprises:
ivermectin, moxidectin, milbemycin oxime, selamectin, eprinomectin, or a combination thereof.

16. The method of any one of aspects 12-15, further comprising co-administering a composition effective to prevent, treat, or both an intestinal parasite, an external parasite, or both.

17. The method of any one of aspects 12-16, wherein the composition effective to prevent, treat, or both an intestinal parasite, an external parasite, or both is one or more compounds of one or more of the following classes benzimidazole, piperazine, depolarizing tetrahydropyrimidines, a macrocyclic lactone, neonicotinoid, phenylpyrazole, oxadiazine, pyrethrin, pyrethroid, isoxazoline, an insect growth regulator, or any combination thereof.

18. The method of any one of aspects 12-17, wherein the composition effective to prevent, treat, or both an intestinal parasite, external parasite, or both is pyrantel, pyrantel pamoate, febantel, praziquantel, oxibendazole, piperazine, spinosad, fluralaner, afoxolaner, fipronil, sarolaner, lotilaner, lufenuron, imidacloprid, Methoprene, S-methoprene, pyriproxyfen, fenbendazole, flumethrin, selamectin, eprinomectin, indoxacarb, permethrin, nitenpyram, or any combination thereof.

19. The method of any one of aspects 12-18, wherein the treatment effective to kill the adult stage of Dirofilaria comprises administering melarsomine to the subject.

20. The method of any one of aspects 12-18, wherein the treatment effective to kill the adult stage of Dirofilaria comprises administering a macrocyclic lactone anthelmintic effective to kill adult Dirofilaria.

21. The method of any one of aspects 12-20, wherein the subject is administered treatment effective to kill the adult stage of Dirofilaria and the method further comprises administering an amount of doxycycline for two or more concurrent days to the subject.

22. The method of aspect 21, wherein the amount of doxycycline is administered for about 30 days.

23. A device configured to collect an exhalant for analysis of volatile organic compounds (VOCs) present in the exhalant of a single non-human animal subject, comprising:
an exhalant collector configured to actively and non-invasively collect exhalant expelled from the non-human animal subject without being placed in an orifice of the subject; and
one or more removable collection chambers, each removable collection chamber configured to hold an amount of exhalant collected and are suitable for containment of VOCs, wherein the one or more removable collection chambers are operatively coupled to the exhalant collector.

24. The device of aspect 23, wherein the exhalant collector comprises or is coupled to one or more low pressure air pumps capable of moving exhalant external to the device into the exhalant collector and into the one or more removable collection chambers.

25. The device any one of aspects 23-24, wherein the device comprises one or more one-way air valves configured to control the flow of exhalant in one direction through the device from the external environment through the exhalant collector and into and optionally through the one or more removable collection chambers.

26. The device of any one of aspects 23-25, wherein the exhalant collector is a tube that is configured to be placed in effective proximity to a mouth, nose, nostrils, or a combination thereof of the subject during collection and draw exhalant into the exhalant collector.

27. The device of any one of aspects 23-25, wherein the exhalant collector is a mask that is configured to cover the mouth and nose of the subject.

28. The device of any one of aspects 23-27, wherein the exhalant collector, the one or more removable collection chambers, or both comprise one or more filters.

29. The device of aspect 28, wherein at least one of the one or more filters is effective to remove environmental VOCs from exhalant collected.
30. The device of any one of aspects 23-29, wherein the exhalant collector is operatively coupled to the one or more removable collection chambers via one or more tubes.
31. The device of any one of aspects 23-30, wherein the one or more removable collection chambers is configured to preserve VOCs for analysis.
32. The device of any one of aspects 23-30, wherein the one or more removable collection chambers comprises a material capable of capturing and retaining VOCs from collected exhalant.
33. The device of any one of aspects 23-32, wherein the one or more removable collection chambers is capable of concentrating and/or enriching VOCs from collected exhalant.
34. The device of any one of aspects 32-33, wherein the one or more removable collection chambers comprises a material capable of releasing VOCs that are captured by a material in the one or more removable collection chambers.
35. The device of any one of aspects 32-34, wherein the one or more collection chambers are tubes, bags, reservoirs, cartridges, or a combination thereof.
36. A kit comprising:
one or more removable collection chambers configured for the device of any one of aspects 23-35 and instructions fixed in a tangible medium of expression wherein the instructions provide directions for using the one or more removable collection chambers to collect volatile organic compounds from an exhalant of a subject and detecting a Dirofilaria exhalant signature to diagnose, prognose, and/or stage a Dirofilaria infection in the subject.
37. The kit of aspect 36, wherein the one or more removable collection chambers is configured to preserve VOCs for analysis.
38. The kit of any one of aspects 36-37, wherein the one or more removable collection chambers wherein the one or more removable collection chambers is capable of concentrating and/or enriching VOCs from collected exhalant.
39. The kit of any one of aspects 36-37, wherein the one or more removable collection chambers comprises a material capable of releasing VOCs that are captured by a material in the one or more removable collection chambers.
40. A kit comprising a device as in any one of aspects 23-35 and directions fixed in a tangible medium of expression for using the one or more removable collection chambers to collect volatile organic compounds from an exhalant of a subject and detecting a Dirofilaria exhalant signature to diagnose, prognose, and/or stage a Dirofilaria infection in the subject.
41. Use of a Dirofilaria exhalant signature in an exhalant sample to diagnose, prognose, monitor, treat, or prevent Dirofilaria infection in a subject or any combination thereof.

What is claimed is:

1. A method of non-invasively detecting Dirofilaria infection in a subject, the method comprising:
(a) detecting a Dirofilaria exhalant signature in an exhalant sample obtained from the subject, wherein the Dirofilaria exhalant signature comprises one or more volatile organic compounds (VOCs) selected from the group consisting of: an aromatic hydrocarbon, a monoterpene, a cyclopentanone, an aziridine, an alkane hydrocarbon, a phenol, a ketone, and combinations thereof,
whereby detection of a decrease or increase of one or more VOCs of the Dirofilaria exhalant signature as compared to a threshold value, a suitable control, or both indicates the presence or absence of Dirofilaria infection in the subject wherein the one or more VOCs are selected from the group consisting of: ortho xylene, p-Methane-1,2,3-triol, 3,7,11-trimethyl-1-Dodecanol, 2-ethyl-Cyclohexanone, 2-methyl-2-(2,2,4,4,6,6-hexamethylheptyl)-Aziridine, 1,2,3,6,7,8,8a,8b-octahydro-trans-Biphenylene, 2,6,10-trimethyl-tetradecane, 5,6,6-Trimethyl-5-(3-oxobut-1-enyl)-1-oxaspiro[2.5]octan-4-one, and 5,5-Dibutylnonane.

2. The method of claim 1, further comprising
(b) administering to a subject determined in step (a) to not have a Dirofilaria infection an anthelmintic effective to prevent at least the adult stage of Dirofilaria in the subject one or more times; or
(c) administering to a subject determined in step (a) to have a Dirofilaria infection a treatment effective to kill the adult stage of Dirofilaria in the subject one or more times, an anthelmintic effective to prevent at least the adult stage of Dirofilaria in the subject one or more times or both.

3. The method of claim 1, wherein the number of VOCs in the Dirofilaria exhalant signature is 1, 2, 3, 4, 5, 6, 7, 8, 9, 10, 11, 12, 13, 14, or 15.

4. The method of claim 1, wherein the Dirofilaria is Dirofilaria *immitis, Dirofilaria repens, Dirofilaria tenuis, Dirofilaria ursi, D. subdermata, D. striata*, or a *D. hongkongensis*.

5. The method of claim 1, wherein the anthelmintic effective to prevent at least the adult stage of Dirofilaria comprises:
ivermectin, moxidectin, milbemycin oxime, selamectin, eprinomectin, or any combination thereof.

6. The method of claim 1, further comprising co-administering a composition effective to prevent, treat, or both an intestinal parasite, external parasite, or both.

7. The method of claim 5, wherein the composition effective to prevent, treat, or both an intestinal parasite, external parasite, or both is one or more compounds of one or more of the following classes benzimidazole, piperazine, depolarizing tetrahydropyrimidines, a macrocyclic lactone, neonicotinoid, phenylpyrazole, oxadiazine, pyrethrin, pyrethroid, isoxazoline, an insect growth regulator, and any combination thereof.

8. The method of claim 6, wherein the composition effective to prevent, treat, or both an intestinal parasite, external parasite, or both is selected from pyrantel, pyrantel pamoate, febantel, praziquantel, oxibendazole, piperazine, spinosad, fluralaner, afoxolaner, fipronil, sarolaner, lotilaner, lufenuron, imidacloprid, Methoprene, S-methoprene, pyriproxyfen, fenbendazole, flumethrin, selamectin, eprinomectin, indoxacarb, permethrin, nitenpyram, and any combination thereof.

9. The method of claim 1, wherein the treatment effective to kill the adult stage of Dirofilaria comprises administering melarsomine to the subject.

10. The method of claim 1, wherein the treatment effective to kill the adult stage of Dirofilaria comprises administering a macrocyclic lactone anthelmintic effective to kill adult Dirofilaria.

11. The method of claim 1, wherein the subject is administered treatment effective to kill the adult stage of Dirofilaria and the method further comprises administering an amount of doxycycline for two or more concurrent days to the subject, and wherein the amount of doxycycline is optionally administered for about 30 days.

12. The method of claim 1, wherein the subject is a human.

13. The method of claim 1, wherein the subject is a non-human animal.

14. The method of claim 13, wherein the subject is a canine.

\* \* \* \* \*